(12) United States Patent
Kramer-Brown et al.

(10) Patent No.: US 10,441,445 B2
(45) Date of Patent: *Oct. 15, 2019

(54) RADIOPAQUE INTRALUMINAL STENTS COMPRISING COBALT-BASED ALLOYS CONTAINING ONE OR MORE PLATINUM GROUP METALS, REFRACTORY METALS, OR COMBINATIONS THEREOF

(71) Applicant: Abbott Cardiovascular Systems, Inc., Santa Clara, CA (US)

(72) Inventors: Pamela A. Kramer-Brown, Sparks, NV (US); Kayla L. Calvert, Mountain House, CA (US); John A. Simpson, Carlsbad, CA (US); Stephen D. Pacetti, San Jose, CA (US); Austin M. Leach, Oakland, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 322 days.

This patent is subject to a terminal disclaimer.

(21) Appl. No.: 15/429,339

(22) Filed: Feb. 10, 2017

(65) Prior Publication Data

US 2017/0296365 A1 Oct. 19, 2017

Related U.S. Application Data

(60) Division of application No. 13/830,404, filed on Mar. 14, 2013, now Pat. No. 9,566,147, which is a
(Continued)

(51) Int. Cl.
*C22C 19/07* (2006.01)
*A61F 2/82* (2013.01)
(Continued)

(52) U.S. Cl.
CPC .............. *A61F 2/82* (2013.01); *A61F 2/06* (2013.01); *A61L 31/022* (2013.01); *A61L 31/18* (2013.01);
(Continued)

(58) Field of Classification Search
CPC ..................................... C22C 19/07
See application file for complete search history.

(56) References Cited

U.S. PATENT DOCUMENTS

| | | |
|---|---|---|
| 3,635,703 A | 1/1972 | Pissarevsky |
| 4,685,977 A | 8/1987 | Chang |

(Continued)

FOREIGN PATENT DOCUMENTS

| | | |
|---|---|---|
| EP | 0804934 | 8/2003 |
| EP | 1604691 | 12/2005 |

(Continued)

OTHER PUBLICATIONS

U.S. Appl. No. 61/414,566, filed Nov. 17, 2010, Boylan.
(Continued)

*Primary Examiner* — Jessee R Roe
(74) *Attorney, Agent, or Firm* — Workman Nydegger; Randy Shen

(57) ABSTRACT

Embodiments are directed to radiopaque implantable structures (e.g., stents) formed of cobalt-based alloys that comprise cobalt, chromium and one or more platinum group metals, refractory metals, precious metals, or combinations thereof. Platinum group metals include platinum, palladium, ruthenium, rhodium, osmium, and iridium. Refractory metals include zirconium, niobium, rhodium, molybdenum, hafnium, tantalum, tungsten, rhenium, and precious metals include silver and gold. In one embodiment, the one or more included platinum group or refractory metals substitute at least partially for nickel, such that the alloy exhibits reduced
(Continued)

nickel content, or is substantially nickel free. The stents exhibit improved radiopacity as compared to similar alloys including greater amounts of nickel.

21 Claims, 53 Drawing Sheets

Related U.S. Application Data continuation-in-part of application No. 13/298,070, filed on Nov. 16, 2011, now abandoned.

(60) Provisional application No. 61/414,566, filed on Nov. 17, 2010.

(51) Int. Cl.
| | | |
|---|---|---|
| *A61F 2/06* | (2013.01) | |
| *A61L 31/02* | (2006.01) | |
| *A61L 31/18* | (2006.01) | |
| *C22C 1/04* | (2006.01) | |
| C22C 19/05 | (2006.01) | |
| C22C 27/00 | (2006.01) | |
| C22C 27/04 | (2006.01) | |
| C22C 27/06 | (2006.01) | |

(52) U.S. Cl.
CPC ............ *C22C 1/0433* (2013.01); *C22C 19/07* (2013.01); *A61F 2250/0098* (2013.01); *C22C 19/05* (2013.01); *C22C 27/00* (2013.01); *C22C 27/04* (2013.01); *C22C 27/06* (2013.01)

(56) References Cited

U.S. PATENT DOCUMENTS

| | | |
|---|---|---|
| 5,061,275 A | 10/1991 | Wallsten et al. |
| 5,330,826 A | 7/1994 | Taylor et al. |
| 5,421,955 A | 6/1995 | Lau et al. |
| 5,514,154 A | 5/1996 | Lau et al. |
| 5,569,295 A | 10/1996 | Lam |
| 5,603,721 A | 2/1997 | Lau et al. |
| 5,618,299 A | 4/1997 | Khosravi et al. |
| 5,628,787 A | 5/1997 | Mayer |
| 5,630,840 A | 5/1997 | Mayer |
| 5,636,641 A | 6/1997 | Fariabi |
| 5,649,952 A | 7/1997 | Lam |
| 5,716,417 A | 2/1998 | Girard et al. |
| 5,725,572 A | 3/1998 | Lam et al. |
| 5,728,158 A | 3/1998 | Lau et al. |
| 5,735,893 A | 4/1998 | Lau et al. |
| 5,759,192 A | 6/1998 | Saunders |
| 5,766,238 A | 6/1998 | Lau et al. |
| 5,799,386 A | 9/1998 | Ingersoll et al. |
| 5,824,077 A | 10/1998 | Mayer |
| 5,849,037 A | 12/1998 | Frid |
| 5,876,432 A | 3/1999 | Lau et al. |
| 5,891,191 A | 4/1999 | Stinson |
| 5,984,973 A | 11/1999 | Girard et al. |
| 6,027,528 A | 2/2000 | Tomanto et al. |
| 6,221,096 B1 | 4/2001 | Aiba et al. |
| 6,287,331 B1 | 9/2001 | Heath |
| 6,355,058 B1 | 3/2002 | Pacetti et al. |
| 6,419,693 B1 | 7/2002 | Fariabi |
| 6,620,192 B1 | 9/2003 | Jalisi |
| 7,105,018 B1 | 9/2006 | Yip et al. |
| 7,156,869 B1 | 1/2007 | Pacetti |
| 7,250,058 B1 | 7/2007 | Pacetti et al. |
| 7,294,214 B2 | 11/2007 | Craig |
| 7,318,837 B2 | 1/2008 | Krivoruchko et al. |
| 7,413,574 B2 | 8/2008 | Yip et al. |
| 7,488,343 B2 | 2/2009 | O'Brien et al. |
| 7,540,997 B2 | 6/2009 | Stinson |
| 7,601,230 B2 | 10/2009 | Craig |
| 7,740,798 B2 | 6/2010 | Stinson |
| 8,430,923 B2 | 4/2013 | Pacetti et al. |
| 8,852,264 B2 | 10/2014 | Pacetti et al. |
| 9,566,174 B1 | 2/2017 | Kramer-Brown et al. |
| 2002/0032477 A1 | 3/2002 | Helmus et al. |
| 2004/0129347 A1 | 7/2004 | Craig |
| 2004/0236433 A1 | 11/2004 | Kennedy et al. |
| 2005/0059889 A1 | 3/2005 | Mayer |
| 2005/0060025 A1 | 3/2005 | Mackiewicz et al. |
| 2006/0190070 A1 | 8/2006 | Dieck et al. |
| 2006/0259126 A1 | 11/2006 | Lenz |
| 2006/0271169 A1 | 11/2006 | Lye et al. |
| 2006/0287709 A1 | 12/2006 | Rao |
| 2007/0135891 A1 | 6/2007 | Schneider |
| 2007/0173925 A1 | 7/2007 | Fliedner |
| 2007/0219624 A1 | 9/2007 | Brown et al. |
| 2007/0265699 A1 | 11/2007 | Grewe et al. |
| 2007/0270942 A1 | 11/2007 | Thomas |
| 2008/0070058 A1 | 3/2008 | Dasgupta et al. |
| 2008/0091267 A1 | 4/2008 | Stinson et al. |
| 2008/0160259 A1 | 7/2008 | Nielson et al. |
| 2008/0177371 A1 | 7/2008 | Ryan et al. |
| 2008/0183280 A1 | 7/2008 | Agnew et al. |
| 2008/0208308 A1 | 8/2008 | Allen et al. |
| 2008/0208352 A1 | 8/2008 | Krivoruchko et al. |
| 2008/0215132 A1 | 9/2008 | Ryan et al. |
| 2008/0262600 A1 | 10/2008 | Jalisi |
| 2009/0030500 A1 | 1/2009 | Weber |
| 2009/0048659 A1 | 2/2009 | Weber et al. |
| 2009/0093871 A1 | 4/2009 | Rea et al. |
| 2009/0118822 A1 | 5/2009 | Holman et al. |
| 2009/0149947 A1 | 7/2009 | Frohwitter |
| 2009/0240324 A1 | 9/2009 | Smith |
| 2009/0258050 A1 | 10/2009 | Lindsay et al. |
| 2009/0259299 A1 | 10/2009 | Moloney |
| 2009/0276033 A1 | 11/2009 | Mayer |
| 2010/0004733 A1 | 1/2010 | Atanasoska et al. |
| 2010/0217373 A1 | 8/2010 | Boyle et al. |
| 2010/0222873 A1 | 9/2010 | Atanasoska et al. |
| 2010/0241210 A1 | 9/2010 | Patadia |
| 2012/0123525 A1 | 5/2012 | Kramer-Brown et al. |

FOREIGN PATENT DOCUMENTS

| | | |
|---|---|---|
| EP | 1632584 | 3/2006 |
| EP | 1829982 | 9/2007 |
| EP | 2676684 | 12/2013 |
| EP | 2676686 | 12/2013 |
| WO | WO 97/33534 | 9/1997 |
| WO | WO 99/15108 | 4/1999 |
| WO | WO 00/54704 | 9/2000 |
| WO | WO 01/15632 | 3/2001 |
| WO | WO 01/17577 | 3/2001 |
| WO | WO 01/72349 | 10/2001 |
| WO | WO 02/078763 | 10/2002 |
| WO | WO 12/068358 | 5/2012 |
| WO | WO 13/162690 | 10/2013 |
| WO | WO 14/159743 | 10/2014 |

OTHER PUBLICATIONS

Giessen et al., "Coronary Stenting with a New Radiopaque Balloon Expandable Endoprosthesis in Pigs", Circulation, vol. 83, No. 5, May 1991, pp. 1788-1798.
Cordis Palmaz Blue .018 Peripheral Stent System, Johnson & Johnson Medical NV/SA, May 2005 (2 pages) http://www.jjnordic.com/Lists/FileList1/Attatchments/174/PalmazBlue_018_Brochure.PDF.
Ohring et al. "A Versatile Arc Melting Apparatus for Quenching Molten Metals and Ceramics." Review of Scientific instruments 42.4 (1971): 530-531.
U.S. Appl. No. 09/534,071, Sep. 17, 2002, Office Action.
U.S. Appl. No. 09/534,071, Dec. 18, 2002, Office Action.
U.S. Appl. No. 09/534,071, Jul. 9, 2003, Office Action.
U.S. Appl. No. 09/534,071, Aug. 29, 2005, Office Action.
U.S. Appl. No. 09/534,071, Nov. 15, 2005, Office Action.
U.S. Appl. No. 09/534,071, Mar. 13, 2006, Office Action.

(56) References Cited

OTHER PUBLICATIONS

U.S. Appl. No. 09/534,071, Sep. 13, 2006, Office Action.
U.S. Appl. No. 09/534,071, Feb. 12, 2007, Notice of Allowance.
U.S. Appl. No. 09/534,071, Jul. 11, 2007, Issue Notification.
U.S. Appl. No. 11/736,979, May 26, 2010, Office Action.
U.S. Appl. No. 11/736,979, Aug. 31, 2010, Office Action.
U.S. Appl. No. 11/736,979, Apr. 4, 2011, Office Action.
U.S. Appl. No. 11/736,979, Sep. 19, 2011, Office Action.
U.S. Appl. No. 11/736,979, Apr. 12, 2012, Office Action.
U.S. Appl. No. 11/736,979, Nov. 9, 2012, Notice of Allowance.
U.S. Appl. No. 13/298,070, May 2, 2014, Office Action.
U.S. Appl. No. 13/298,070, Jun. 25, 2014, Office Action.
U.S. Appl. No. 13/298,070, Oct. 6, 2014, Office Action.
U.S. Appl. No. 13/618,602, Mar. 4, 2013, Office Action.
U.S. Appl. No. 13/618,602, May 3, 2013, Office Action.
U.S. Appl. No. 13/618,602, Aug. 20, 2013, Office Action.
U.S. Appl. No. 13/618,602, Jan. 6, 2014, Office Action.
U.S. Appl. No. 13/618,602, May 27, 2014, Notice of Allowance.
U.S. Appl. No. 13/830,404, May 29, 2015, Office Action.
U.S. Appl. No. 13/830,404, Sep. 16, 2015, Office Action.
U.S. Appl. No. 13/830,404, Jan. 8, 2016, Office Action.
U.S. Appl. No. 13/830,404, Apr. 20, 2016, Office Action.
U.S. Appl. No. 13/830,404, Aug. 10, 2016, Office Action.
U.S. Appl. No. 13/830,404, Oct. 18, 2016, Notice of Allowance.

RADIOPAQUE INTRALUMINAL STENTS COMPRISING COBALT-BASED ALLOYS CONTAINING ONE OR MORE PLATINUM GROUP METALS, REFRACTORY METALS, OR COMBINATIONS THEREOF

CROSS-REFERENCE TO RELATED APPLICATIONS

The present application is a divisional of U.S. patent application Ser. No. 13/830,404, filed Mar. 14, 2013, which is a continuation in part of U.S. patent application Ser. No. 13/298,070, filed Nov. 16, 2011, now abandoned, which claims the benefit of U.S. Provisional Patent Application Ser. No. 61/414,566 filed Nov. 17, 2010 and entitled RADIOPAQUE INTRALUMINAL STENTS COMPRISING COBALT-BASED ALLOYS CONTAINING ONE OR MORE PLATINUM GROUP METALS, each of which is herein incorporated by reference in its entirety.

BACKGROUND

Intraluminal stents implanted with percutaneous methods have become a standard adjunct to procedures such as balloon angioplasty in the treatment of atherosclerotic disease of the arterial system. Stents, by preventing acute vessel recoil, improve long term patient outcome and have other benefits such as securing vessel dissections.

Intraluminal stents comprise generally tubular-shaped devices which are constructed to hold open a segment of a blood vessel or other anatomical lumen. Intraluminal stents are used in treatment of diseases such as atherosclerotic stenosis as well as diseases of the stomach and esophagus, and for urinary tract applications. Adequate stent function requires a precise placement of the stent over a lesion or site of plaque or other lumen site in need of treatment. Typically, the stent is delivered to a treatment site by a delivery catheter that comprises an expandable portion for expanding the stent within the lumen.

The delivery catheter onto which the stent is mounted may be a balloon delivery catheter similar to those used for balloon angioplasty procedures. In order for the stent to remain in place on the balloon during delivery to the site of damage within a lumen, the stent may be compressed onto the balloon. The catheter and stent assembly is introduced within a patient's vasculature using a guide wire. The guide wire is disposed across the damaged arterial section and then the catheter-stent assembly is advanced over the guide wire within the artery until the stent is directly within the lesion or the damaged section.

The balloon of the catheter is expanded, expanding the stent against the artery wall. The artery is preferably slightly expanded by the expansion of the stent to seat or otherwise fix the stent to prevent movement. In some circumstances during treatment of stenotic portions of the artery, the artery may have to be expanded considerably in order to facilitate passage of blood or other fluid therethrough. In the case of a self expanding stent, the stent is expanded by retraction of a sheath or actuation of a release mechanism. Self expanding stents may expand to the vessel wall automatically without the aid of a dilation balloon, although such a dilation balloon may be used for another purpose.

These manipulations are performed within the body of a patient by a practitioner who may rely upon both placement markers on the stent catheter and on the radiopacity of the stent itself. The stent radiopacity arises from a combination of stent material and stent pattern, including stent strut or wall thickness. After deployment within the vessel, the stent radiopacity should allow adequate visibility of both the stent and the underlying vessel and/or lesion morphology under fluoroscopic visualization.

SUMMARY

Embodiments of the present invention are directed to radiopaque cobalt alloys, radiopaque implantable structures (e.g., stents) and related methods of manufacture and use. One embodiment of the present invention includes a radiopaque implantable structure. The radiopaque implantable structure comprises a main body including a cobalt-based alloy that includes cobalt, chromium, and one or more radiopaque elements. In one embodiment, examples of radiopaque elements include so-called platinum group metals (i.e., platinum, palladium, ruthenium, rhodium, osmium, or iridium). Group 10 elements (i.e., platinum or palladium) are particularly preferred. In one embodiment, the one or more included platinum group metals substitute for nickel, another group 10 element, such that the alloy is substantially nickel free (e.g., includes no more than about 2% nickel by weight). Another embodiment is entirely free of nickel. In addition, the alloys may include iron, although the amount of iron is limited to no more than about 20% by weight. In other embodiments, the amount of iron may be further limited (e.g., no more than about 10% by weight, no more than about 8% by weight). In some embodiments, the alloys are substantially iron free (e.g., no more than about 4% iron by weight). In another embodiment, iron is entirely absent.

In an embodiment, a radiopaque stent comprises a cylindrical main body comprising a cobalt-based alloy including cobalt, chromium and one or more platinum group metals selected from the group consisting of platinum, palladium, rhodium, iridium, osmium, ruthenium, silver and gold the cobalt-based alloy being substantially free of nickel and comprising no more than about 20 percent by weight iron.

In an embodiment, the cobalt-based alloy is entirely free of nickel and comprising no more than about 20 percent by weight iron.

In an embodiment, the cobalt-based alloy being substantially free of nickel and comprising no more than about 16 percent by weight iron.

In an embodiment, the cobalt-based alloy being substantially free of nickel and comprising no more than about 10 percent by weight iron.

In an embodiment, the cobalt-based alloy being substantially free of nickel and comprising no more than about 8 percent by weight iron.

In an embodiment, the cobalt-based alloy being substantially free of nickel and comprising no more than about 4 percent by weight iron.

In an embodiment, the cobalt-based alloy comprises from about 18 weight percent to about 50 weight percent cobalt, from about 10 weight percent to about 25 weight percent chromium, from about 10 weight percent to about 15 weight percent tungsten, from about 0 weight percent to about 2 weight percent manganese, from about 0 weight percent to about 3 weight percent iron, and from about 10 weight percent to about 65 weight percent of the one or more platinum group metals.

In an embodiment, the cobalt-based alloy comprises from about 40 weight percent to about 50 weight percent cobalt, from about 15 weight percent to about 25 weight percent chromium, from about 10 weight percent to about 15 weight percent tungsten, from about 0 weight percent to about 2 weight percent manganese, from about 0 weight percent to about 3 weight percent iron, and from about 10 weight percent to about 35 weight percent of the one or more platinum group metals.

In an embodiment, the cobalt-based alloy comprises from about 18 weight percent to about 50 weight percent cobalt, from about 10 weight percent to about 25 weight percent chromium, from about 10 weight percent to about 15 weight percent tungsten, from about 0 weight percent to about 2 weight percent manganese, from about 0 weight percent to about 3 weight percent iron, and from about 10 weight percent to about 65 weight percent of the one or more platinum group metals, wherein the one or more platinum group metals are selected from the group consisting of platinum and palladium.

In an embodiment, the cobalt-based alloy comprises from about 18 weight percent to about 50 weight percent cobalt, from about 10 weight percent to about 25 weight percent chromium, from about 10 weight percent to about 15 weight percent tungsten, from about 0 weight percent to about 2 weight percent manganese, from about 0 weight percent to about 3 weight percent iron, and from about 10 weight percent to about 65 weight percent of the one or more platinum group metals, wherein the one or more platinum group metals comprise from about 10 atomic percent to about 12 atomic percent of the cobalt-based alloy.

In an embodiment, the cobalt-based alloy comprises from about 22 weight percent to about 40 weight percent cobalt, from about 15 weight percent to about 25 weight percent chromium, from about 4 weight percent to about 7 weight percent molybdenum, from about 0 weight percent to about 2 weight percent manganese, from about 0 weight percent to about 18 weight percent iron, and from about 10 weight percent to about 65 weight percent of the one or more platinum group metals.

In an embodiment, the cobalt-based alloy comprises from about 22 weight percent to about 40 weight percent cobalt, from about 15 weight percent to about 25 weight percent chromium, from about 4 weight percent to about 7 weight percent molybdenum, from about 0 weight percent to about 2 weight percent manganese, from about 0 weight percent to about 18 weight percent iron, and from about 10 weight percent to about 65 weight percent of the one or more platinum group metals, wherein the one or more platinum group metals are selected from the group consisting of platinum and palladium.

In an embodiment, the cobalt-based alloy comprises from about 22 weight percent to about 40 weight percent cobalt, from about 15 weight percent to about 25 weight percent chromium, from about 4 weight percent to about 7 weight percent molybdenum, from about 0 weight percent to about 2 weight percent manganese, from about 0 weight percent to about 18 weight percent iron, and from about 10 weight percent to about 65 weight percent of the one or more platinum group metals, wherein the one or more platinum group metals comprise from about 14 atomic percent to about 16 atomic percent of the cobalt-based alloy.

In an embodiment, the cobalt-based alloy comprises from about 22 weight percent to about 40 weight percent cobalt, from about 15 weight percent to about 25 weight percent chromium, from about 4 weight percent to about 7 weight percent molybdenum, from about 0 weight percent to about 2 weight percent manganese, from about 0 weight percent to about 18 weight percent iron, and from about 10 weight percent to about 65 weight percent of the one or more platinum group metals, wherein the one or more platinum group metals comprise from about 33 atomic percent to about 35 atomic percent of the cobalt-based alloy.

In an embodiment, the cobalt-based alloy comprises from about 18 weight percent to about 39 weight percent cobalt, from about 10 weight percent to about 25 weight percent chromium, from about 5 weight percent to about 10 weight percent molybdenum, and from about 10 weight percent to about 65 weight percent of the one or more platinum group metals.

In an embodiment, the cobalt-based alloy comprises from about 18 weight percent to about 35 weight percent cobalt, from about 15 weight percent to about 25 weight percent chromium, from about 5 weight percent to about 10 weight percent molybdenum, and from about 40 weight percent to about 65 weight percent of the one or more platinum group metals.

In an embodiment, the cobalt-based alloy comprises from about 18 weight percent to about 35 weight percent cobalt, from about 15 weight percent to about 25 weight percent chromium, from about 5 weight percent to about 10 weight percent molybdenum, and from about 40 weight percent to about 65 weight percent of the one or more platinum group metals, wherein the one or more platinum group metals are selected from the group consisting of platinum and palladium.

In an embodiment, the cobalt-based alloy comprises from about 18 weight percent to about 35 weight percent cobalt, from about 15 weight percent to about 25 weight percent chromium, from about 5 weight percent to about 10 weight percent molybdenum, and from about 40 weight percent to about 65 weight percent of the one or more platinum group metals, wherein the one or more platinum group metals comprise from about 35 atomic percent to about 37 atomic percent of the cobalt-based alloy.

In an embodiment, the cobalt-based alloy is formed by providing an initial alloy comprising nickel and substituting the nickel with the one or more platinum group metals.

In an embodiment, the cobalt-based alloy is formed by providing an initial alloy comprising nickel, manganese, and iron and substituting the nickel, manganese, and iron with the one or more platinum group metals.

In an embodiment, the cobalt-based alloy is formed by providing each constituent metal in powder form, mixing the powders together, and compacting and sintering the mixture of constituent metals in powder form so as to form the cobalt-based alloy.

In an embodiment, the cobalt-based alloy is formed by providing each constituent metal in solid form or the powder form of each constituent metal and then melting the pieces or parts by arc melting, electro-slag remelting, electron beam melting, induction melting, radiant heat melting, microwave melting, or so forth.

In an embodiment, the one or more platinum group metals consists of iridium.

In an embodiment, the one or more platinum group metals consists of iridium, and the cobalt-based alloy is a ternary Co—Cr—Ir alloy consisting essentially of cobalt, chromium, and iridium in which the chromium is present from about 10 weight percent to about 25 atomic percent, and the ratio of iridium to cobalt is greater than about 1:1 on an atomic basis.

In an embodiment, the cobalt-based alloy is formed by providing an initial alloy comprising nickel and cobalt and substituting the nickel and at least a portion of the cobalt with the one or more platinum group metals.

In an embodiment, the cobalt-based alloy is formed by providing an initial alloy comprising nickel and cobalt and substituting the nickel and at least a portion of the cobalt with the one or more platinum group metals, wherein the one or more platinum group metals are selected from the group consisting of platinum and palladium.

According to another embodiment the main body includes a cobalt-based alloy that includes cobalt, chromium, and one or more so-called refractory metals (i.e., zirconium, niobium, molybdenum, hafnium, tantalum, tungsten, rhenium, silver, or gold). Silver and gold are included within this broad classification of refractory metals for sake of simplicity, as they can be used, even though their melting temperatures are significantly lower than the other members of the class. These two metals could alternatively be termed "precious metals". In one embodiment, the one or more included refractory metals substitute for nickel, such that the alloy is substantially nickel free (e.g., includes no more than about 2% nickel by weight). Another embodiment is entirely free of nickel. In addition, the alloys may include iron, although the amount of iron is limited to no more than about 20% by weight, no more than about 10% by weight, or no more than about 8% by weight. In other embodiments, the alloys are substantially iron free (e.g., no more than about 4% iron by weight). In another embodiment, iron is entirely absent.

Another embodiment of the present invention includes a method for positioning a stent in a lumen of a living being. The method comprises providing a radiopaque stent comprising a cylindrical main body that includes a cobalt-based alloy as described above. The cobalt-based alloy is deformable in a ductile manner, rendering the radiopaque stent balloon expandable on a delivery system. The stent is initially unexpanded. The stent is transported to a lesion site in the lumen wherein the stent is optionally imaged during transport. The stent is expanded to contact the lesion. The radiopaque stent is imaged during or after expanding the stent.

In an embodiment, the cobalt-based alloy may be formed beginning with a cobalt-based alloy that does not contain the platinum group metal or refractory metal, but contains another component to be partially or completely substituted (e.g., nickel) with a platinum group metal or refractory metal. All ingredients would then be melted together (e.g., arc melting, electro-slag remelting, electron beam melting, induction melting, radiant heat melting, microwave melting, or so forth) to produce an ingot which is then processed by conventional metalworking means to produce tubing or other desired forms. Additional elements such as iron, silicon, titanium, manganese and cobalt may also be substituted either partially or completely in addition to the nickel. For example, the substitution may be made by arc melting the alloy in the presence of the substituting element(s). For example, nickel initially present within such a cobalt-chromium alloy may thus be partially or completely substituted with a platinum group metal or refractory metal. In some embodiments, a portion of the cobalt may also be substituted.

In another embodiment, powdered elements of the various constituents of the revised cobalt-based alloy composition may be mixed together and then compacted and sintered so as to form the desired alloy by means of conventional powder metallurgy processing techniques.

In an embodiment, the cobalt-based alloy may include cobalt, chromium, and manganese as an austenitic stabilizer, in addition to the one or more platinum group metals, refractory metals, and/or precious metals for increased radiopacity. Such an alloy may be substantially free of nickel, may be entirely free of nickel, or at least include a reduced amount of nickel as compared to L-605 (10 weight percent Ni). The alloy may include no or limited amounts of added iron (e.g., no more than 20 weight percent iron, no more than 16 weight percent iron, no more than 4 weight percent iron, or no added iron). Manganese may be included in amounts from 1 to 25 weight percent, 1 to 17 weight percent, or 1 to 10 weight percent. Where manganese and nickel are both included, the combined weight percentages of Mn+Ni may be from 1 to 25 weight percent, 1 to 17 weight percent, or 1 to 10 weight percent. Similarly, the combined weight percentages of Mn+Ni+Fe may be from 1 to 25 weight percent, 1 to 17 weight percent, or 1 to 10 weight percent.

In an embodiment, the cobalt-based alloy includes cobalt, chromium, an austenitic stabilizer for cobalt including a combination of manganese and optionally nickel, and one or more platinum group metals, refractory metals, or precious metals. The nickel may be included at less than 5 weight percent (if at all) and the alloy may comprise only limited iron content (e.g., no more than 20 weight percent) if any iron is included at all.

In an embodiment, the cobalt-based alloy includes cobalt, chromium, an austenitic stabilizer for cobalt including a combination of manganese and nickel, the nickel content being less than that included in L-605 alloy (10 weight percent). The alloy includes one or more platinum group metals, refractory metals, or precious metals. The nickel may be included from 5 to 8 weight percent and the alloy may comprise only limited iron content (e.g., no more than 4 weight percent) if any iron is included at all. A combined weight percentage of the manganese and nickel may be from 7 weight percent to 10 weight percent.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

To further clarify the above and other advantages and features of the present disclosure, a more particular description will be rendered by references to specific embodiments thereof, which are illustrated in the appended drawings. It is appreciated that these drawings depict only typical embodiments of the invention and are therefore not to be considered limiting of its scope. The present disclosure will be described and explained with additional specificity and detail through the use of the accompanying drawings in which.

DETAILED DESCRIPTION

I. Introduction

Figure 1:
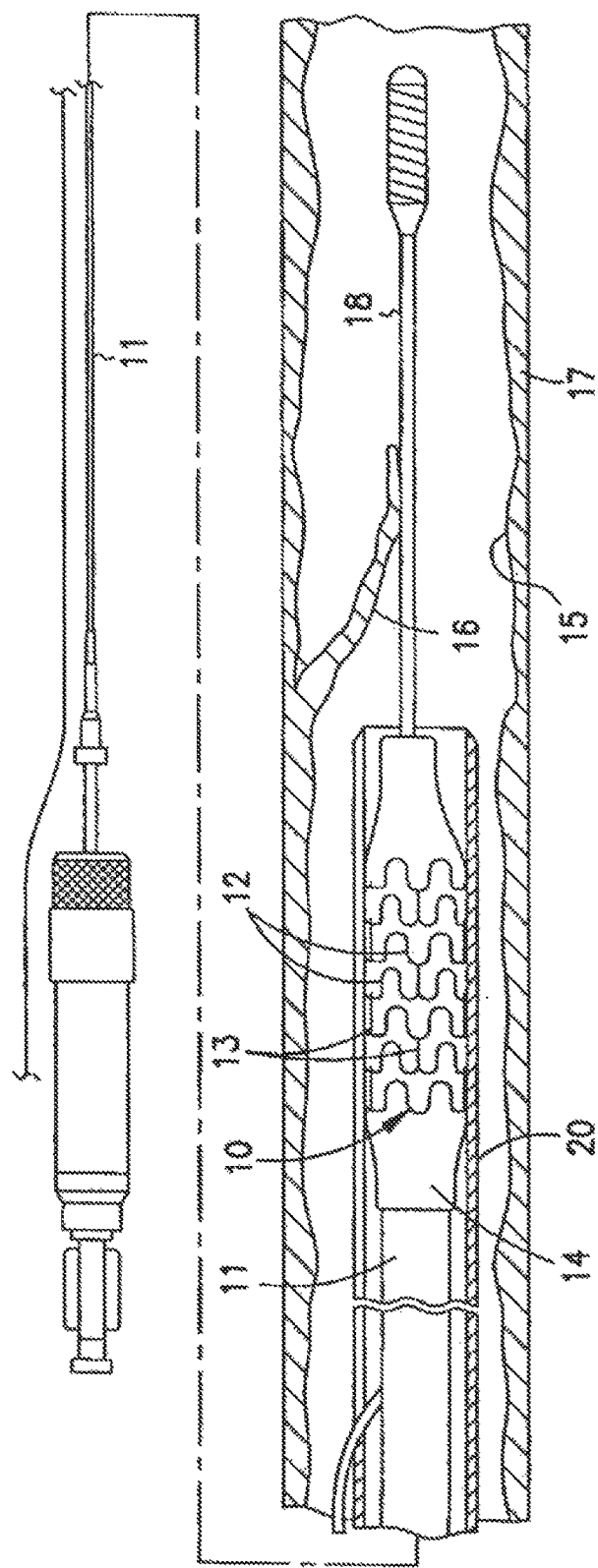
FIG. 1 is an elevational view, partially in section, of a radiopaque stent according to an embodiment of the present invention mounted on a delivery catheter and disposed within a damaged lumen.

Embodiments of the present invention are directed to radiopaque cobalt alloys, radiopaque implantable structures (e.g., stents) and related methods of manufacture and use. A radiopaque stent may include a cylindrical main body comprising a radiopaque cobalt-based alloy including cobalt, chromium, and one or more platinum group metals (i.e., one or more of platinum, palladium, ruthenium, rhodium, osmium, or iridium), refractory metals (i.e., zirconium, niobium, molybdenum, hafnium, tantalum, tungsten, rhenium, silver, or gold), or combinations thereof. Advantageously the alloys are substantially nickel free (e.g., include no more than about 2% by weight nickel, more typically no more than 1% nickel by weight). In one embodiment, the alloy is entirely free of nickel. By entirely free of nickel, it will be understood that minute trace fractions of nickel may still be present in some embodiments based on the fact that the alloy includes cobalt, and it can be very difficult, if not a practical impossibility to entirely separate trace amounts of nickel from the cobalt. In any event, where the alloy is "entirely" free of nickel, no nickel is intentionally added to the alloy.

Some patients exhibit an allergic reaction to nickel, and so providing a nickel-free alloy is advantageous as it increases the biocompatibility of the alloy. In addition, the inclusion of the nickel limits the degree of radiopacity that may be achieved. In addition, the alloy preferably does not include a large fraction of iron. For example, in one embodiment, the alloy includes no more than about 20% by weight iron, more preferably no more than about 16% by weight iron, no more than about 10% by weight iron, or no more than about 8% by weight iron. In another embodiment, iron is present, if at all, in an amount not greater than about 4% by weight, more typically not greater than about 3% by weight. In another embodiment, the alloy is iron-free. Similar to the meaning of nickel-free, the term iron-free means that no iron is intentionally added to the alloy, although trace amounts may be present as impurities carried in the other elements. Limiting the amount of iron within the alloy allows other elements to be present that provide for better radiopacity and corrosion resistance than does iron. In addition, it may reduce any magnetic characteristics of the resulting metal alloy, which may be helpful in conjunction with MRI and/or other imaging techniques.

II. Radiopaque Stent and Cobalt-Based Alloy Embodiments

According to various embodiments, the radiopaque stent is imagable during fluoroscopy. Due to the enhanced radiopacity, the entire stent is better observed by the practitioner placing the stent. The image observed by the practitioner is thus less likely to be too faint due to insufficient radiopacity or the lumen is not visible from excessive radiopacity. Because of the improved image, the stent is more easily and accurately positioned and manipulated within a lumen of a patient. Because the radiopaque composition from which the stent is formed has greater radiopacity per unit thickness than alternative alloys, the stent may also be formed at thinner thickness all the while providing a desired level of radiopacity performance. An additional advantage to the better radiopacity is the visualization of the stent and the underlying vessel during follow-up examinations by the practitioner. Because the entire stent is radiopaque, the diameter and length of the stent are readily discerned by the practitioner. Also, because the stent itself is made of the radiopaque alloy, the stent does not have problems associated with radiopaque coatings, such as cracking, separation, or corrosion. Also, because the entire stent is radiopaque, the stent does not require extra markers with their attendant issues.

The strength of the alloy material is sufficient that the stent may be manufactured with a low profile. The low profile of the disclosed cobalt-based alloy stents, coupled with its enhanced radiopacity renders the stent easily deliverable with easier observation and detection throughout its therapeutic use than stents heretofore available. A stent constructed of the specific contemplated cobalt-based alloys can be made thinner than one of stainless steel without sacrificing fluoroscopic visibility. The low profile of the disclosed cobalt-based stents renders the stent more easily deliverable with greater flexibility.

Furthermore, improved radiopacity of the low profile stent increases deliverability of the stent and offers additional performance advantages in the form of decreased fluid mechanics disturbances to blood flow and more rapid reendothelialization. Improved radiopacity assists the practitioner in placing the device precisely. Inflation of the stent is better monitored because the stent is more readily visible to the practitioner. This visibility reduces the incidence and probability of an under-deployed stent. Further, in-stent restenosis may be more accurately monitored as the stent and an injected contrast agent are able to be imaged simultaneously. Unlike some stents, the disclosed stents do not produce an image which is too bright, thereby obscuring imaging of the underlying vessel morphology.

Many cobalt-based alloys, although very strong, have insufficient ductility for use in a stent. The cobalt-based alloys described herein preferably have at least 20% or greater elongation and thereby achieve adequate stent expansion. Some of the disclosed cobalt-based alloys also include elements such as tungsten or molybdenum. These elements not only strengthen, but also contribute to the overall excellent radiopacity of the cobalt-based alloy (particularly in the case of tungsten). These elements (e.g., tungsten or molybdenum) may also improve corrosion resistance and a resistance to oxidation at high temperatures of the cobalt-based alloy.

For example, cobalt-chromium alloy L-605, covered by ASTM standard F90, includes about 15% by weight tungsten. Alloy L-605 has a minimum ultimate tensile strength of 125 ksi, a minimum yield strength of 45 ksi and a minimum total elongation of 30%. According to one embodiment of the invention, the alloy is similar to L-605, in which substantially all of the nickel of L-605 has been replaced with a platinum group metal, a refractory metal, or combinations thereof. For example, alloy L-605 contains about 10% by weight nickel. By substituting the nickel with a platinum group metal or refractory metal, the relative radiopacity of the resulting alloy is increased relative to alloy L-605, and the resulting alloy is advantageously nickel free or substantially nickel free.

Another exemplary alloy which may be similarly modified is Elgiloy, covered by ASTM standard F1058 Grade 1. Phynox is an alternative alloy composition similar to that of Elgiloy. Phynox is covered by ASTM standard F1058 Grade 2. Elgiloy is a cobalt-chromium alloy containing about 40% by weight cobalt, about 20% by weight chromium, about 16% by weight iron, about 15% by weight nickel, about 7% by weight molybdenum, and about 2% by weight manganese. Phynox is similar, but the manganese is replaced with iron. The nickel may be substituted with a platinum group metal or refractory metal so as to result in an alloy having increased relative radiopacity and that is nickel free or substantially nickel free. In another embodiment, the platinum group metal or refractory metal may also replace all or a part of the iron and/or manganese.

Another exemplary alloy which may be similarly modified is MP-35N, covered by ASTM standard F562. MP-35N is a cobalt-chromium alloy containing about 35% by weight cobalt, about 20% by weight chromium, about 35% by weight nickel, about 10% by weight molybdenum, and about 1% maximum iron. The nickel may be substituted with a platinum group metal or refractory metal so as to result in an alloy having increased relative radiopacity and that is nickel free or substantially nickel free. In another embodiment, the platinum group metal or refractory metal may replace all or a part of the iron as well.

In additional embodiments, upon completely replacing the nickel, a portion of the cobalt may also be replaced by the platinum group metal(s) or refractory metal(s), based on the overall increase in radiopacity that is desired. This substitution may be performed for any cobalt-based alloy, including those described above. To maintain a single-phase microstructure, it is suggested that the cobalt be substituted with a platinum group element or refractory metal that has substantially complete mutual solid solubility with cobalt. Furthermore, in some embodiments, some of the chromium or another element in the known alloy may also be replaced.

Atomic substitution takes an "atom for atom" approach in alloy modification by employing atomic weight. Atomic weight is commonly understood to be weight per mole of atoms. Atomic substitution maintains the stoichiometry of the original alloy when substituting, which may be an important approach when working with ordered alloys and when maintaining a particular phase structure. Atomic substitution may be more commonly understood in the art than volumetric substitution.

Volumetric substitution accounts for both the atomic radii and the crystal structure that the element naturally takes in the solid form, by employing atomic volume. Atomic volume is commonly understood to be volume per mole of atoms in the solid phase. This approach provides insight into effects on the host lattice by the substituting atom(s). This approach may allow for better retaining and understanding of the workability and mechanical strength of the modified alloy.

Substitution on a weight percent basis results in alloys that have comparatively less of the platinum group elements (or refractory elements), as all of them have greater atomic weight and density than the majority of elements being substituted for in the original cobalt-based alloys. Utilizing weight percent for substitution may be more typically employed for cobalt-based alloys where the elements have similar atomic weights, such as stainless steels, which are comprised primarily of iron, chromium and nickel.

Due to the low atomic weight of nickel compared to that of the platinum group metals (and somewhat less so as compared to the refractory metals), it will readily be realized that substituting for nickel would produce significantly different overall alloy compositions if the substitution were based on weight percentage as compared to atomic percentage. This is an important consideration with regard to radiopacity, because the attenuation of x-rays by a given material is largely dictated by the energy of the electron orbitals surrounding its atoms and their nuclei. Elements with more massive nuclei, and correspondingly higher energy orbitals, attenuate x-rays to a much greater extent than those with lighter nuclei, which explains why metals like tantalum, tungsten, platinum, and gold are inherently more radiopaque than lighter metals like chromium, iron, cobalt, and nickel. Thus, when substituting a platinum group metal (or a refractory metal) for nickel in a given alloy, the resulting impact on radiopacity is considerably greater when the nickel is replaced on an atom-for-atom basis rather than gram-for-gram. The impact of a given alloying element on many of an alloy's chemical properties, such as corrosion resistance, also depends on the atomic percentage present.

While nickel is the preferred element to be substituted by a platinum group or refractory metal for biocompatibility reasons, in some embodiments other elements in commercial cobalt-based alloys may be replaced (i.e., substituted), particularly if greater radiopacity is desired. Note that iron and manganese are minor alloying elements in L-605, iron and silicon are minor alloying elements in Elgiloy, and iron and titanium are minor alloying elements in MP-35N. These elements are not considered essential, with regard to corrosion behavior and room-temperature mechanical properties, especially if other impurities such as carbon and sulfur are held to a minimum, and therefore could be replaced by more of the platinum group metal(s) (or refractory metal(s)) and thereby simplify the overall composition while further increasing radiopacity. Should radiopacity still be insufficient after nickel and these minor alloying elements have been fully substituted, a portion of the cobalt could also be replaced by the platinum group metal(s). This strategy would more likely be applied to cobalt-based alloys that contain lesser amounts of nickel, such as L-605.

Nickel plays an important role in commercial cobalt-based alloys. As in iron-based stainless steels, nickel serves as an "austenite stabilizer" in cobalt-based alloys. That is, nickel suppresses cobalt's allotropic transformation from a face-centered-cubic ("FCC") crystal structure at high temperatures to a hexagonal-close-packed ("HCP") structure at low temperatures. In pure cobalt, this transformation naturally occurs at around 422° C. The addition of nickel significantly reduces cobalt's transformation temperature, thereby favoring the FCC structure which, in general, is a more ductile and more creep-resistant crystal structure than HCP. Therefore, when substituting nickel with another element, it is important that the replacement also serve as an austenite stabilizer.

By way of example, palladium immediately suppresses cobalt's FCC-to-HCP transformation temperature at relatively small addition levels, whereas platinum, rhodium and iridium initially raise and then ultimately lower the transformation temperature as alloying levels rise, while ruthenium and osmium continuously raise cobalt's transformation temperature as their levels rise. Similar considerations apply in the potential substitution of refractory metals for nickel. Thus, the particular platinum group and/or refractory metal(s) selected and their substitution levels are important considerations with regard to the final crystal structure(s) that will be obtained at ambient temperatures.

As explained in further detail below in conjunction with Tables 7-10 and Examples 90-132, manganese can serve to suppress cobalt's FCC-to-HCP transformation, and as such, may be included as an austenitic stabilizer.

Chromium also plays an important role in commercial cobalt-based alloys. As in iron-based stainless steels, chromium is also a powerful corrosion inhibitor in cobalt-based alloys. Corrosion and elevated-temperature oxidation behavior are substantially improved by the stable, tightly adhering chromium oxide layer that spontaneously forms when chromium containing cobalt-based alloys are exposed to air or other oxidizing environments. This layer serves to protect these alloys in a variety of otherwise corrosive environments, including saline and blood. For this reason, it is beneficial when substituting nickel and possibly other elements with platinum group and/or refractory metals that the resulting alloy composition contain sufficient chromium that adequate corrosion resistance is maintained. Iron-based austenitic stainless steels like types 304 and 316 typically contain approximately 18% by weight chromium, whereas L-605, Elgiloy, and MP-35N each contain about 20% by weight. Thus, it is not recommended that platinum group metals and/or refractory metals replace significant amounts of the chromium present in commercial cobalt-based alloys. Where additional corrosion resistance is warranted, the chromium level may be increased (e.g., to about 25% by weight).

In any case, chromium is present in sufficient amount to inhibit corrosion. Some alloy embodiments may include chromium fractions well below 20% by weight while still achieving this purpose (e.g., at least about 10% by weight, or from about 10% to about 15% by weight). Specific examples of such alloys are found in Table 5 and Examples 78-89. This may be possible particularly where the atomic percentage of chromium remains relatively high (e.g., at least about 20 atomic percent, or at least about 25 atomic percent). The weight percentages are lower in Examples 78-89 because the very dense platinum is included in high fractions.

Generally, alloys based on an L-605 alloy in which the nickel has been replaced on either an atomic or volumetric basis with a platinum group metal may include about 18 weight percent to about 50 weight percent cobalt (e.g., in one embodiment about 40 to about 50 weight percent cobalt), about 10 weight percent to about 25 weight percent chromium (e.g., in one embodiment about 15 weight percent to about 25 weight percent chromium, about 15 to about 20 weight percent chromium, or about 20 weight percent chromium), about 10 weight percent to about 15 weight percent tungsten, about 0 weight percent to about 2 weight percent manganese, about 0 weight percent to about 3 weight percent iron, and about 10 weight percent to about 65 weight percent of a platinum group metal. One embodiment may include about 10 weight percent to about 35 weight percent of a platinum group metal (i.e., platinum, palladium, ruthenium, rhodium, osmium, iridium, or combinations thereof). Examples of such materials are further described below in conjunction with Table 1 and Examples 1-12. Trace elements included within this alloy may not be shown unless they are called out for substitutional purposes.

Generally, alloys based on an ASTM F1058 alloy (e.g., Elgiloy or Phynox) in which at least the nickel has been replaced (e.g., iron and/or manganese may also be replaced) on an atomic basis with a platinum group metal may include about 22 weight percent to about 40 weight percent cobalt, about 10 weight percent to about 25 weight percent chromium (e.g., in one embodiment about 15 weight percent to about 25 weight percent chromium, about 15 to about 20 weight percent chromium, or about 20 weight percent chromium), about 4 weight percent to about 7 weight percent molybdenum, about 0 weight percent to about 2 weight percent manganese, about 0 weight percent to about 18 weight percent iron, and about 10 weight percent to about 65 weight percent of a platinum group metal (i.e., platinum, palladium, ruthenium, rhodium, osmium, iridium, or combinations thereof). One example may include about 15 weight percent to about 65 weight percent of a platinum group metal. Examples of such materials are further described below in conjunction with Table 2 and Examples 13-20. Trace elements included within this alloy may not be shown unless they are called out for substitutional purposes.

Another alloy based on an ASTM F1058 alloy could replace the nickel with a refractory metal (e.g., silver, gold, hafnium, niobium, rhenium, tantalum, molybdenum, zirconium, or combinations thereof), and include weight fractions as described above, but in which the refractory metal (rather than a platinum group metal) is included from about 10 weight percent to about 65 weight percent, or from about 15 weight percent to about 65 weight percent.

Generally, alloys based on an MP-35N alloy in which the nickel has been replaced on an atomic percentage basis by a platinum group metal may include about 18 weight percent to about 39 weight percent cobalt (e.g., one embodiment may include about 18 to about 35 weight percent cobalt), about 10 weight percent to about 25 weight percent chromium (e.g., in one embodiment about 15 weight percent to about 25 weight percent chromium, about 15 to about 20 weight percent chromium, about 10 to about 21 weight percent chromium, or about 20 weight percent chromium), about 5 weight percent to about 10 weight percent molybdenum, and about 10 weight percent to about 65 weight percent of a platinum group metal (i.e., platinum, palladium, ruthenium, rhodium, osmium, iridium, or combinations thereof). One embodiment may include about 40 to about 65 weight percent of a platinum group metal. Examples of such materials are further described below in conjunction with Table 3 and Examples 21-24. Trace elements included within this alloy may not be shown unless they are called out for substitutional purposes.

Generally, alloys based on an L-605 alloy in which the nickel has been replaced on a weight percentage basis with a refractory metal may include about 18 weight percent to about 55 weight percent cobalt (e.g., in one embodiment about 20 to about 55 weight percent cobalt), about 15 weight percent to about 25 weight percent chromium (e.g., in one embodiment about 20 weight percent chromium), about 0 weight percent to about 15 weight percent tungsten, and about 10 weight percent to about 60 weight percent of a substituting refractory metal selected from the group consisting of silver, gold, hafnium, niobium, rhenium, tantalum, molybdenum, zirconium, or combinations thereof. One embodiment may include about 10 weight percent to about 45 weight percent of the substituting refractory metal (i.e., silver, gold, hafnium, niobium, rhenium, tantalum, molybdenum, zirconium, or combinations thereof). Examples of such alloys are further described below in conjunction with Table 1 and Examples 25-28, 31-33, 36-38, 41-43, 46-47, 50-52, 55-57, 60, 65-66, and 69. Other trace elements (e.g., manganese, iron, etc.) may be present in small amounts of about 0 to about 3 percent by weight. Trace elements included within this alloy may not be shown unless they are called out for substitutional purposes.

L-605 alloy already contains about 15 weight percent tungsten. An alloy based on an L-605 alloy in which the nickel has been replaced on a weight percentage basis with the refractory metal tungsten may include about 18 weight percent to about 55 weight percent cobalt (e.g., in one embodiment about 20 to about 55 weight percent cobalt), about 15 weight percent to about 25 weight percent chromium (e.g., in one embodiment about 20 weight percent chromium), and about 25 weight percent to about 60 weight percent tungsten. One embodiment may include about 25 weight percent to about 45 weight percent of the substituting refractory metal tungsten. Examples of such tungsten alloys are further described below in conjunction with Table 1 and Examples 61-62. Other trace elements (e.g., manganese, iron, etc.) may be present in small amounts of about 0 to about 3 percent by weight.

Generally, alloys based on an MP-35N alloy in which the nickel has been replaced on a weight percentage basis by a refractory metal may include about 18 weight percent to about 39 weight percent cobalt (e.g., one embodiment may include about 20 to about 35 weight percent cobalt), about 15 weight percent to about 25 weight percent chromium (e.g., one embodiment may include about 20 weight percent chromium), about 0 weight percent to about 10 weight percent molybdenum, and about 35 weight percent to about 60 weight percent of a substituting refractory metal (i.e., silver, gold, hafnium, niobium, rhenium, tantalum, tungsten, zirconium, or combinations thereof). One embodiment may include about 35 to about 50 weight percent of a substituting refractory metal. Examples of such materials are further described below in conjunction with Table 3 and Examples 29-31, 34-36, 39-41, 44-45, 48-50, 53-55, 58-60, 63-64, and 67-69. Trace elements included within this alloy may not be shown unless they are called out for substitutional purposes.

MP-35N alloy already contains about 10 weight percent molybdenum. An alloy based on an MP-35N alloy in which the nickel has been replaced on a weight percentage basis with the refractory metal molybdenum may include about 18 weight percent to about 39 weight percent cobalt (e.g., in one embodiment about 20 to about 35 weight percent cobalt), about 15 weight percent to about 25 weight percent chromium (e.g., in one embodiment about 20 weight percent chromium), and about 45 weight percent to about 60 weight percent molybdenum. Examples of such molybdenum alloys are further described below in conjunction with Table 1 and Examples 44-45. Other trace elements (e.g., manganese, iron, etc.) may be present in small amounts of about 0 to about 3 percent by weight.

One type of radiopaque stent design embodiment is a high precision patterned cylindrical device. This device is illustrated generally at 10 in FIG. 1. The stent 10 typically comprises a plurality of radially expanded cylindrical elements 12 disposed generally coaxially and interconnected by elements 13 disposed between adjacent cylindrical elements.

For some embodiments, the stent 10 is expanded by a delivery catheter 11. The delivery catheter 11 has an expandable portion or a balloon 14 for expanding of the stent 10 within an artery 15. The delivery catheter 11 onto which the stent 10 is mounted may be similar to a conventional balloon dilation catheter used for angioplasty procedures. The artery 15, as shown in FIG. 1, has a dissected lining 16 which has occluded a portion of the arterial passageway.

Each radially expandable cylindrical element 12 of the radiopaque stent 10 may be independently expandable. Therefore, the balloon 14 may be provided with an inflated shape other than cylindrical, e.g., tapered, to facilitate implantation of the stent 10 in a variety of body lumen shapes.

Figure 2:
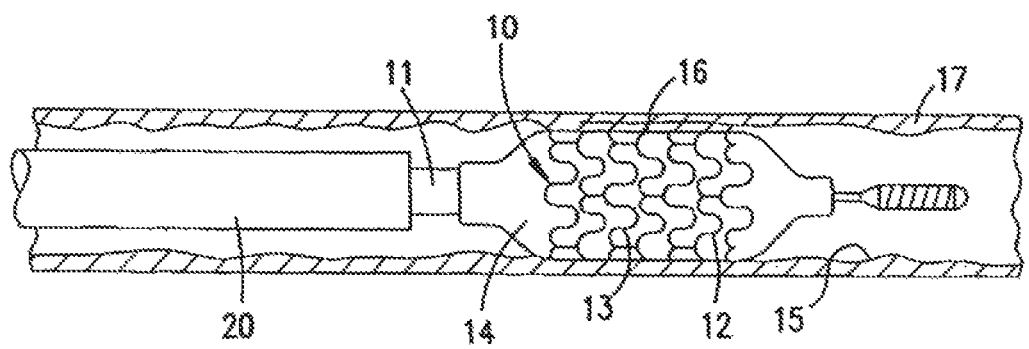
FIG. 2 is an elevational view, partially in section, showing the radiopaque stent of FIG. 1 within a damaged lumen.

The delivery of the radiopaque stent 10 is accomplished by mounting the stent 10 onto the inflatable balloon 14 on the distal extremity of the delivery catheter 11. The catheter-stent assembly is introduced within the patient's vasculature using conventional techniques through a guiding catheter which is not shown. A guidewire 18 is disposed across the damaged arterial section and then the catheter-stent assembly is advanced over a guidewire 18 within the artery 15 until the stent 10 is directly under detached lining 16 of the damaged arterial section. The balloon 14 of the catheter is expanded, expanding the stent 10 against the artery 15, which is illustrated in FIG. 2. While not shown in the drawing, the artery 15 may preferably be expanded slightly by the expansion of the stent 10 to seat or otherwise fix the stent 10 to prevent movement. In some circumstances during the treatment of a stenotic portion of an artery, the artery may have to be expanded considerably in order to facilitate passage of blood or other fluid therethrough. This expansion is easily observable by the practitioner with the disclosed radiopaque stents.

Figure 3:
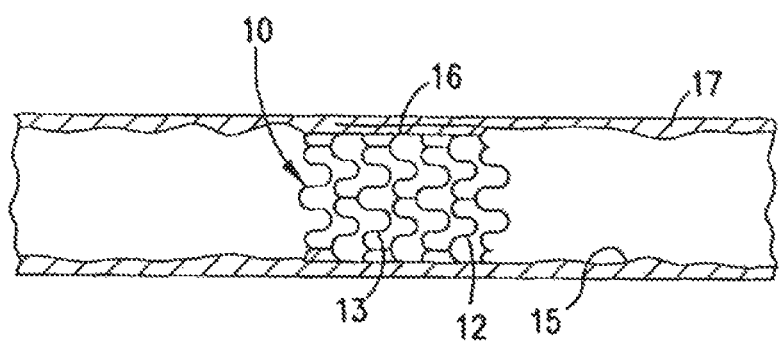
FIG. 3 is an elevational view, partially in section, showing the radiopaque stent of FIG. 1 expanded within the lumen after withdrawal of the delivery catheter.

The stent 10 serves to hold open the artery 15 after the catheter 11 is withdrawn, as illustrated in FIG. 3. Due to the formation of the stent 10 from the elongated tubular member, the undulating component of the cylindrical elements of the stent 10 is relatively flat in transverse cross section so that when the stent is expanded, the cylindrical elements are pressed into the wall of the artery 15 and as a result do not interfere with the blood flow through the artery 15. The cylindrical elements 12 of the stent 10 which are pressed into the wall of the artery 15 are eventually covered with endothelial cell growth which further minimizes blood flow interference. The undulating pattern of the cylindrical sections 12 provides good characteristics to prevent stent movement within the artery. Furthermore, the closely spaced cylindrical elements at regular intervals provide uniform support for the wall of the artery 15, and consequently are well adapted to tack up and hold in place small flaps or dissections in the wall of the artery 15 as illustrated in FIGS. 2-3. The undulating pattern of the radiopaque stent is readily discernable to the practitioner performing the procedure.

Additional details of exemplary stents are disclosed in U.S. Pat. No. 7,250,058, incorporated herein by reference in its entirety.

TABLE 1

ASTM F90 L-605 Alloy

| Element | Weight Percent | Atomic Percent | Volume Percent |
|---|---|---|---|
| Cobalt | 53.4 | 53.9 | 51.6 |
| Chromium | 20 | 24.4 | 25.2 |
| Tungsten | 15 | 5.2 | 7.1 |
| Nickel | 10 | 10.8 | 10.2 |
| Manganese (maximum) | 1.5 | 2.3 | 2.4 |
| Iron (maximum) | 0.1 | 3.4 | 3.5 |

Examples 1-12 below are based on the nominal compositions of the ASTM F90 L-605 Alloy of Table 1 in which only the nickel has been replaced on an atomic substitution basis or a volumetric substitution basis with a platinum group metal. Trace elements such as beryllium, boron, carbon, phosphorus, silicon, and sulfur are not listed.

Example 1—ASTM F90 L-605 Alloy with Atomic Substitution of Nickel with Platinum

| Element | Atomic Percent | Weight Percent |
|---|---|---|
| Cobalt | 53.9 | 40.6 |
| Chromium | 24.4 | 16.2 |
| Tungsten | 5.2 | 12.2 |
| Platinum | 10.8 | 27.0 |
| Manganese (maximum) | 2.3 | 1.6 |
| Iron (maximum) | 3.4 | 2.4 |

Example 2—ASTM F90 L-605 Alloy with Volumetric Substitution of Nickel with Platinum

| Element | Weight Percent | Volume Percent |
|---|---|---|
| Cobalt | 43.8 | 51.6 |
| Chromium | 17.5 | 25.2 |
| Tungsten | 13.2 | 7.1 |
| Platinum | 21.1 | 10.2 |
| Manganese (maximum) | 1.8 | 2.4 |
| Iron (maximum) | 2.6 | 3.5 |

Example 3—ASTM F90 L-605 Alloy with Atomic Substitution of Nickel with Palladium

| Element | Atomic Percent | Weight Percent |
|---|---|---|
| Cobalt | 53.9 | 46.2 |
| Chromium | 24.4 | 18.5 |
| Tungsten | 5.2 | 13.9 |
| Palladium | 10.8 | 16.8 |
| Manganese (maximum) | 2.3 | 1.8 |
| Iron (maximum) | 3.4 | 2.8 |

Example 4—ASTM F90 L-605 Alloy with Volumetric Substitution of Nickel with Palladium

| Element | Volume Percent | Weight Percent |
| --- | --- | --- |
| Cobalt | 51.6 | 48.3 |
| Chromium | 25.2 | 19.3 |
| Tungsten | 7.1 | 14.4 |
| Palladium | 10.2 | 13.1 |
| Manganese (maximum) | 2.4 | 2 |
| Iron (maximum) | 3.5 | 2.9 |

Example 5—ASTM F90 L-605 Alloy with Atomic Substitution of Nickel with Rhodium

| Element | Atomic Percent | Weight Percent |
| --- | --- | --- |
| Cobalt | 53.9 | 46.5 |
| Chromium | 24.4 | 18.6 |
| Tungsten | 5.2 | 13.9 |
| Rhodium | 10.8 | 16.3 |
| Manganese (maximum) | 2.3 | 1.9 |
| Iron (maximum) | 3.4 | 2.8 |

Example 6—ASTM F90 L-605 Alloy with Volumetric Substitution of Nickel with Rhodium

| Element | Volume Percent | Weight Percent |
| --- | --- | --- |
| Cobalt | 51.6 | 48.1 |
| Chromium | 25.2 | 19.2 |
| Tungsten | 7.1 | 14.4 |
| Rhodium | 10.2 | 13.4 |
| Manganese (maximum) | 2.4 | 2 |
| Iron (maximum) | 3.5 | 2.9 |

Example 7—ASTM F90 L-605 Alloy with Atomic Substitution of Nickel with Iridium

| Element | Atomic Percent | Weight Percent |
| --- | --- | --- |
| Cobalt | 53.9 | 40.7 |
| Chromium | 24.4 | 16.3 |
| Tungsten | 5.2 | 12.3 |
| Iridium | 10.8 | 26.7 |
| Manganese (maximum) | 2.3 | 1.6 |
| Iron (maximum) | 3.4 | 2.4 |

Example 8—ASTM F90 L-605 Alloy with Volumetric Substitution of Nickel with Iridium

| Element | Volume Percent | Weight Percent |
| --- | --- | --- |
| Cobalt | 51.6 | 43.4 |
| Chromium | 25.2 | 17.4 |
| Tungsten | 7.1 | 13 |
| Iridium | 10.2 | 21.9 |
| Manganese (maximum) | 2.4 | 1.7 |
| Iron (maximum) | 3.5 | 2.6 |

Example 9—ASTM F90 L-605 Alloy with Atomic Substitution of Nickel with Ruthenium

| Element | Atomic Percent | Weight Percent |
| --- | --- | --- |
| Cobalt | 53.9 | 46.6 |
| Chromium | 24.4 | 18.7 |
| Tungsten | 5.2 | 14.0 |
| Ruthenium | 10.8 | 16.1 |
| Manganese (maximum) | 2.3 | 1.9 |
| Iron (maximum) | 3.4 | 2.8 |

Example 10—ASTM F90 L-605 Alloy with Volumetric Substitution of Nickel with Ruthenium

| Element | Volume Percent | Weight Percent |
| --- | --- | --- |
| Cobalt | 51.6 | 48.2 |
| Chromium | 25.2 | 19.3 |
| Tungsten | 7.1 | 14.5 |
| Ruthenium | 10.2 | 13.2 |
| Manganese (maximum) | 2.4 | 1.9 |
| Iron (maximum) | 3.5 | 2.9 |

Example 11—ASTM F90 L-605 Alloy with Atomic Substitution of Nickel with Osmium

| Element | Atomic Percent | Weight Percent |
| --- | --- | --- |
| Cobalt | 53.9 | 40.8 |
| Chromium | 24.4 | 16.3 |
| Tungsten | 5.2 | 12.3 |
| Osmium | 10.8 | 26.5 |
| Manganese (maximum) | 2.3 | 1.6 |
| Iron (maximum) | 3.4 | 2.5 |

Example 12—ASTM F90 L-605 Alloy with Volumetric Substitution of Nickel with Osmium

| Element | Volume Percent | Weight Percent |
| --- | --- | --- |
| Cobalt | 51.6 | 43.3 |
| Chromium | 25.2 | 17.3 |
| Tungsten | 7.1 | 13.0 |
| Osmium | 10.2 | 22.0 |
| Manganese (maximum) | 2.4 | 1.7 |
| Iron (maximum) | 3.5 | 2.6 |

Although Examples 1-12 illustrate complete substitution of the nickel with a platinum group metal, it will be understood that in other embodiments, a small fraction (e.g., about 2% by weight or less) of nickel may remain within the modified alloy. Platinum or palladium substitution is particularly preferred, as these are Group 10 elements, as is nickel. As such, these substitutions would be expected to be the most metallurgically neutral and compatible so as to maintain the strength, ductility, and microstructural integrity (e.g., avoiding phase separations) of the resulting alloy. Group 9 elements (i.e., rhodium or iridium) and Group 8 elements (ruthenium or osmium) may be less likely to substitute metallurgically neutrally for nickel. For example, ruthenium and osmium may decrease the ductility of the alloy. Thus, while such alloys are within the scope of the present disclosure, the Group 9 elements may be more preferred and the Group 10 elements may be most preferred. In another embodiment, one or more Group 11 elements (i.e., silver or gold) may be substituted for the nickel. In addition, although described as substituting a single platinum group metal for the nickel, it will be understood that combinations of two or more platinum group metals (e.g., platinum and palladium) may be used.

Further examples may be envisioned with the ASTM F90 L-605 alloy where the nickel, iron, and manganese have been replaced either completely or partially with palladium, platinum, and/or other Group 8, 9, 10, or 11 elements prior to melting, either singly or in combination with one another. Further examples may be envisioned where at least a portion of the cobalt is replaced by one or more elements from groups 8, 9, 10, or 11 of the periodic table.

TABLE 2

ASTM F1058 Alloy

| Element | Weight Percent | Atomic Percent | Volume Percent |
|---|---|---|---|
| Cobalt | 40 | 39.6 | 37.9 |
| Chromium | 20 | 22.4 | 23.2 |
| Iron | 16 | 16.7 | 16.9 |
| Manganese | 2 | 2.1 | 2.2 |
| Molybdenum | 7 | 4.3 | 5.7 |
| Nickel | 15 | 14.9 | 14.1 |

As with Examples 1-12, Examples 13-16 below based on the F1058 Alloy of Table 2 are representative examples in which the nickel has been replaced either volumetrically-based or atomically-based with palladium or platinum. As with the ASTM F90 L-605 alloy, substitutions may occur from Group 8, 9, 10, and/or 11 elements. Trace metal elements such as beryllium, boron, carbon, phosphorus, silicon, and sulfur are not listed.

Example 13—ASTM F1058 Alloy with Atomic Substitution of Nickel with Platinum

| Element | Weight Percent | Atomic Percent |
|---|---|---|
| Cobalt | 29.7 | 39.6 |
| Chromium | 14.8 | 22.4 |
| Iron | 11.9 | 16.7 |
| Manganese | 1.5 | 2.1 |
| Molybdenum | 5.2 | 4.3 |
| Platinum | 37.0 | 14.9 |

Example 14—ASTM F1058 Alloy with Volumetric Substitution of Nickel with Platinum

| Element | Weight Percent | Volume Percent |
|---|---|---|
| Cobalt | 33 | 37.9 |
| Chromium | 16.5 | 23.2 |
| Iron | 13.2 | 16.9 |
| Manganese | 1.7 | 2.2 |
| Molybdenum | 5.8 | 5.7 |
| Platinum | 29.8 | 14.1 |

Example 15—ASTM F1058 Alloy with Atomic Substitution of Nickel with Palladium

| Element | Weight Percent | Atomic Percent |
|---|---|---|
| Cobalt | 35.7 | 39.6 |
| Chromium | 17.8 | 22.4 |
| Iron | 14.2 | 16.7 |
| Manganese | 1.8 | 2.1 |
| Molybdenum | 6.3 | 4.3 |
| Palladium | 24.2 | 14.9 |

Example 16—ASTM F1058 Alloy with Volumetric Substitution of Nickel with Palladium

| Element | Weight Percent | Volume Percent |
|---|---|---|
| Cobalt | 38.0 | 37.9 |
| Chromium | 19.0 | 23.2 |
| Iron | 15.3 | 16.9 |
| Manganese | 1.9 | 2.2 |
| Molybdenum | 6.7 | 5.7 |
| Palladium | 19.1 | 14.1 |

Examples 17-20 below are based on the ASTM F1058 Alloy of Table 2 in which the nickel, iron, and manganese have been replaced with palladium or platinum on either an atomic or volumetric basis. These examples may be further extended to substitution with Group 8, 9, 10, and/or 11 elements. Even further examples may be envisioned where at least part of the cobalt is substituted by one or more elements from groups 8, 9, 10, and/or 11 of the periodic table.

Example 17—ASTM F1058 Alloy with Atomic Substitution of Nickel, Iron, and Manganese with Platinum

| Element | Weight Percent | Atomic Percent |
|---|---|---|
| Cobalt | 22.3 | 39.6 |
| Chromium | 11.1 | 22.4 |
| Molybdenum | 3.9 | 4.3 |
| Platinum | 62.7 | 33.7 |

Example 18—ASTM F1058 Alloy with Volumetric Substitution of Nickel, Iron, and Manganese with Platinum

| Element | Weight Percent | Volume Percent |
| --- | --- | --- |
| Cobalt | 26.2 | 37.9 |
| Chromium | 13.1 | 23.2 |
| Molybdenum | 4.6 | 5.7 |
| Platinum | 56.1 | 33.2 |

Example 19—ASTM F1058 Alloy with Atomic Substitution of Nickel, Iron, and Manganese with Palladium

| Element | Weight Percent | Atomic Percent |
| --- | --- | --- |
| Cobalt | 31.1 | 39.6 |
| Chromium | 15.5 | 22.4 |
| Molybdenum | 5.5 | 4.3 |
| Palladium | 47.9 | 33.7 |

Example 20—ASTM F1058 Alloy with Volumetric Substitution of Nickel, Iron, and Manganese with Palladium

| Element | Weight Percent | Volume Percent |
| --- | --- | --- |
| Cobalt | 34.9 | 37.9 |
| Chromium | 17.4 | 23.2 |
| Molybdenum | 6.1 | 5.7 |
| Palladium | 41.6 | 33.2 |

TABLE 3

| ASTM F562 MP-35N Alloy | | | |
| --- | --- | --- | --- |
| Element | Weight Percent | Atomic Percent | Volume Percent |
| Chromium | 20 | 22.9 | 23.8 |
| Nickel | 35 | 35.5 | 33.7 |
| Molybdenum | 10 | 6.2 | 8.4 |
| Cobalt | 35 | 35.4 | 34.1 |

Examples 21-24 below are based on the MP-35N Alloy of Table 3 in which the nickel, as well as iron and titanium (present in MP-35N in small amounts) have been replaced with palladium or platinum on an atomic or volumetric basis. Trace elements such as beryllium, boron, carbon, iron, manganese, phosphorus, silicon, sulfur, and titanium are not listed. Further examples are envisioned where elements from groups 8, 9, 10, and/or 11 of the periodic table may be substituted for only the nickel, or also for at least some of the cobalt.

Example 21—ASTM F562 Alloy with Atomic Substitution of Nickel, Iron, and Titanium with Platinum

| Element | Weight Percent | Atomic Percent |
| --- | --- | --- |
| Chromium | 11 | 22.9 |
| Platinum | 64.2 | 35.5 |
| Molybdenum | 5.5 | 6.2 |
| Cobalt | 19.3 | 35.4 |

Example 22—ASTM F562 Alloy with Volumetric Substitution of Nickel, Iron, and Titanium with Platinum

| Element | Weight Percent | Volume Percent |
| --- | --- | --- |
| Chromium | 13.4 | 23.8 |
| Platinum | 56.5 | 33.7 |
| Molybdenum | 6.7 | 8.4 |
| Cobalt | 23.4 | 34.1 |

Example 23—ASTM F562 Alloy with Atomic Substitution of Nickel, Iron, and Titanium with Palladium

| Element | Weight Percent | Atomic Percent |
| --- | --- | --- |
| Chromium | 15.6 | 22.9 |
| Palladium | 49.4 | 35.5 |
| Molybdenum | 7.8 | 6.2 |
| Cobalt | 27.2 | 35.4 |

Example 24—ASTM F562 Alloy with Volumetric Substitution of Nickel, Iron, and Titanium with Palladium

| Element | Weight Percent | Volume Percent |
| --- | --- | --- |
| Chromium | 17.8 | 23.8 |
| Palladium | 42.1 | 33.7 |
| Molybdenum | 8.9 | 8.4 |
| Cobalt | 31.2 | 34.1 |

Relative radiopacity (RR) is a comparative measurement useful in comparing the relative radiopacity of various alloy materials. The higher the RR value, the greater the material's radiopacity. For example, 316L stainless steel has a RR value of about 2.5 barnes/cc. The RR values for Examples 1-24, as well as the materials in Tables 1-3 are shown in Table 4 below. As can be seen, the presently disclosed alloys exhibit significantly higher relative radiopacity values than L-605, Elgiloy, or MP-35N alloys. For further comparison purposes, ASTM F138 316L stainless steel has a relative radiopacity of 2.5 barnes/cc.

TABLE 4

Relative Radiopacities

| Example | Relative Radiopacity (barnes/cc) |
|---|---|
| Table 1 (ASTM F90 L-605 Alloy) | 3.6 |
| Table 2 (ASTM F1058 Elgiloy Alloy) | 3.1 |
| Table 3 (ASTM F562 MP-35N Alloy) | 3.5 |
| Example 1 | 6.2 |
| Example 2 | 5.5 |
| Example 3 | 5.3 |
| Example 4 | 4.9 |
| Example 5 | 5.2 |
| Example 6 | 4.9 |
| Example 7 | 6.1 |
| Example 8 | 5.6 |
| Example 9 | 5.0 |
| Example 10 | 4.8 |
| Example 11 | 5.9 |
| Example 12 | 5.4 |
| Example 13 | 6.5 |
| Example 14 | 5.7 |
| Example 15 | 5.4 |
| Example 16 | 4.9 |
| Example 17 | 10.7 |
| Example 18 | 9.5 |
| Example 19 | 8.3 |
| Example 20 | 7.5 |
| Example 21 | 11.1 |
| Example 22 | 9.8 |
| Example 23 | 8.7 |
| Example 24 | 7.8 |

In one embodiment, any of the contemplated cobalt-based alloys may be formed by beginning with a cobalt-based alloy that does not contain the platinum group metal (e.g., L-605, Elgiloy, Phynox, or MP-35N), but contains another component (e.g., nickel) to be partially or completely substituted with the platinum group metal. The substitution may be made by arc or otherwise melting the alloy in the presence of the substituting element(s) or by combining material constituents and then melting. The material constituents may be provided as solid pieces of constituent elements, powder compacts, loose powders, etc. Nickel initially present within such a cobalt-based alloy may thus be partially or completely substituted with a platinum group metal prior to melting (e.g., rather than including nickel, one would include the substituted element). All ingredients would then be melted together to produce an ingot which is then processed by conventional metalworking techniques to produce tubing or other desired forms. The above examples illustrate final compositions for complete substitution of the nickel, but should not be construed as the sole embodiments of the invention.

In another embodiment, powdered elements of the various constituents of the alloy may be mixed together and then compacted and sintered so as to form the desired alloy by means of conventional powder metallurgy processing techniques. Other suitable alloy forming techniques may be apparent to those of skill in the art in light of the present disclosure.

As is apparent from the various examples, the alloys may be patterned after an existing alloy (e.g., ASTM F90 L-605, ASTM F1058 Elgiloy or Phynox, or ASTM F562 MP-35N) in which at least the nickel and optionally the iron, manganese and/or other constituents have been substituted with a platinum group metal. The substitution may proceed so as to maintain the atomic percentage of the original composition, or alternatively, the volume percentage of the original composition. Another embodiment may include weight percentage substitution with the platinum group metal.

As described above, according to an alternative embodiment, the alloys may be similar to those described above in which at least the nickel has been substituted with a platinum group metal, but in which the substituting metal is a refractory metal selected from the group consisting of silver, gold, hafnium, niobium, rhenium, tantalum, molybdenum, tungsten, zirconium, or combinations thereof. It is also conceivable that the substituting elements may be a combination of platinum group metals and refractory metals.

As described above, substitution may be on an atomic basis, a volumetric basis, or a weight basis. Examples 25-69 below are based on weight percentage substitution of at least the nickel of an L-605 alloy and an MP-35N alloy. It will be understood that additional examples may substitute at least the nickel (and preferably at least some of the iron) of other cobalt-chromium alloys such as Elgiloy or Phynox. Additionally, it will be understood that substitution may alternatively proceed on an atomic or volumetric basis.

In order to better understand Examples 25-69, the various binary phase diagrams of the included elements will be discussed.

When considering the cobalt-chromium alloy systems from the perspective of elimination of nickel from the alloys, substitution of another element for the nickel in the alloy is a natural approach. When considering which elements to utilize for substitution, the desired end goals come into play. The goal of such substitution is to create an alloy that has a greater radiopacity than the unmodified alloy (e.g., L-605 or MP-35N). In order to create an alloy with greater radiopacity, one or more elements of higher atomic weight and greater relative radiopacity (RR) need to be utilized.

In reviewing the periodic table of the elements, and the binary phase diagrams for the heavier transition metal and other precious metal elements in the periodic table, a number of elements stand out as appropriate for the substitution of nickel. Further substitution for some of the cobalt in the alloy(s) is possible with the desire for even better radiopacity of the alloy compared to L-605 and MP-35N. These elements include refractory metal elements such as Zr, Nb, Mo, Hf, Ta, W, and Re, and precious metal elements such as Ag and Au (which are herein grouped with the refractory elements for sake of simplicity).

To understand the reasoning behind these selections, the phase diagrams for the L-605 CoCr (Co-20Cr-15W-10Ni) and MP-35N (35Co-35Ni-20Cr-10Mo) alloys are first discussed below. When reviewing these phase diagrams they appear complex. The following points, however, work in favor of having alloys that have properties that allow them to be mechanically worked into a variety of useful forms, including stent tubing. For ease of understanding, elements less than 5 weight percent (e.g., manganese, iron, etc.) are ignored in this analysis, and presumed to be part of the cobalt concentration.

For the most part, the discussion will be limited to phases that are predicted to exist at the temperatures of interest, which include body temperature and room temperature. Also, when discussing compositions, all are considered "relative" compositions to relate them to the binary phase diagram unless otherwise indicated. For example, an alloy including 55 weight percent Co and 20 weight percent Cr ("55Co-20Cr") would translate to a relative composition of 73Co-27Cr in weight percent. All substituted alloy compositions below are discussed weight percent, unless otherwise indicated. Phase structures discussed include body centered cubic (BCC), face centered cubic (FCC), hexagonal close packed (HCP), orthorhombic, rhombohedral, tetragonal, and body centered tetragonal (BCT).

Figure 4A:
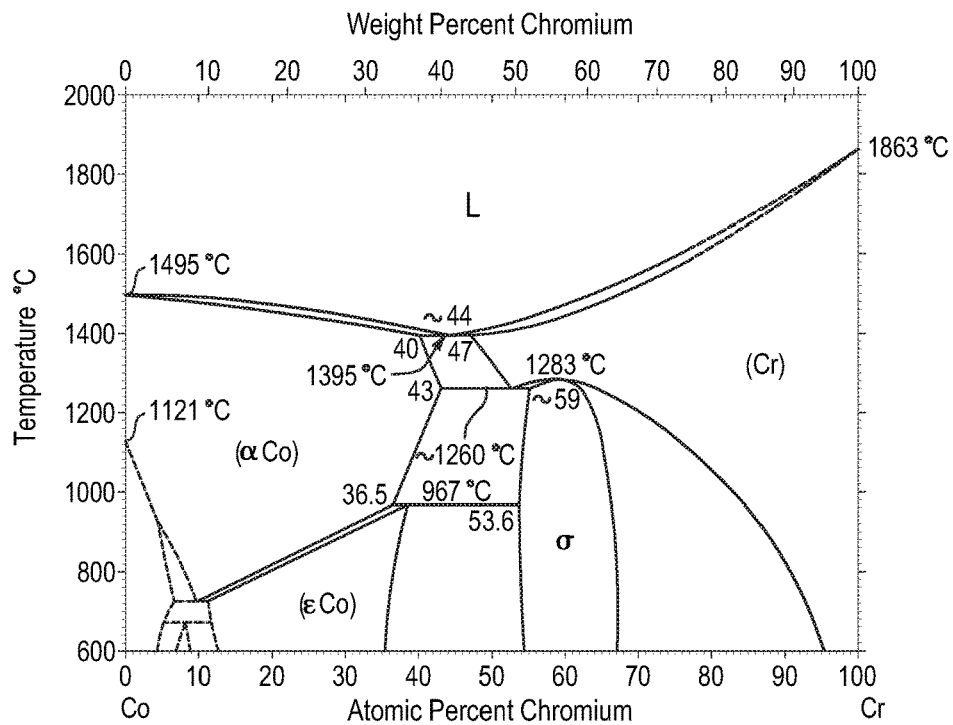
FIGS. 4A and 4B show a phase diagram for cobalt-chromium.
Figure 4B:
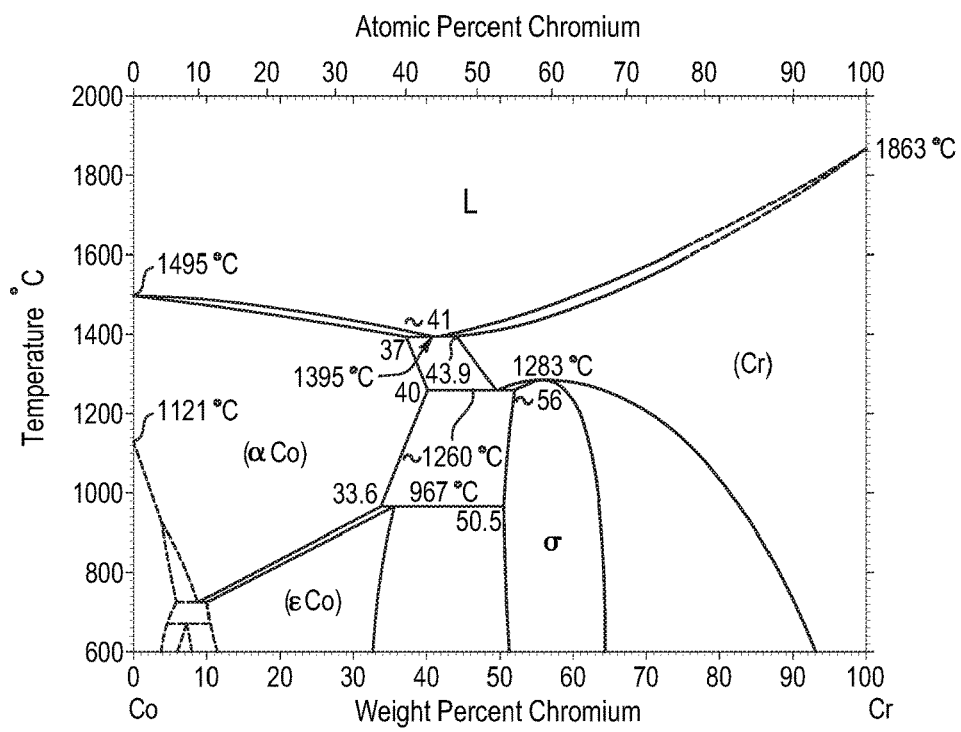
Figure 5A:
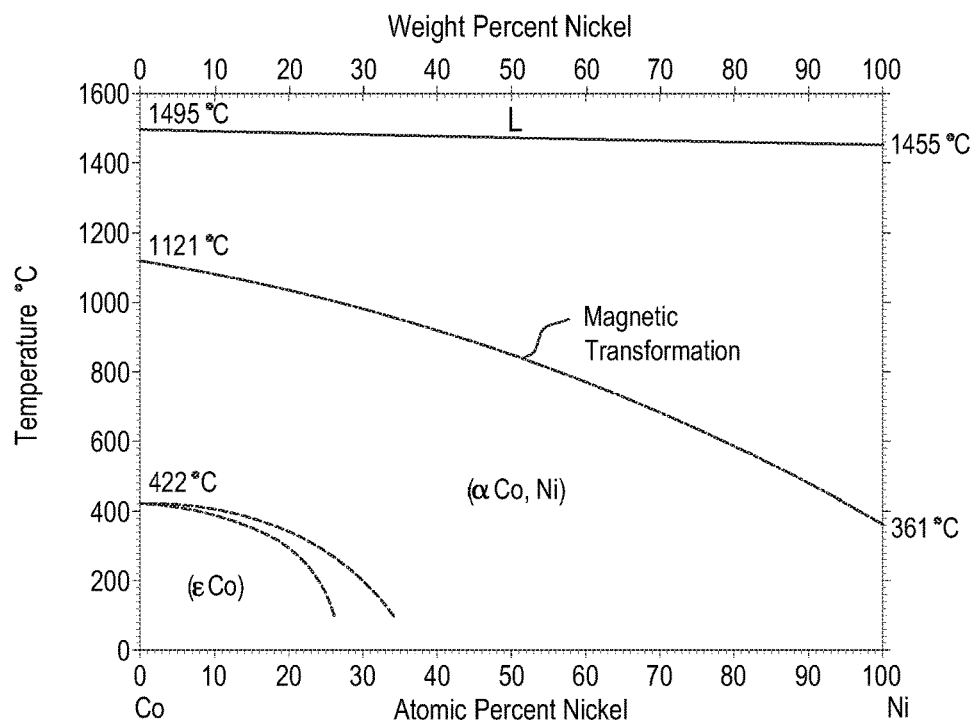
FIGS. 5A and 5B show a phase diagram for cobalt-nickel.
Figure 5B:
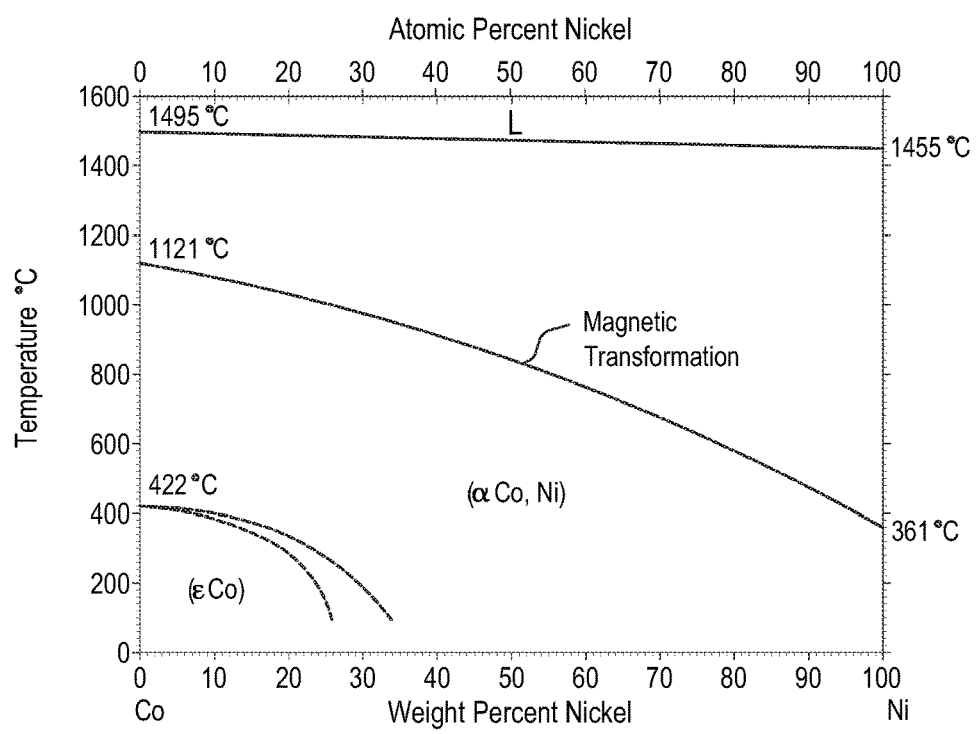
Figure 6A:
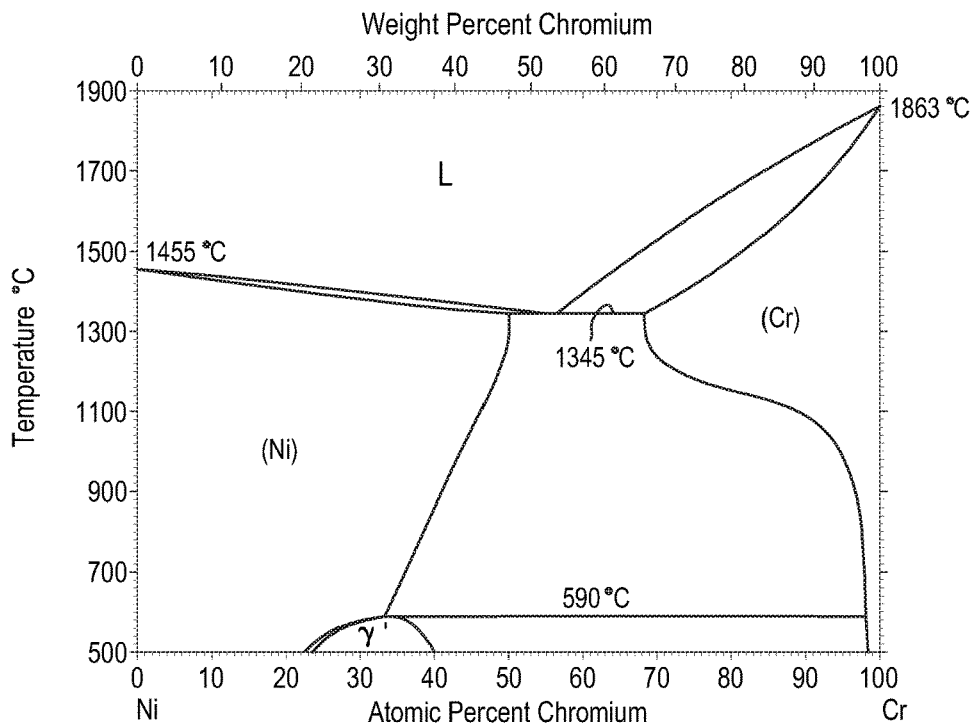
FIGS. 6A and 6B show a phase diagram for nickel-chromium.
Figure 6B:
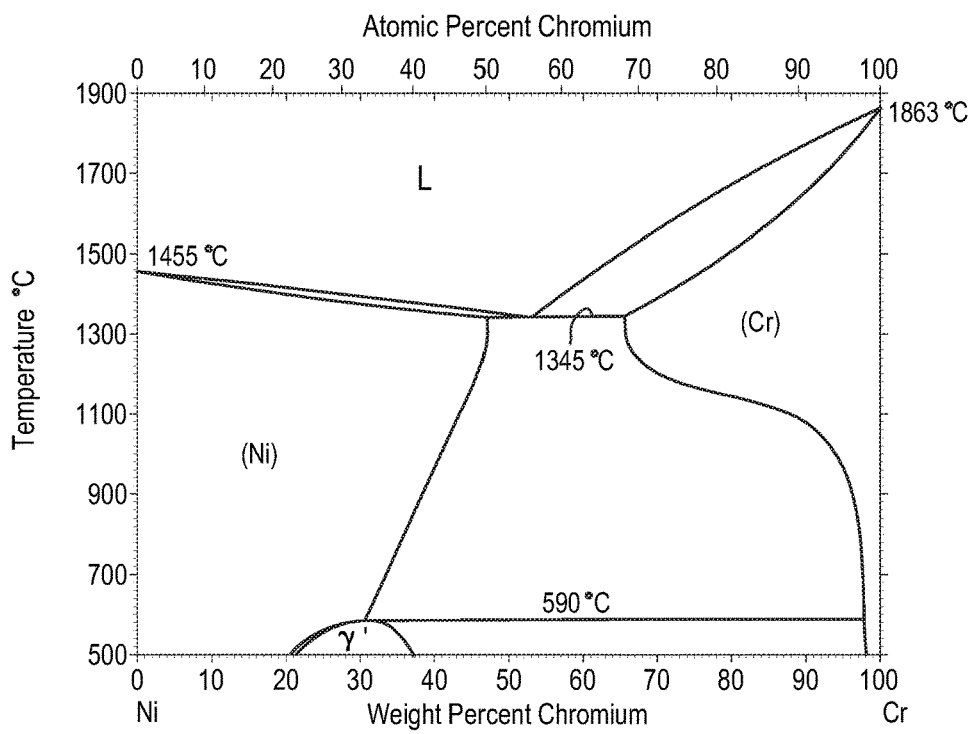
Figure 7A:
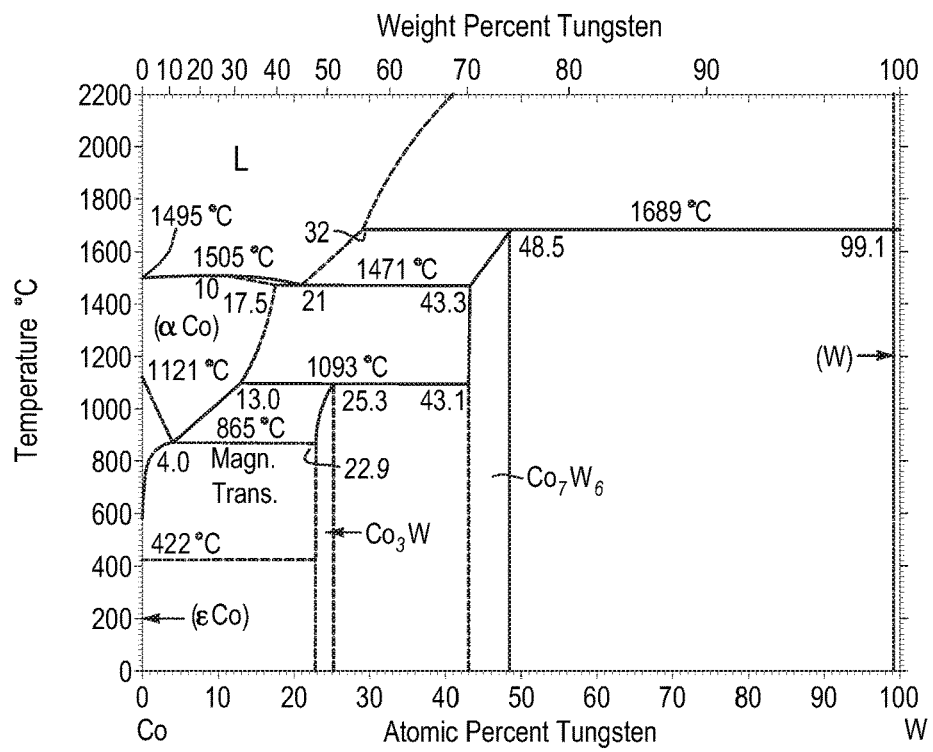
FIGS. 7A and 7B show a phase diagram for cobalt-tungsten.
Figure 7B:
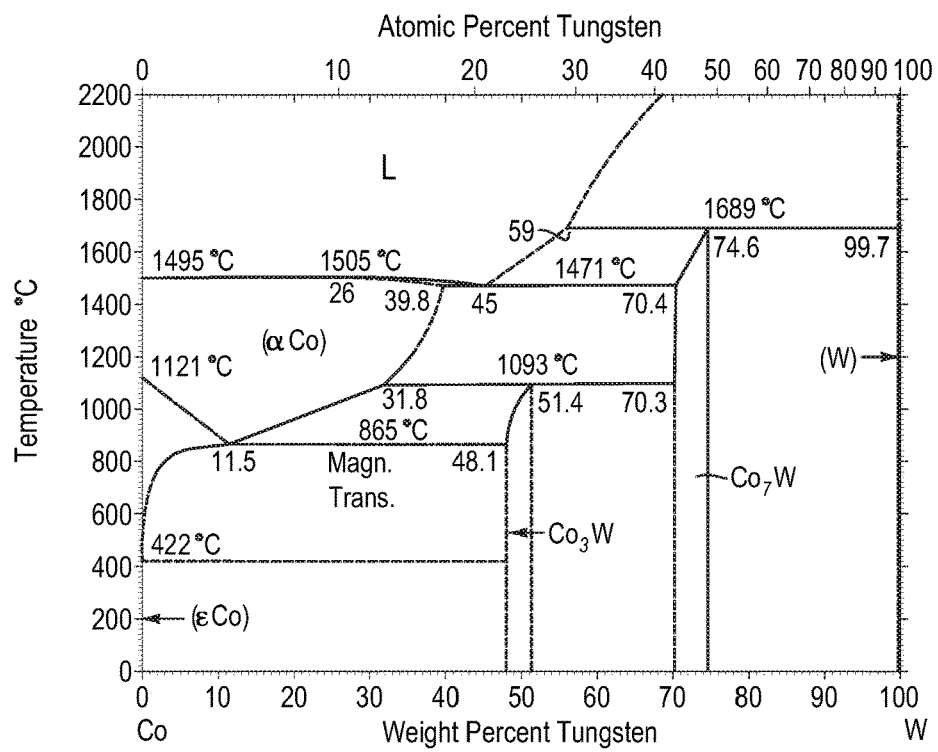
Figure 8A:
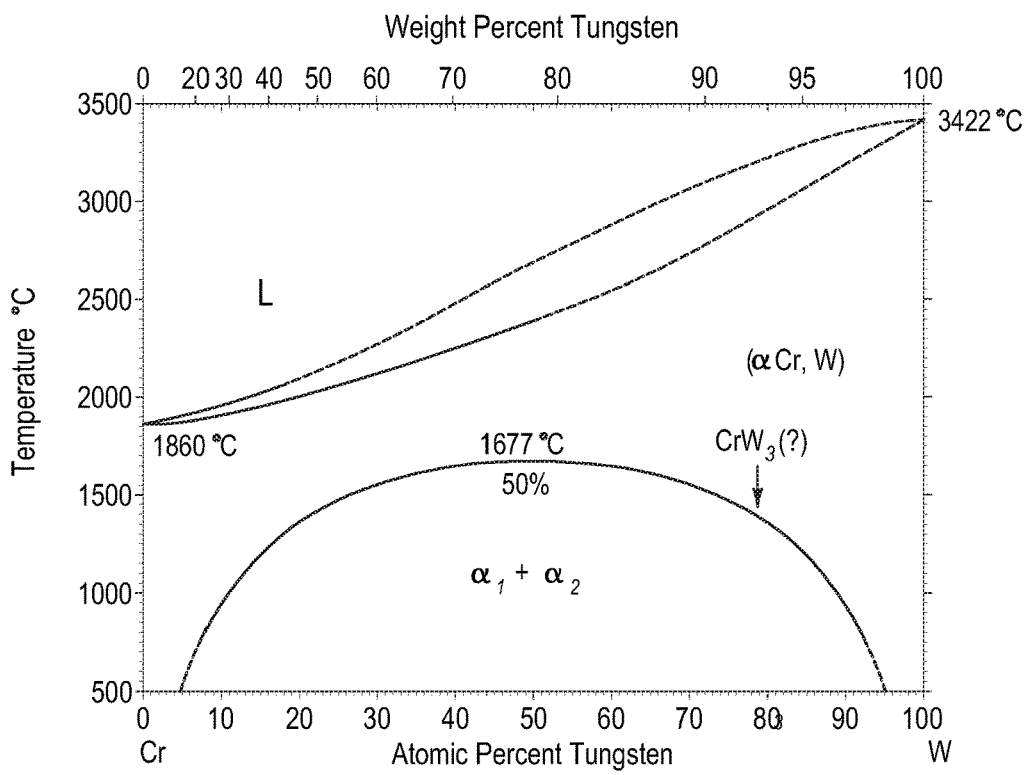
FIGS. 8A and 8B show a phase diagram for chromium-tungsten.
Figure 8B:
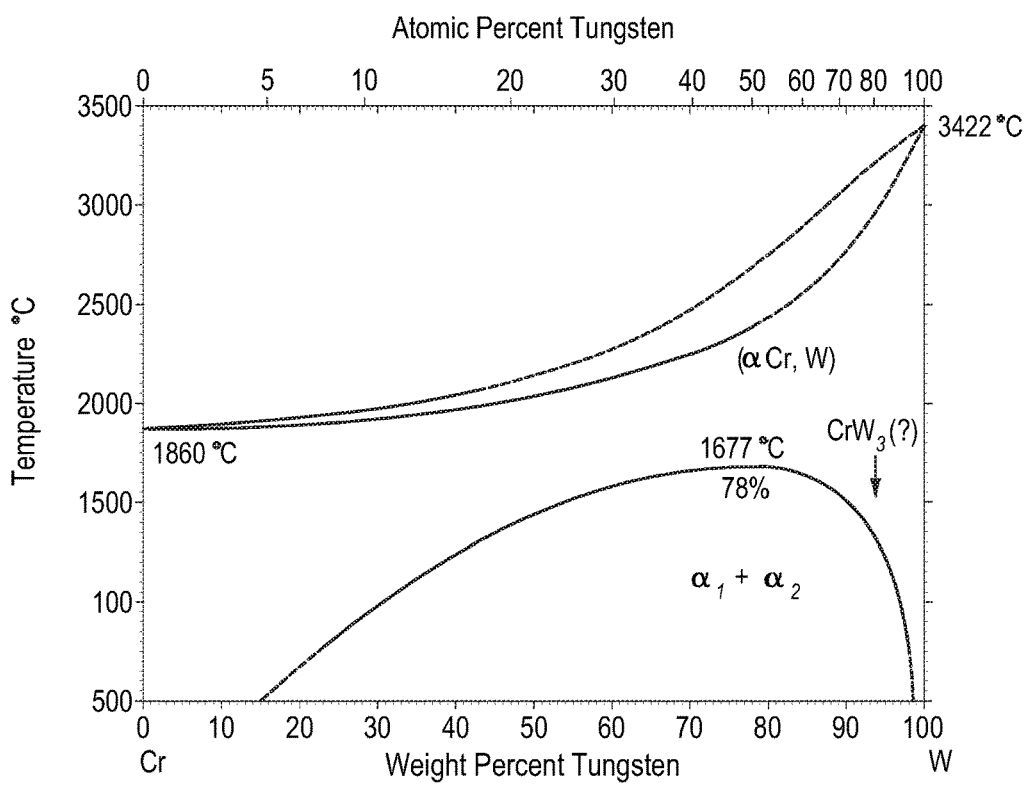
Figure 9A:
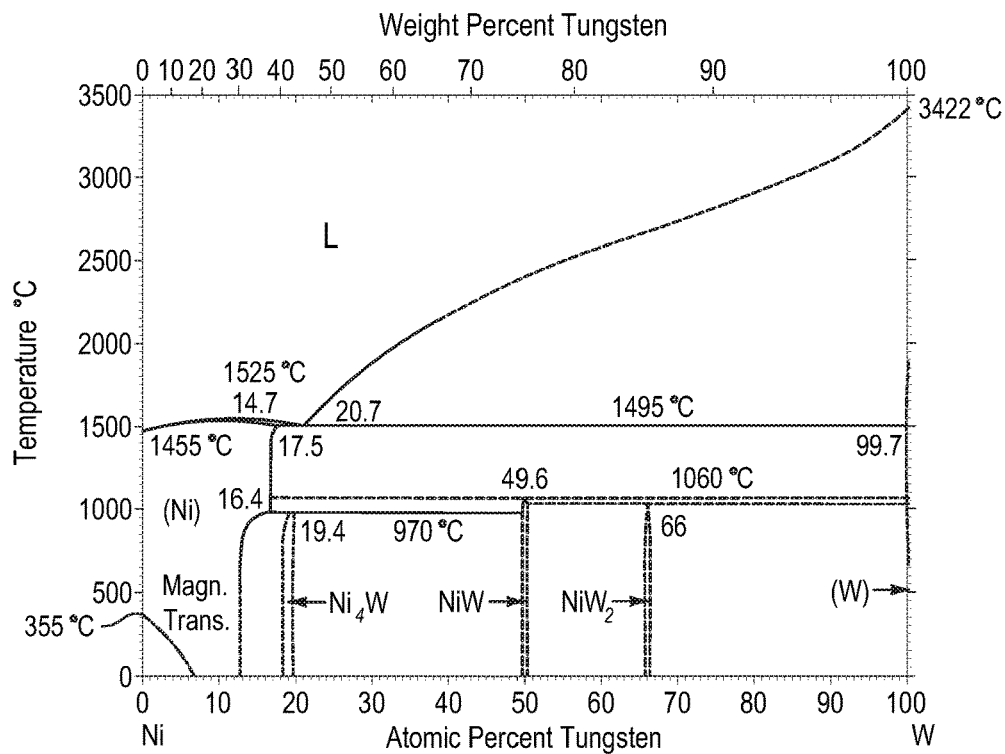
FIGS. 9A and 9B show a phase diagram for nickel-tungsten.
Figure 9B:
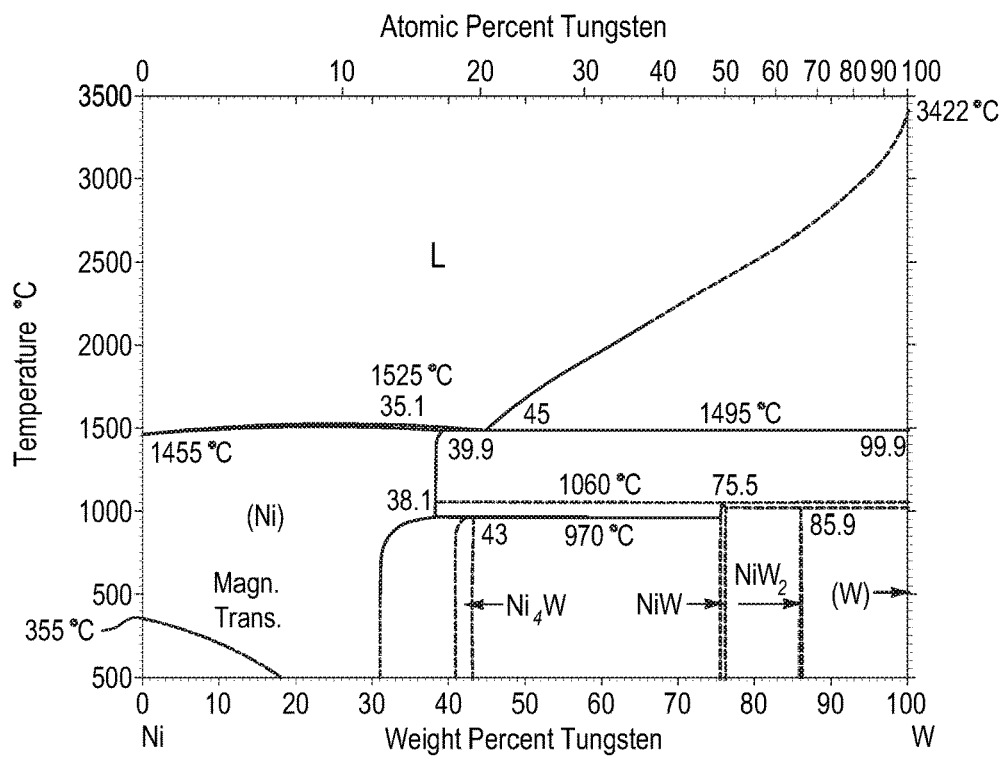

For L-605 CoCr:
- Co—Cr is a complex phase diagram with eutectic, eutectoid, peritectic, peritectoid, and congruent features. It includes at least three distinct phases and two eutectoid compositions. The tetragonal σ intermetallic peritectoid phase exists from about 51 to about 64Cr. L-605 falls into the HCP (εCo) phase area of the diagram (FIGS. 4A-4B).
- Co—Ni is a solid solution across the entire phase diagram, with an atomic structure change from HCP to FCC that occurs around 25Ni. L-605 falls into the (εCo) HCP phase area of the diagram (FIGS. 5A-5B).
- Cr—Ni is a phase diagram with eutectic, peritectoid, and allotropic transformation features. L-605 falls in the eutectoid body centered cubic (BCC)-orthorhombic area of the phase diagram (FIGS. 6A-6B).
- Co—W is an extremely complex phase diagram with eutectic, eutectoid, peritectoid, and allotropic transformation features. L-605 falls within the eutectoid HCP (εCo)—BCC (W) portion of the phase diagram (FIGS. 7A-7B).
- Cr—W is a phase diagram with a large miscibility gap starting around 15 weight percent W. L-605 resides in the miscibility gap (α1+α2) with two BCC phases (FIGS. 8A-8B).
- Ni—W is a complex phase diagram with eutectic and multiple peritectoid reactions. L-605 falls in the eutectoid BCT Ni4W—orthorhombic NiW phase combination (FIGS. 9A-9B).

Figure 10A:
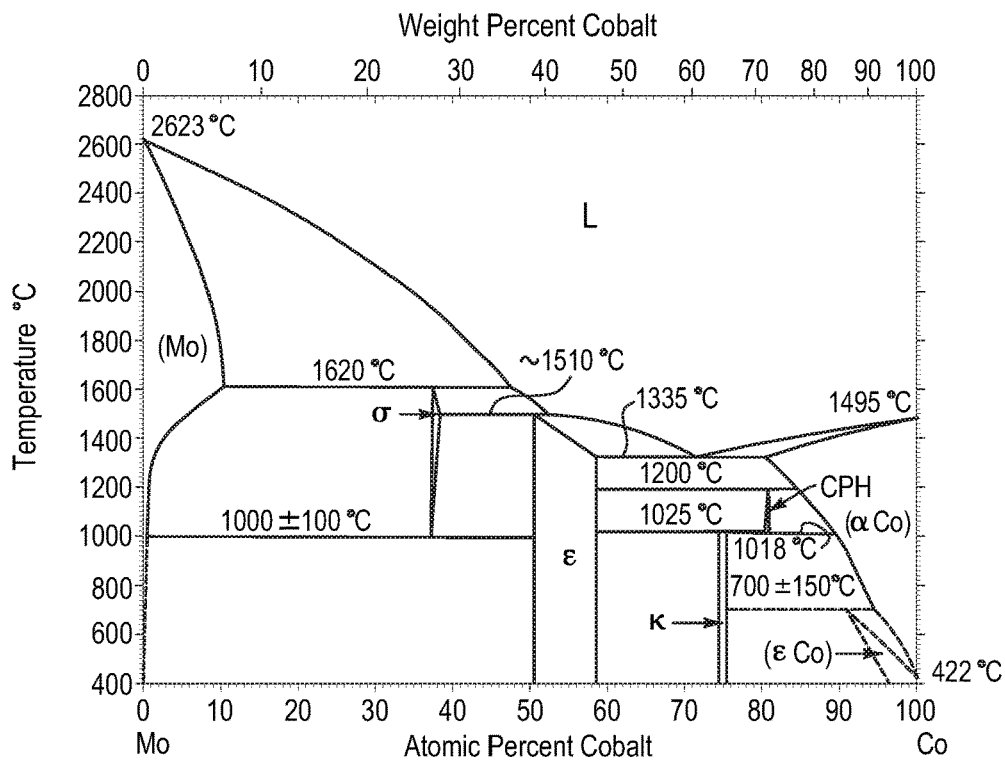
FIGS. 10A and 10B show a phase diagram for molybdenum-cobalt.
Figure 10B:
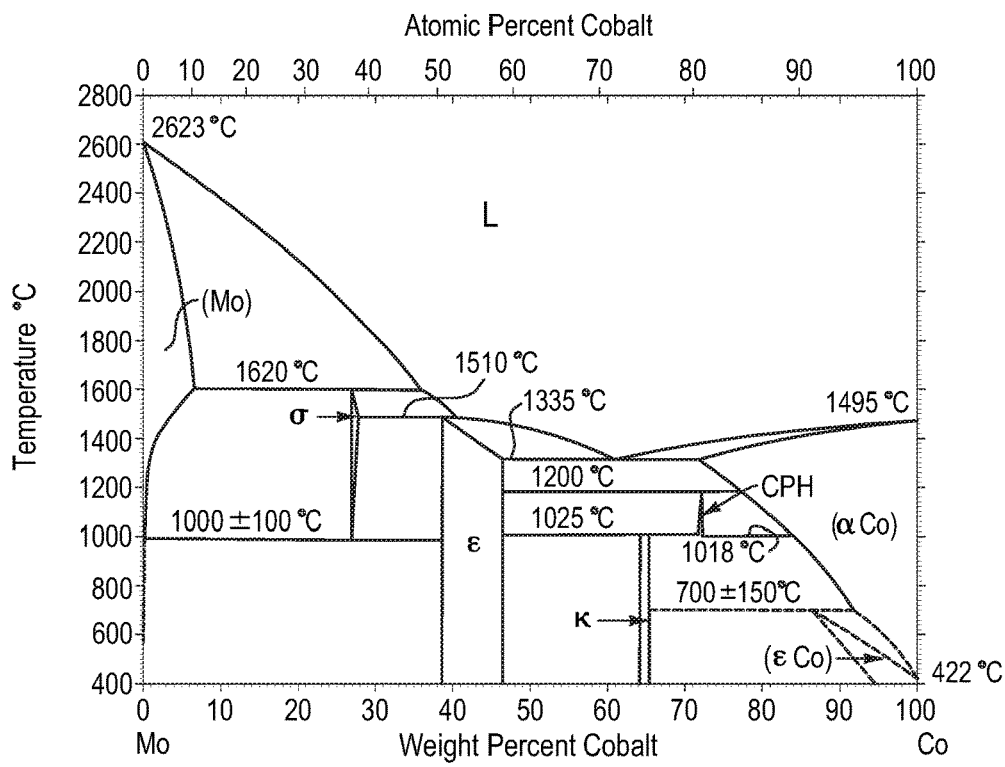
Figure 11A:
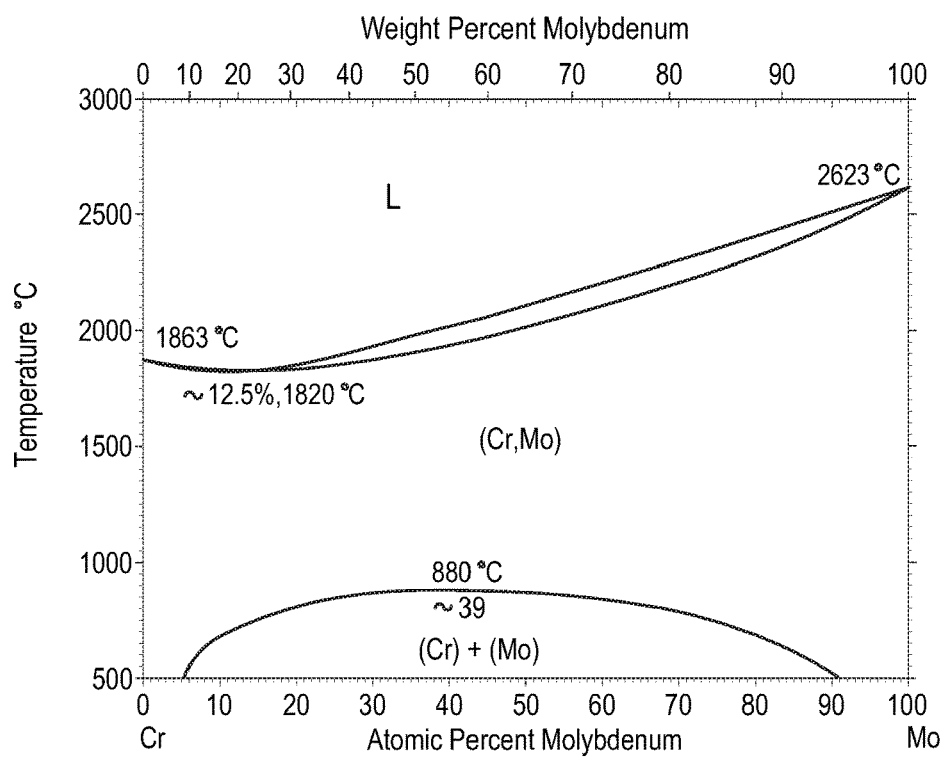
FIGS. 11A and 11B show a phase diagram for chromium-molybdenum.
Figure 11B:
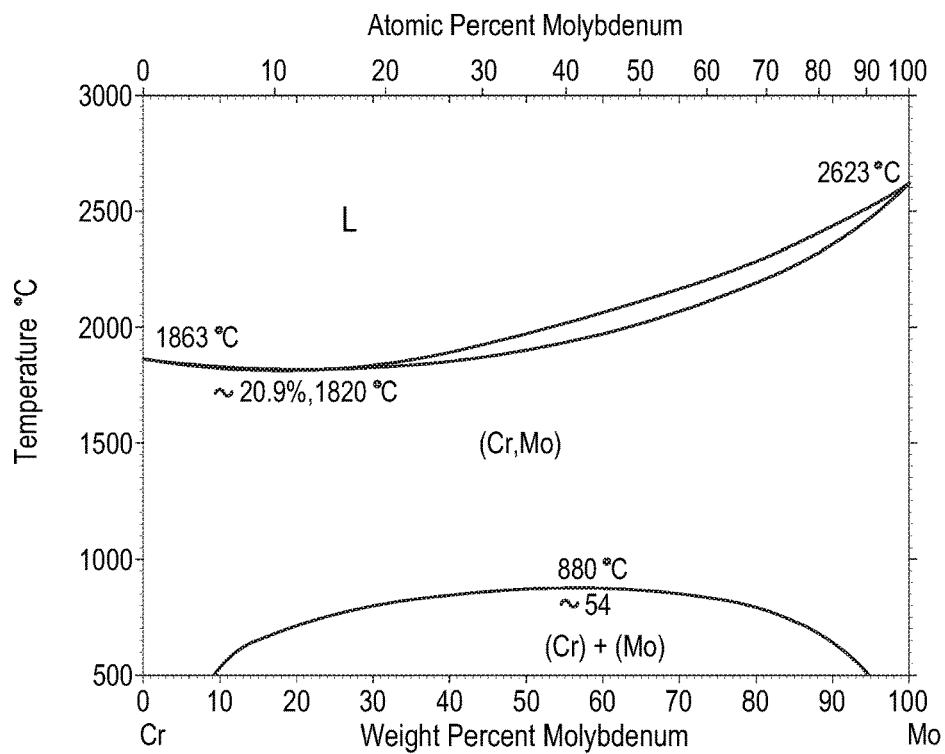
Figure 12A:
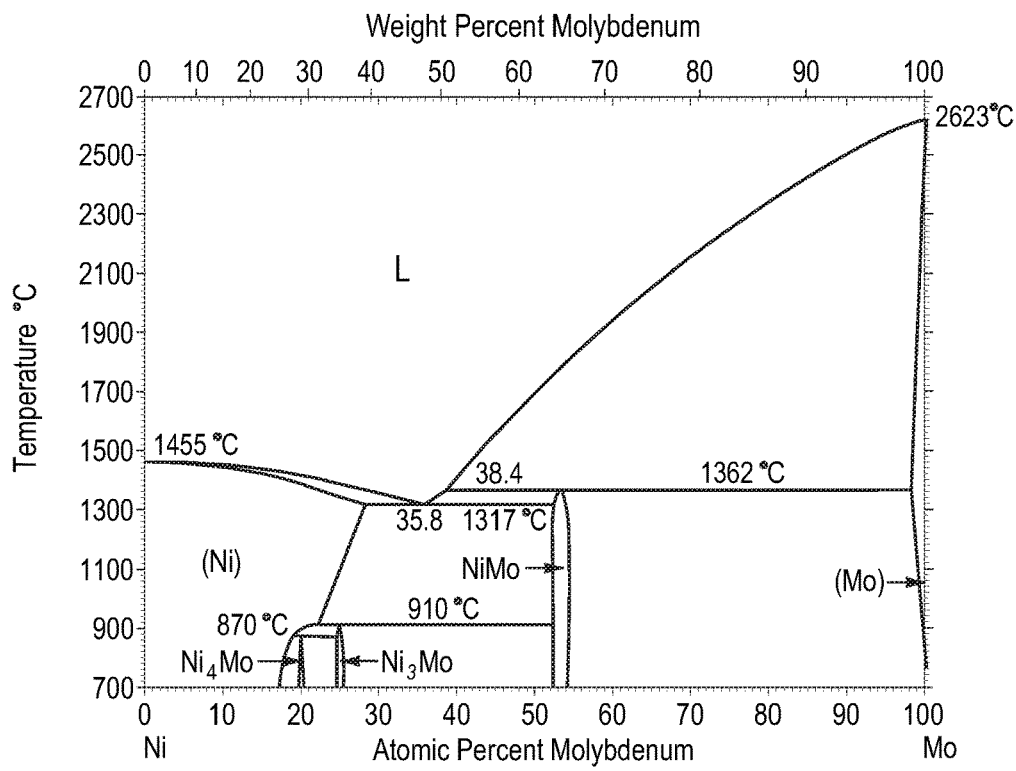
FIGS. 12A and 12B show a phase diagram for nickel-molybdenum.
Figure 12B:
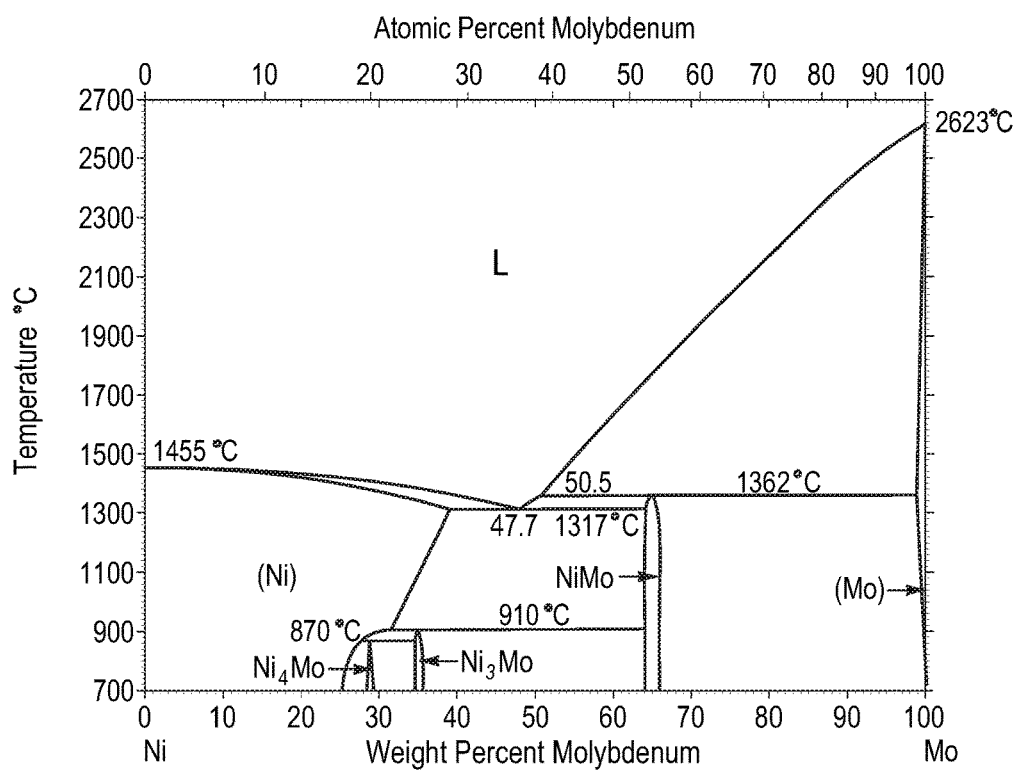

For MP-35N CoCr:
- Co—Cr—MP-35N falls into a eutectoid structure comprised of HCP (εCo) and tetragonal σ phases (FIGS. 4A-4B).
- Co—Ni-MP-35N falls in the FCC (αCo,Ni) portion of the phase diagram (FIGS. 5A-5B).
- Cr—Ni-MP-35N falls in the orthorhombic ordered phase regime of $Ni_2Cr$. It is possible that the presence of the other elements suppresses the formation of this ordered phase (FIGS. 6A-6B).
- Co—Mo is a complex phase diagram with multiple eutectic, peritectoid, and allotropic transformations. Similar to Co—W, two distinct ordered phases are formed, from about 33 to about 35Mo and from about 53 to about 61Mo. MP-35N falls in the region combining HCP κ and HCP (εCo) phases (FIGS. 10A-10B).
- Cr—Mo exhibits a non-mixing region, called a miscibility gap, across most of the phase diagram. This indicates that distinct BCC phases of Cr and of Mo may exist without full mixing of the atoms among each other. MP-35N falls within this miscibility gap (Cr)+(Mo) region (FIGS. 11A-11B).
- Ni—Mo is a phase diagram that exhibits eutectic, peritectoid, and allotropic transformations. MP-35N falls in the FCC solid solution (Ni) regime of the phase diagram (FIGS. 12A-12B).

As can be seen from the complex phase diagrams described above, the equilibrium microstructures need not be single phase (i.e., fully solid solution) for an alloy composition to be selected that works well (as it is already established that L-605 and MP-35N work from a workability perspective, although with relatively lower radiopacity than desired).

The next discussion covers the elements listed above from the perspective of substituting for part or all of the Ni and possibly part of the Co in L-605 and MP-35N alloys. Other Co—Cr alloys (e.g., Elgiloy, Phynox) could similarly be substituted. In addition, an entirely new alloy composition may be developed independent of basing the initial substitution on existing alloys.

Figure 13A:
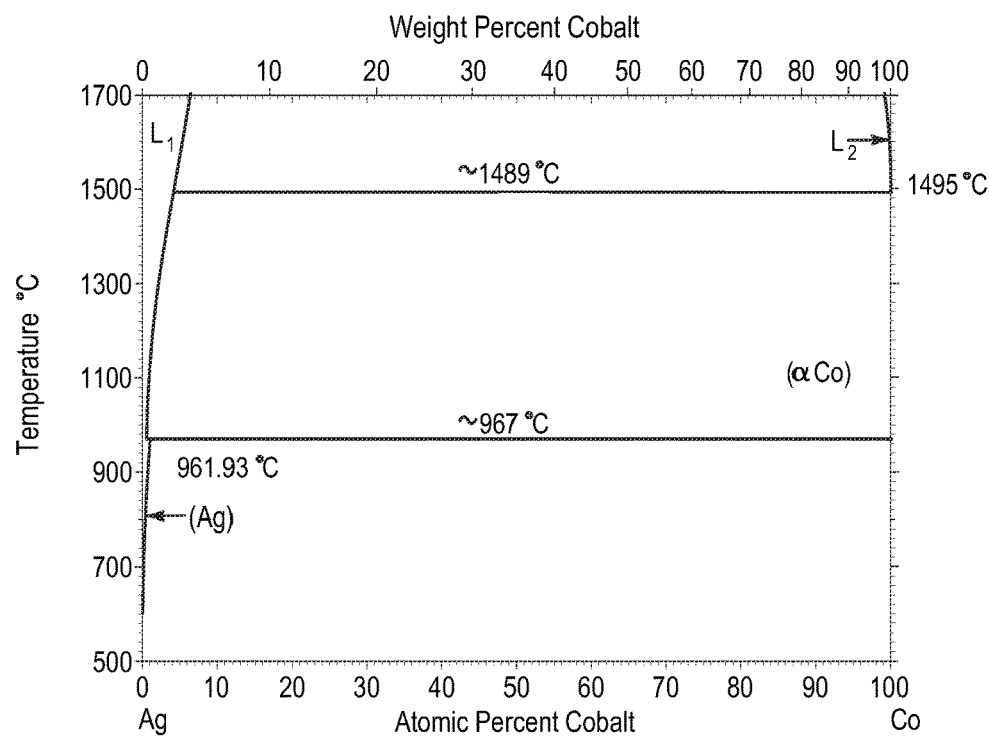
FIGS. 13A and 13B show a phase diagram for silver-cobalt.
Figure 13B:
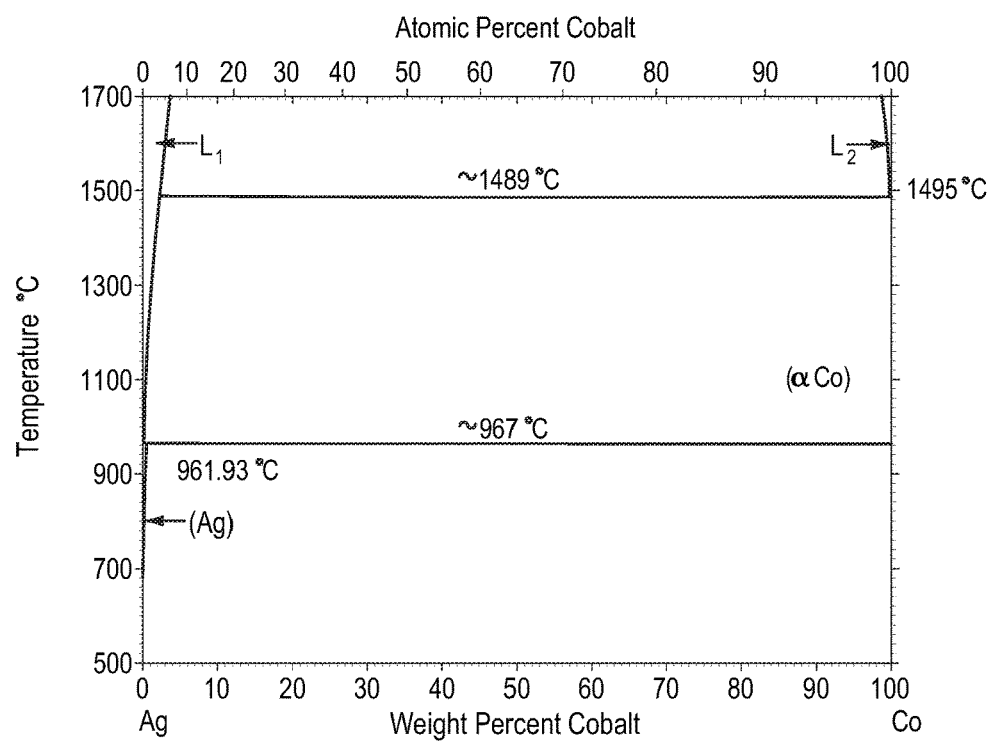
Figure 14A:
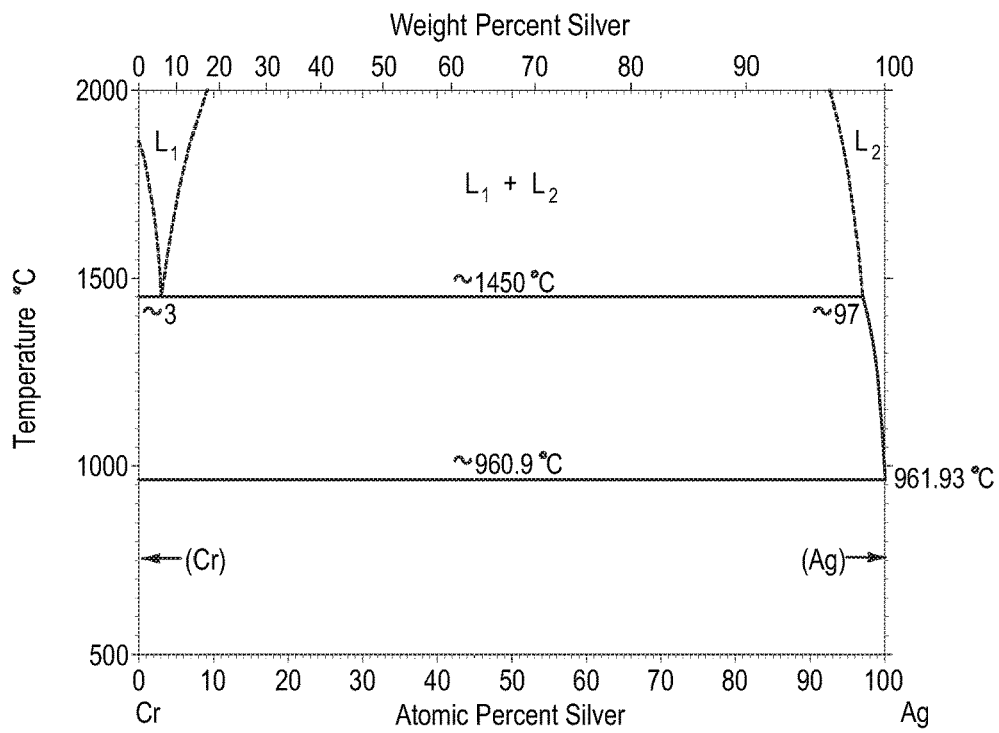
FIGS. 14A and 14B show a phase diagram for chromium-silver.
Figure 14B:
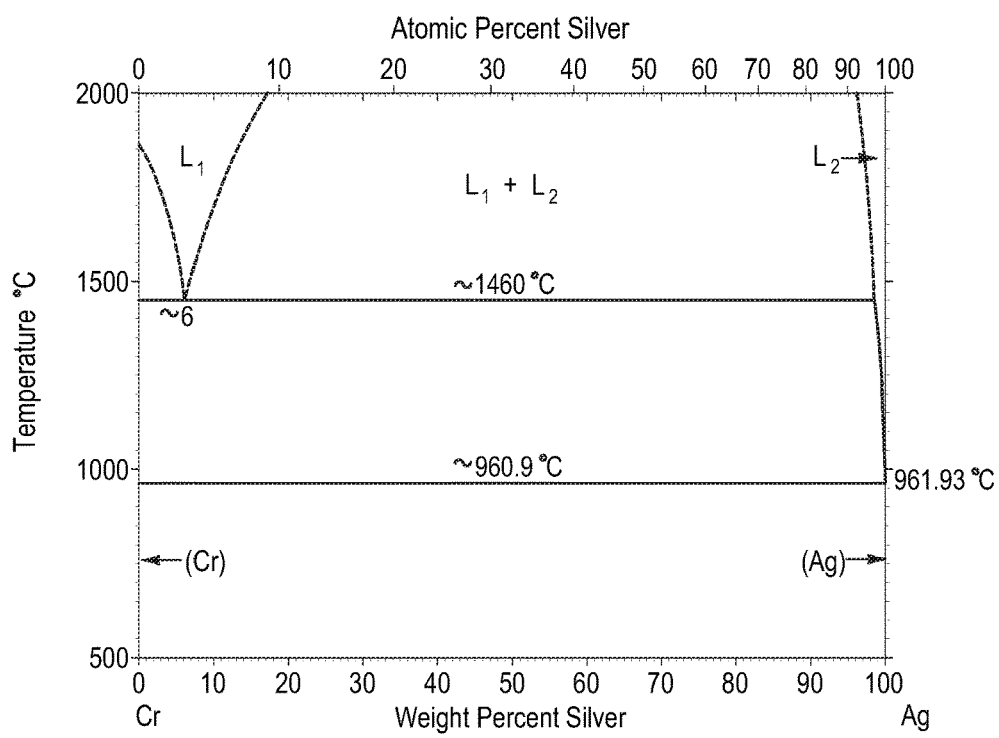
Figure 15A:
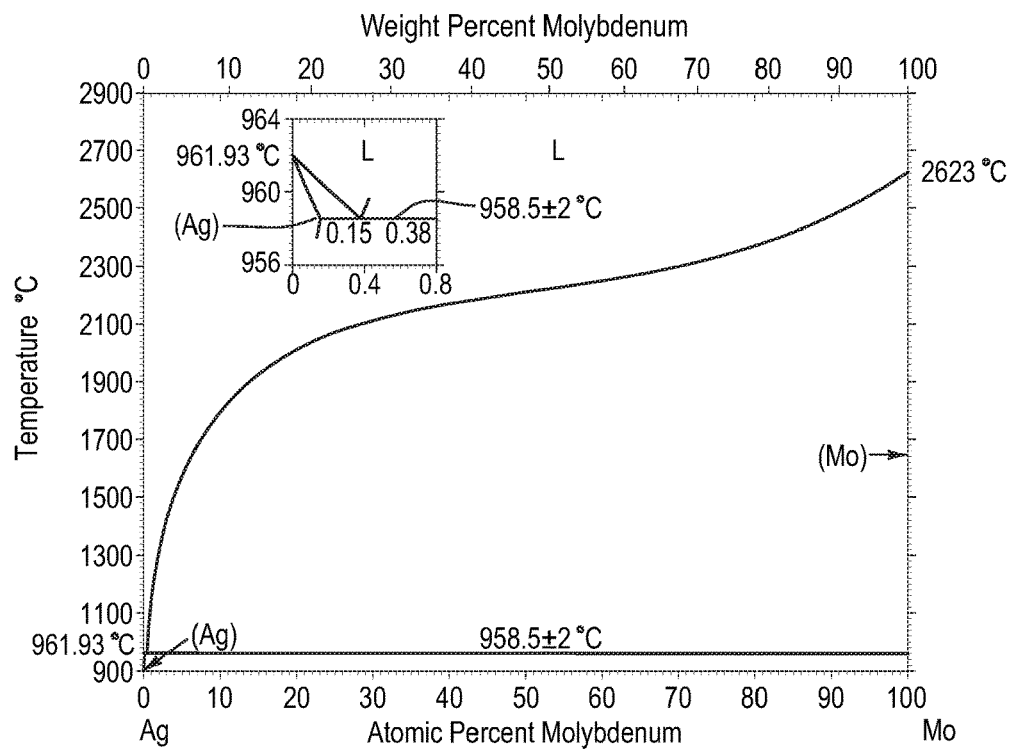
FIGS. 15A and 15B show a phase diagram for silver-molybdenum.
Figure 15B:
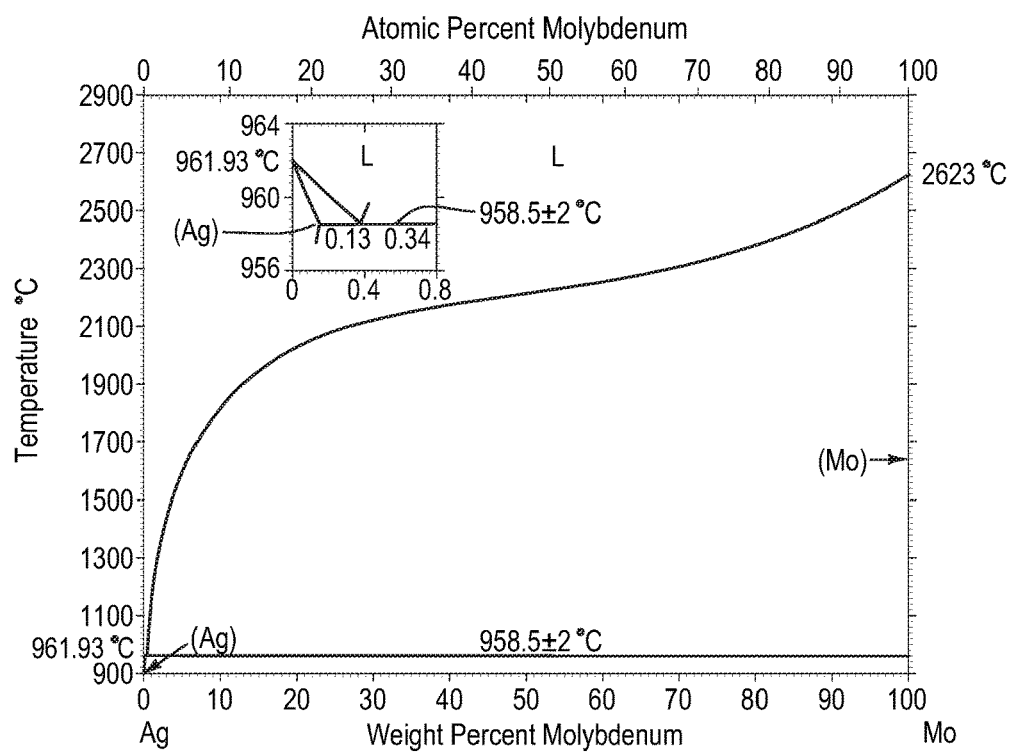

For an alloy containing Ag, considering different compositions that may include Mo and/or W:
- Ag—Co phase diagram shows a complete miscibility gap with two allotropic transformations. Any mixture at the temperatures of interest will simply include a mixture of FCC (Ag) and HCP (εCo) phases (FIGS. 13A-13B).
- Ag—Cr phase diagram shows a eutectic and a miscibility gap with two allotropic transformations. At the temperatures of interest, any mixture will simply include FCC (Ag) and BCC (Cr) phases regardless of composition (FIGS. 14A-14B).
- Ag—Mo is a phase diagram with a eutectic at the Ag side and an allotropic transformation. With the two elements being immiscible at the temperatures of interest, the material will simply include a mixture of FCC (Ag) and BCC (Mo) phases regardless of composition (FIGS. 15A-15B).
- Ag—W is completely immiscible across all compositions. This indicates that the material will simply include a mixture of FCC (Ag) and BCC (W) phases.

Figure 16A:
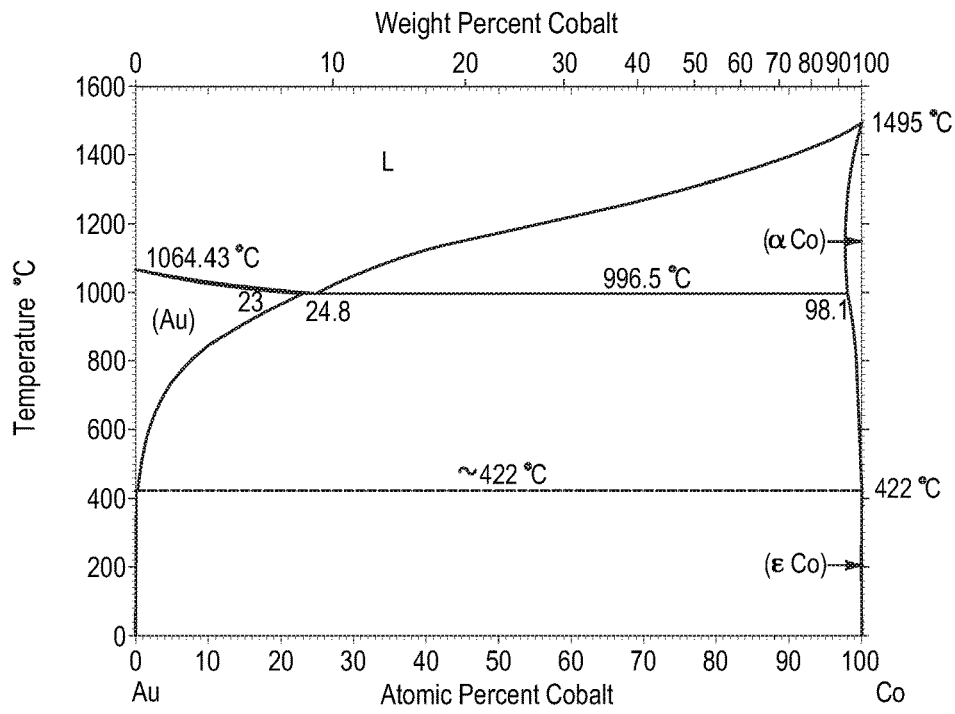
FIGS. 16A and 16B show a phase diagram for gold-cobalt.
Figure 16B:
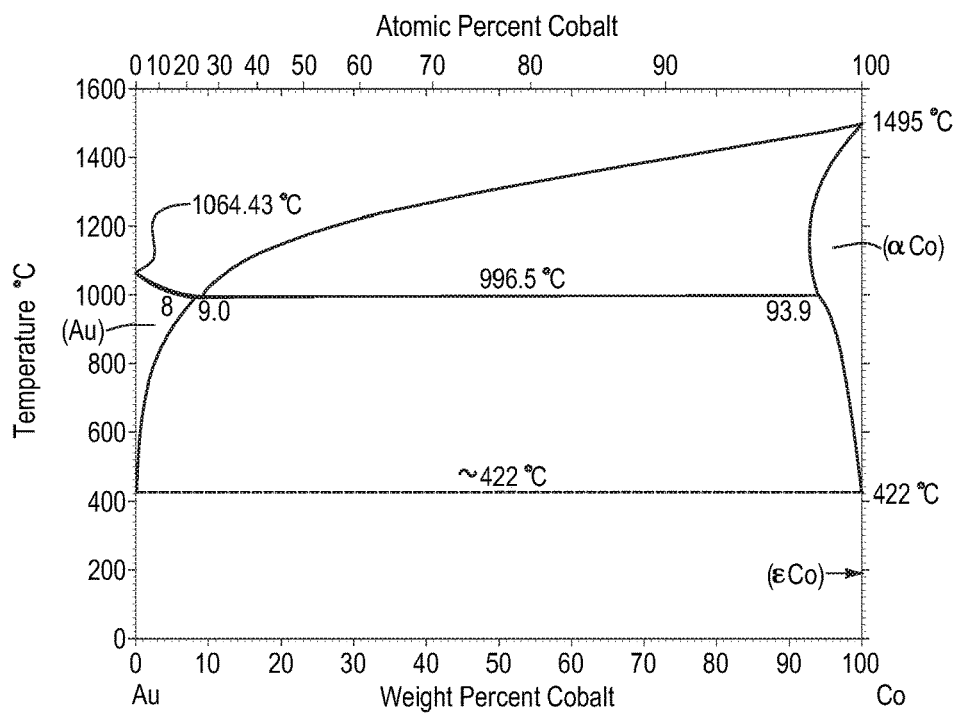
Figure 17A:
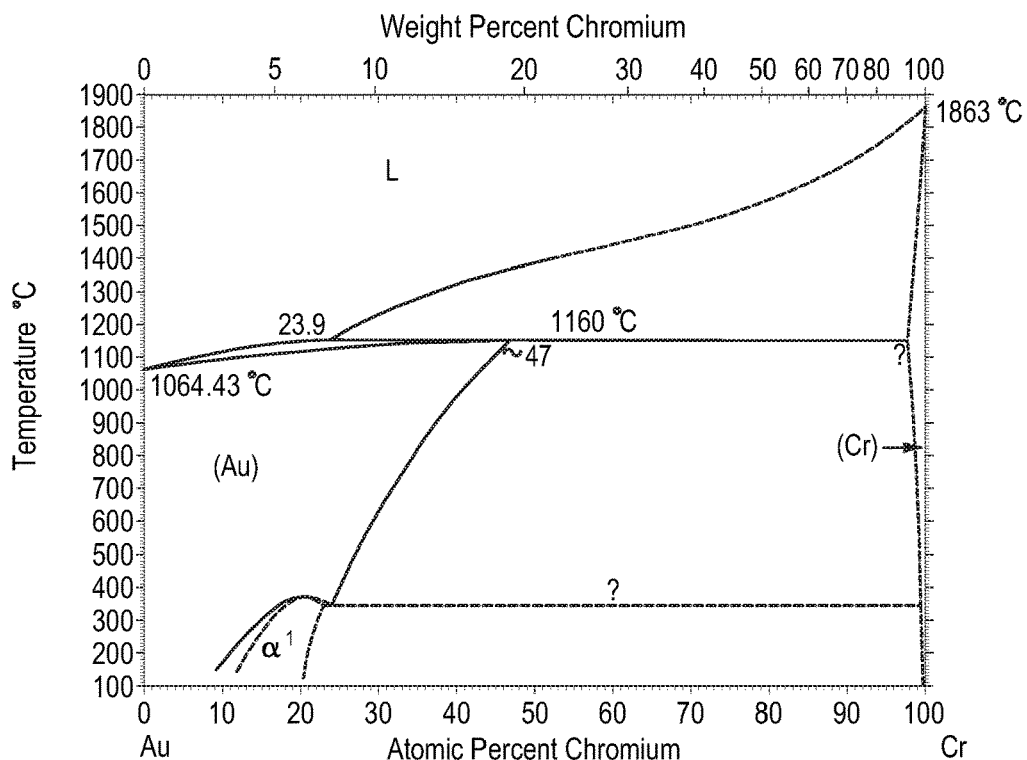
FIGS. 17A and 17B show a phase diagram for gold-chromium.
Figure 17B:
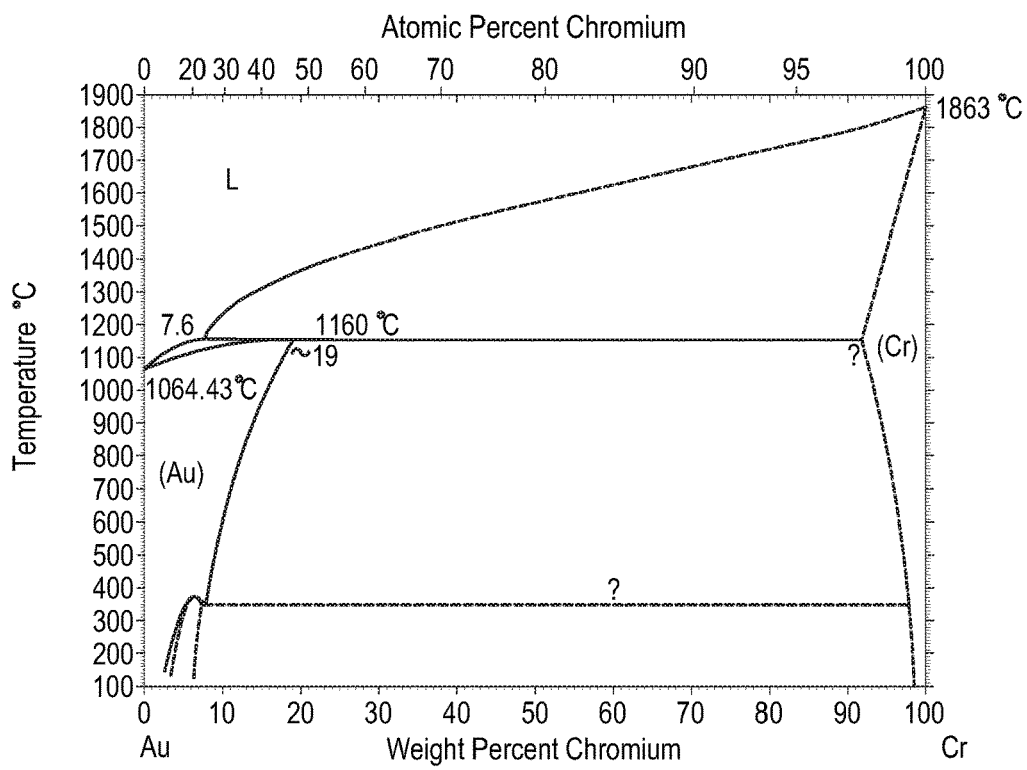
Figure 18A:
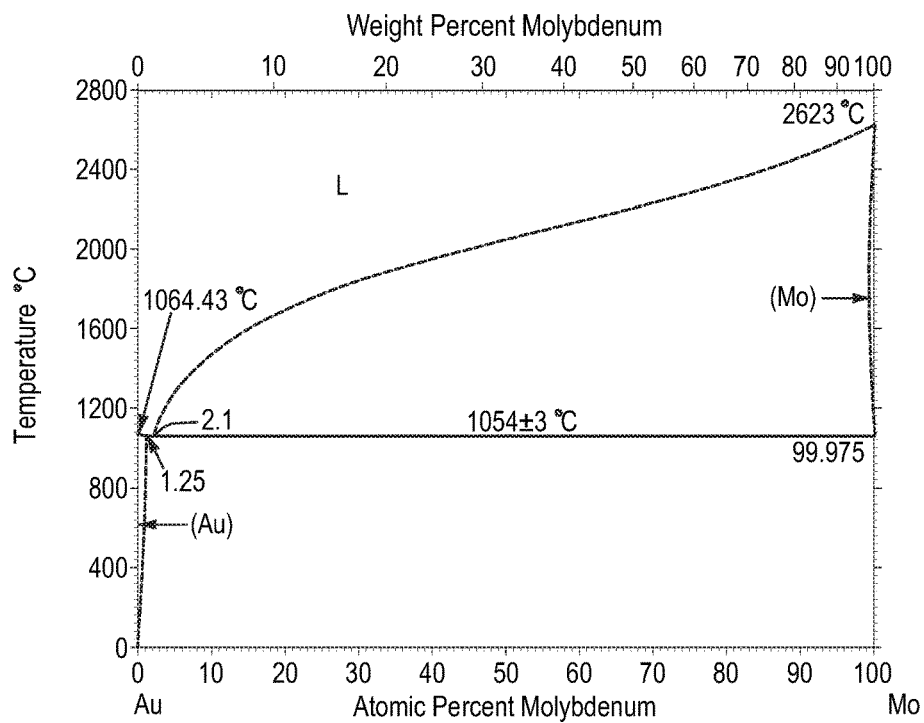
FIGS. 18A and 18B show a phase diagram for gold-molybdenum.
Figure 18B:
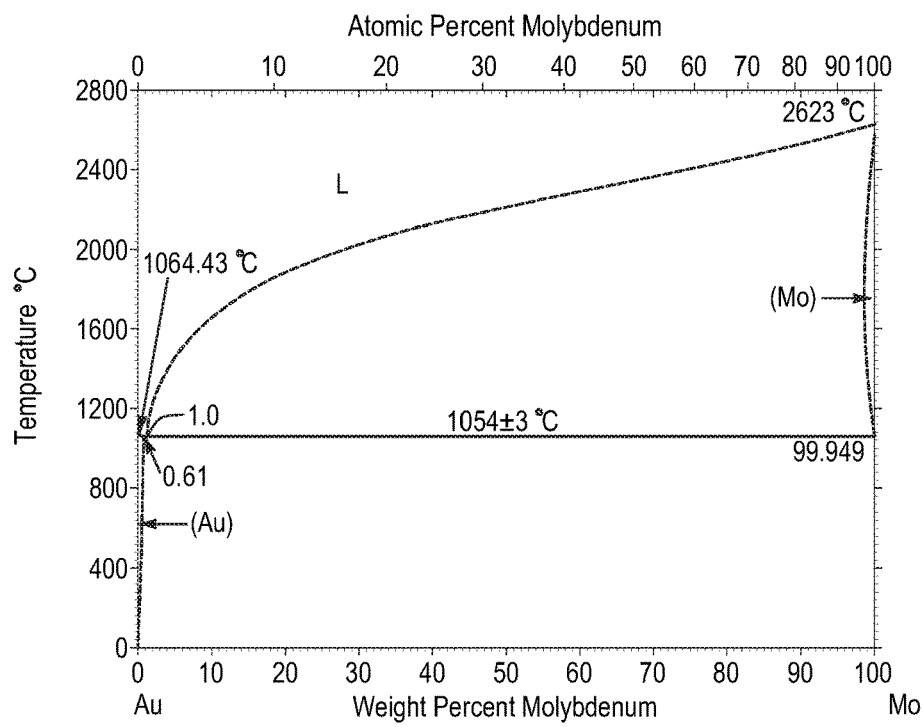
Figure 19A:
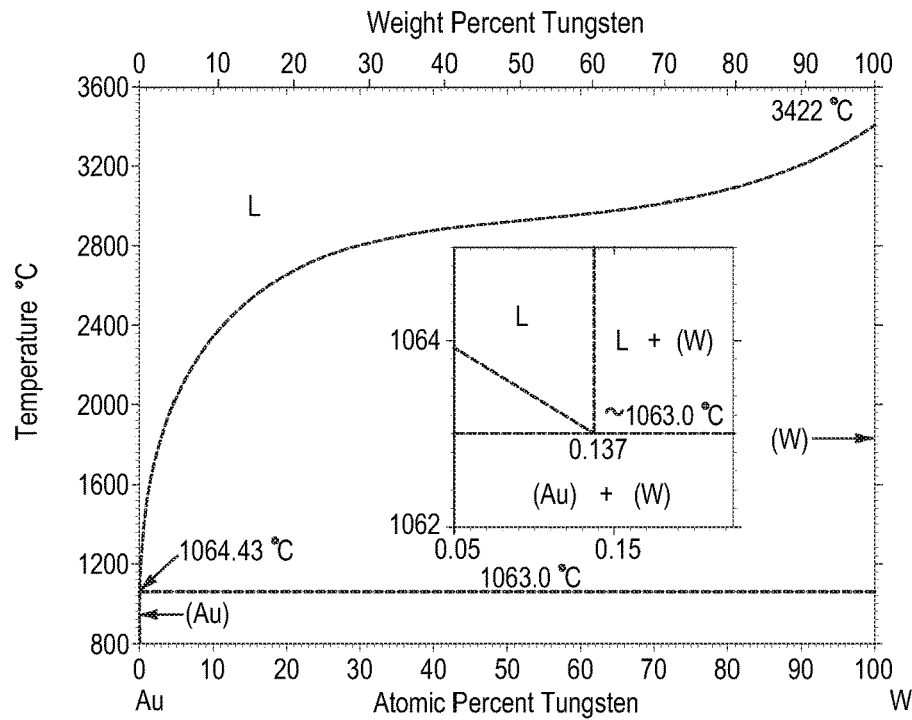
FIGS. 19A and 19B show a phase diagram for gold-tungsten.
Figure 19B:
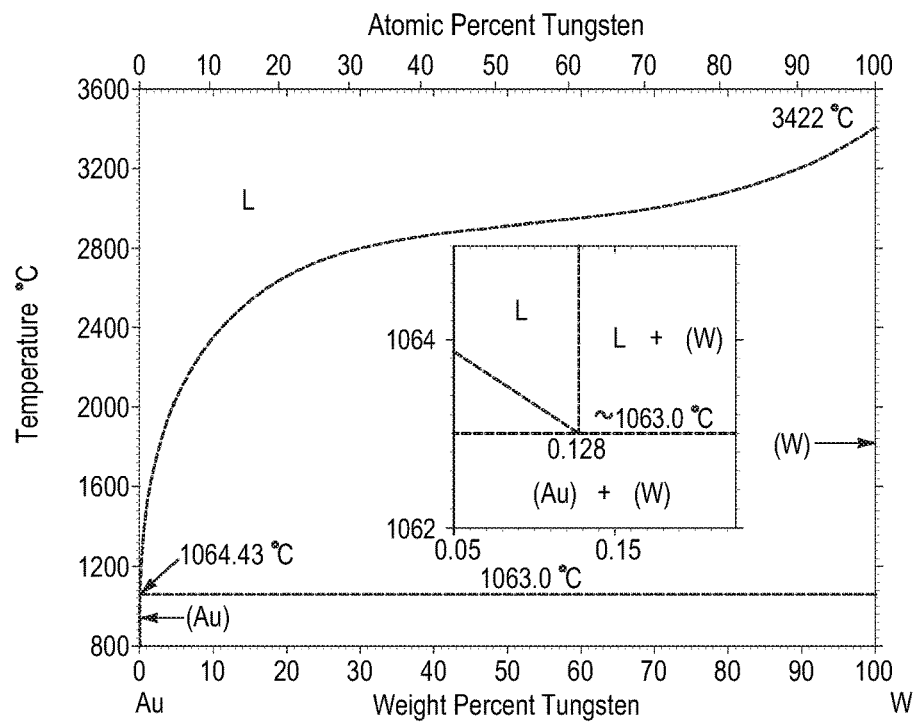

For an alloy containing Au, considering different compositions that may include Mo and/or W:
- Au—Co is a phase diagram with eutectic, eutectoid, and allotropic transformation features. The material will simply include a mixture of FCC (Au) and HCP (εCo) phases regardless of composition (FIGS. 16A-16B).
- Au—Cr displays eutectic and ordering in the phase diagram. From about 1 to 6Au, an ordered Au4Cr (α') BCT phase forms. Above this region the material will include a mixture of BCT α' and BCC (Cr) phases (FIGS. 17A-17B).
- Au—Mo is a eutectic across the entire phase diagram. This indicates that the material will include a mixture of FCC (Au) and BCC (Mo) phases regardless of composition (FIGS. 18A-18B).
- Au—W is a eutectic across the entire phase diagram. This indicates that the material will include a mixture of FCC (Au) and BCC (W) phases regardless of composition (FIGS. 19A-19B).

Figure 20A:
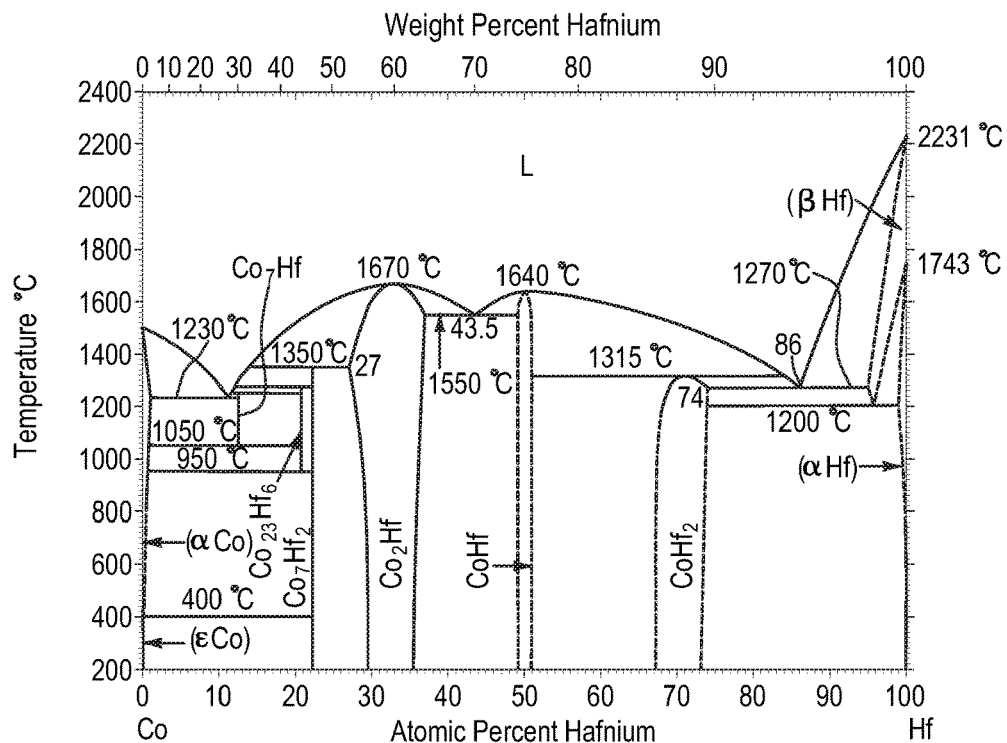
FIGS. 20A and 20B show a phase diagram for cobalt-hafnium.
Figure 20B:
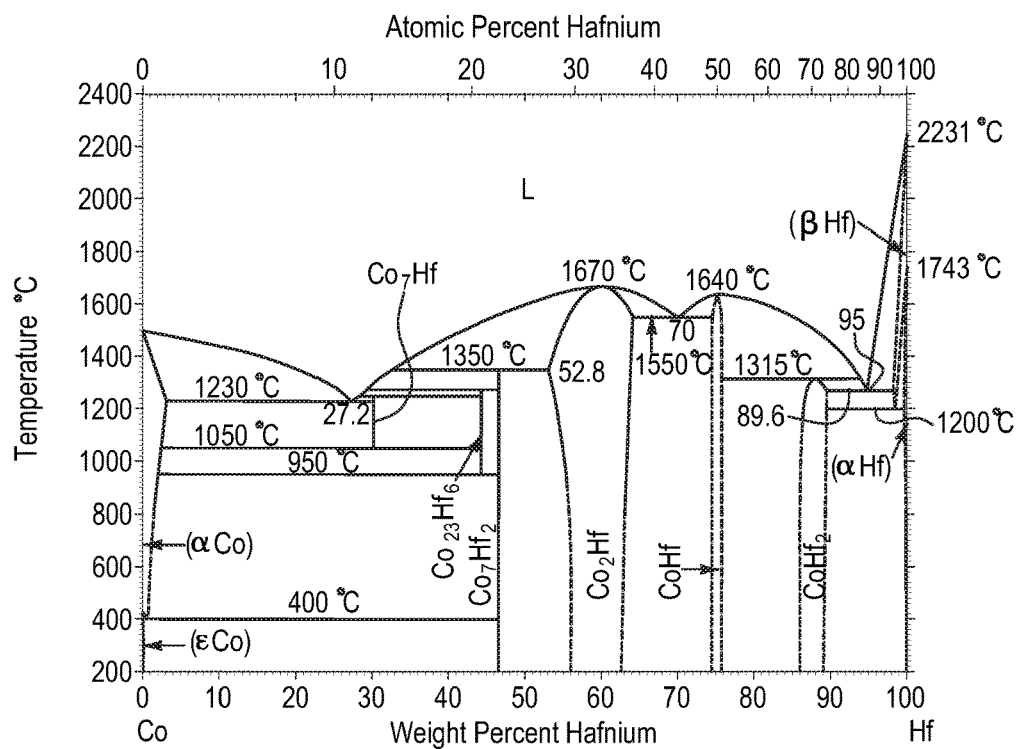

For an alloy containing Hf, considering different compositions that may include Mo and/or W:
- Co—Hf is a complex phase diagram with multiple eutectics, eutectoids, peritectics, congruent, and allotropic transformations. It is possible that this mixture becomes paramagnetic as early as about 47Hf. Up to this point, (e.g., about 46.5Hf), the microstructure will be a combination of HCP (εCo) and tetragonal $Co_7Hf_2$. From about 46.5 to about 56Hf, the microstructure is a mix of tetragonal $Co_7Hf_2$ and FCC $Co_2Hf$. From about 56 to about 62.5Hf is the ordered FCC $Co_2Hf$ phase. From about 62.5 to about 74.5Hf the microstructure is a mixture of FCC $Co_2Hf$ and cubic CoHf phases. The cubic CoHf phase sits from about 74.5 to about 75.5Hf. From about 75.5 to about 86Hf, the microstructure is a mix of the cubic CoHf and FCC $CoHf_2$ phases. The FCC $CoHf_2$ phase sits from about 86 to about 89Hf. Above about 89Hf is a mixture of FCC $CoHf_2$ and HCP (αHf) phases (FIGS. 20A-20B).
- Cr—Hf phase diagram shows two eutectics, one eutectoid, and one intermediate FCC $Cr_2Hf$ phase from about 62 to about 65Hf. Below this intermediate phase the microstructure should include FCC $Cr_2Hf$ plus (Cr)

Figure 21A:
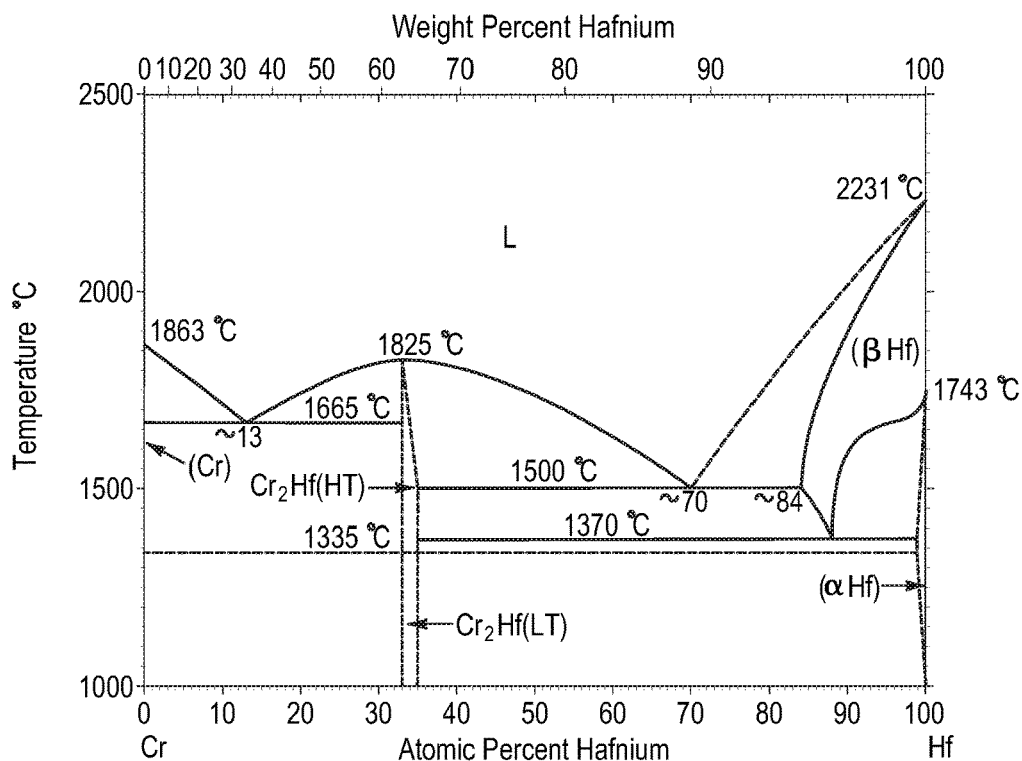
FIGS. 21A and 21B show a phase diagram for chromium-hafnium.
Figure 21B:
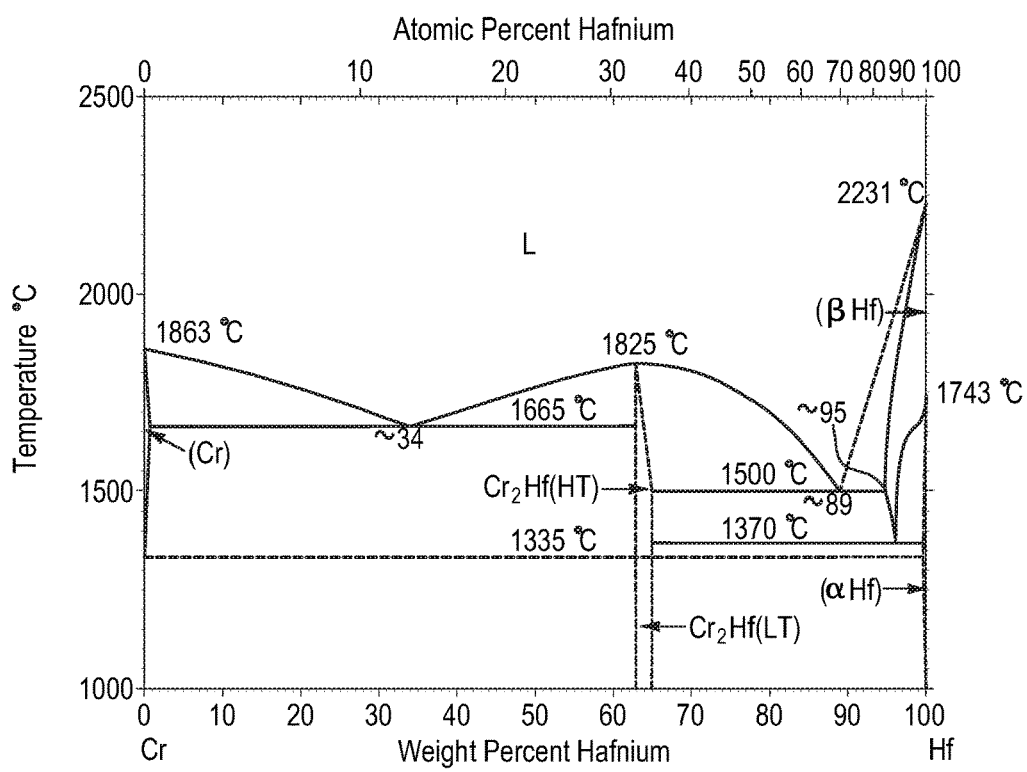

BCC phases. Above the Cr$_2$Hf phase, the eutectic should be a mix of Cr$_2$Hf and HCP (αHf) phases (FIGS. 21A-21B).

Figure 22A:
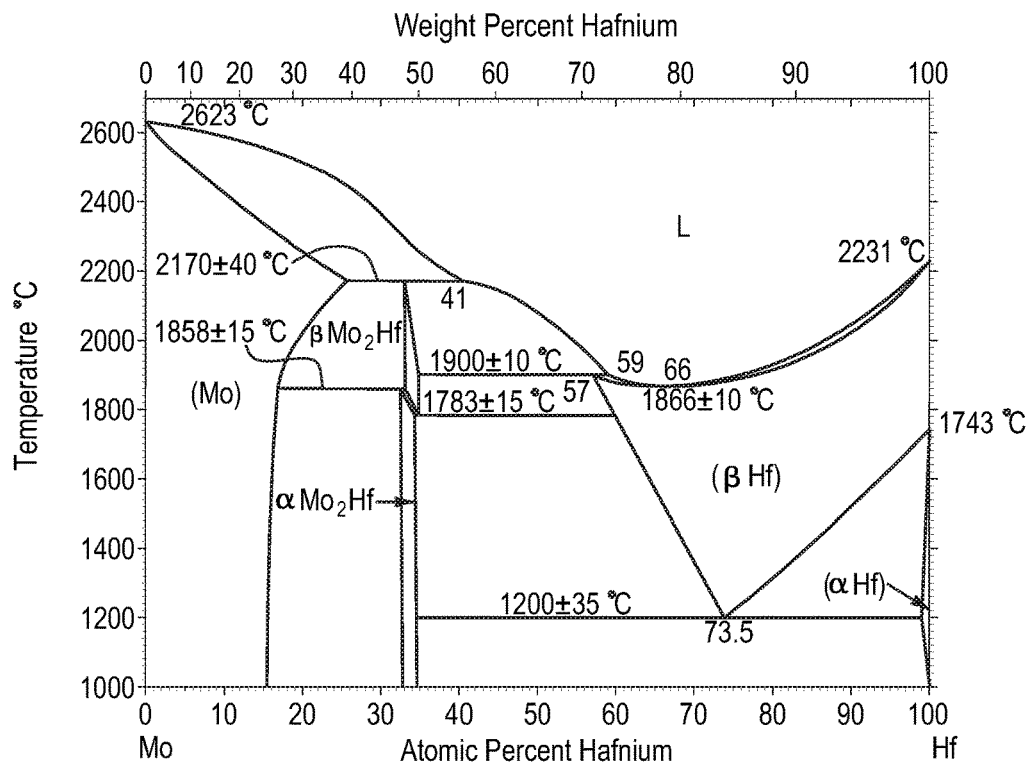
FIGS. 22A and 22B show a phase diagram for molybdenum-hafnium.
Figure 22B:
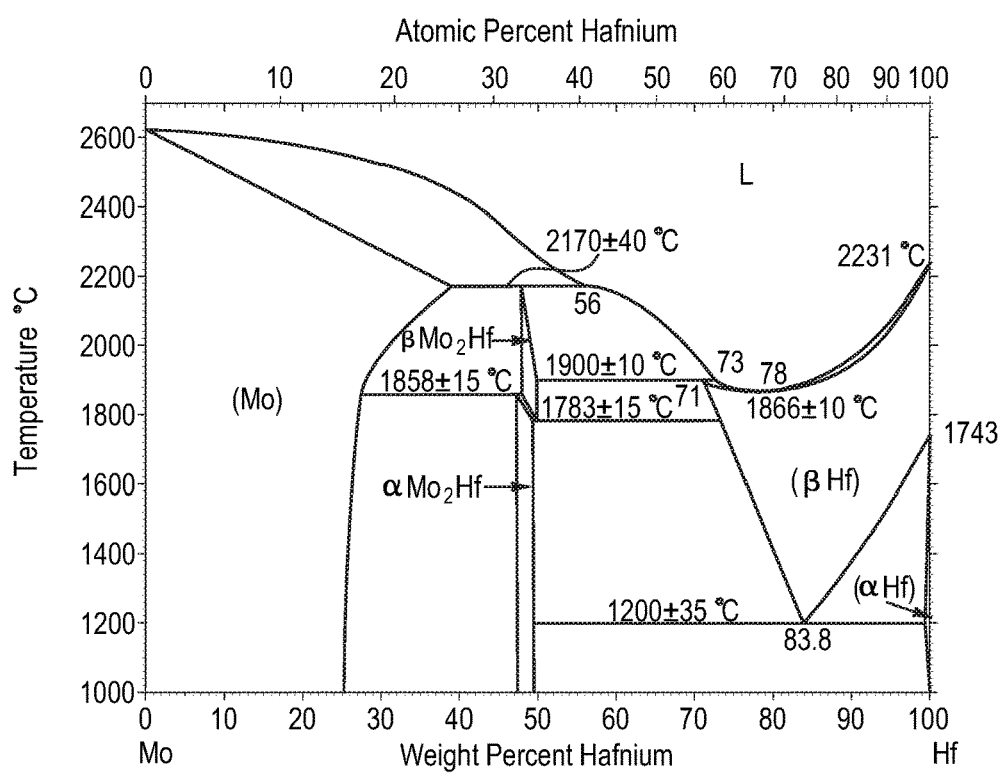

Hf—Mo is a complex phase diagram with eutectic, eutectoid, peritectic, and allotropic phase transformations. Only one ordered FCC αMo$_2$Hf phase exists at the temperatures of interest, from about 47 to about 50 relative weight percent Hf. Up to about 25Hf, a BCC (Mo) solid solution exists. From about 25 to about 47Hf the microstructure would be a mix of BCC (Mo) solid solution and FCC αMo$_2$Hf. Above about 50Hf is a mix of this phase (i.e., FCC αMo$_2$Hf) and HCP (αHf) (FIGS. 22A-22B).

Figure 23A:
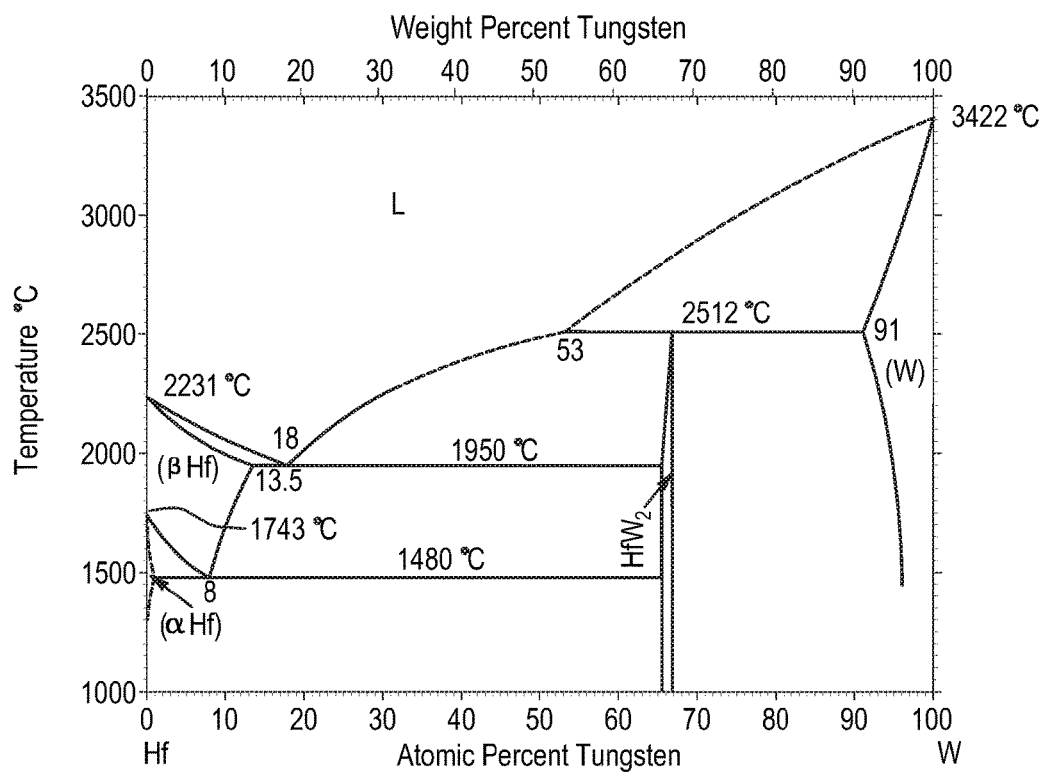
FIGS. 23A and 23B show a phase diagram for hafnium-tungsten.
Figure 23B:
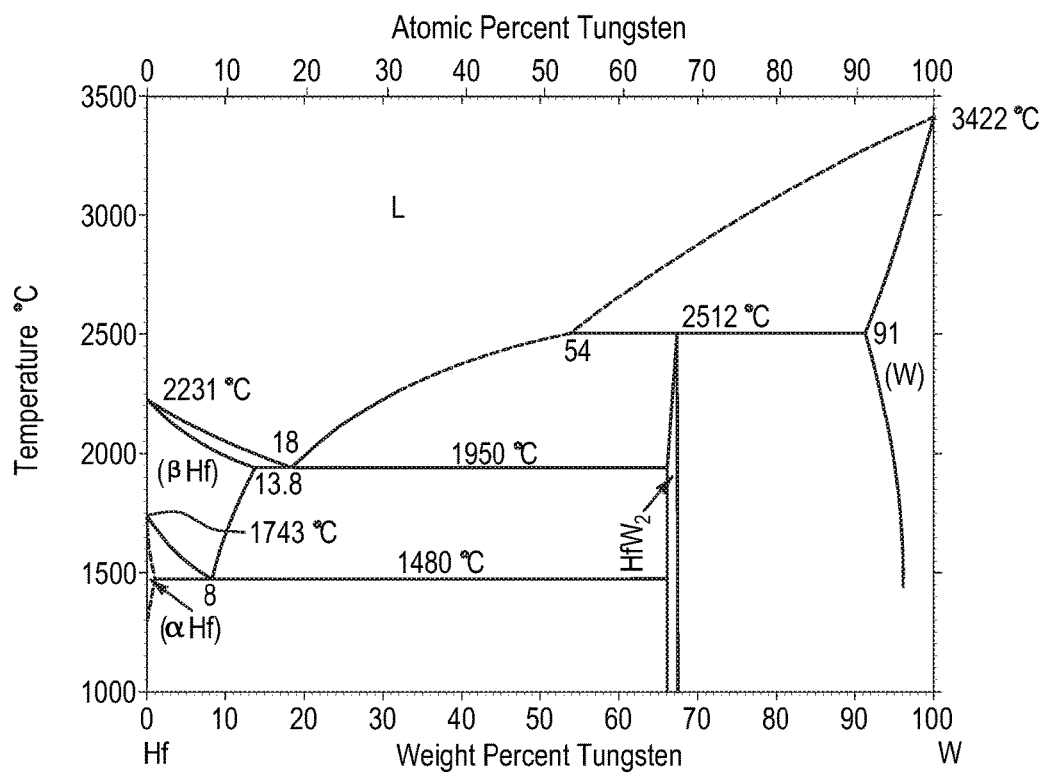

Hf—W, similar to Hf—Mo, is a phase diagram with a eutectic, eutectoid, peritectic/ordered phase, with allotropic transformations. The one ordered FCC HfW$_2$ phase exists from about 66 to about 68Hf. Below this phase the microstructure is a mix of BCC (W) and FCC HfW$_2$. Above this phase is a mix of FCC HfW$_2$ and HCP (αHf) (FIGS. 23A-23B).

Figure 24A:
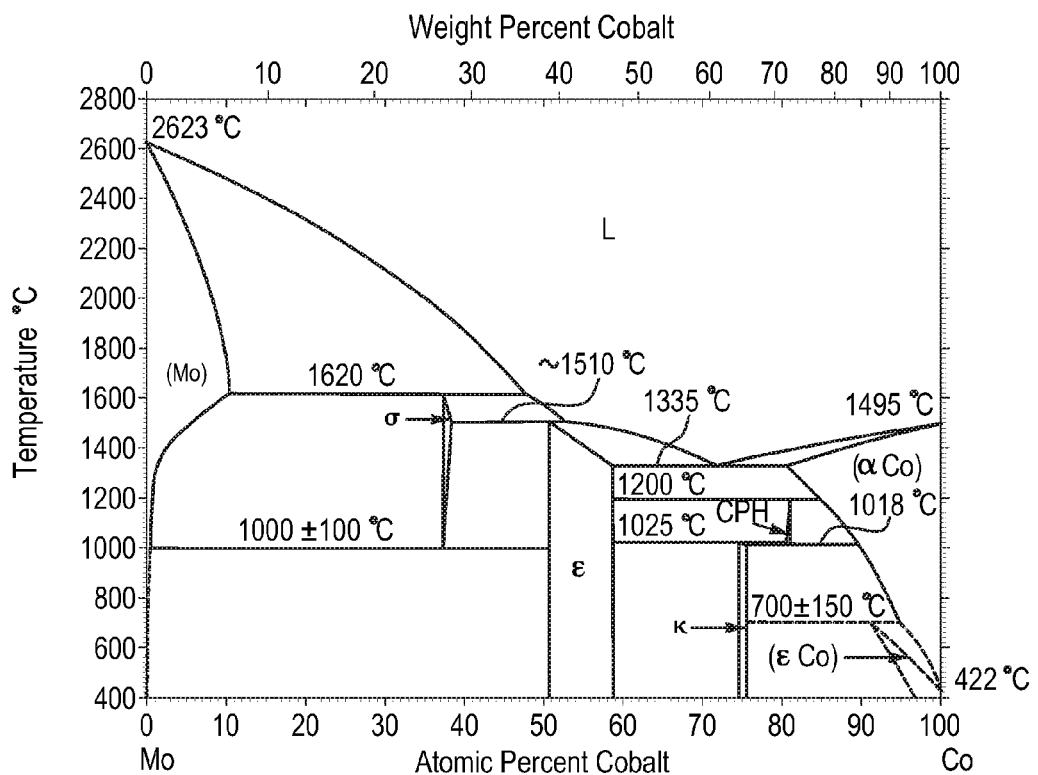
FIGS. 24A and 24B show a phase diagram for molybdenum-cobalt.
Figure 24B:
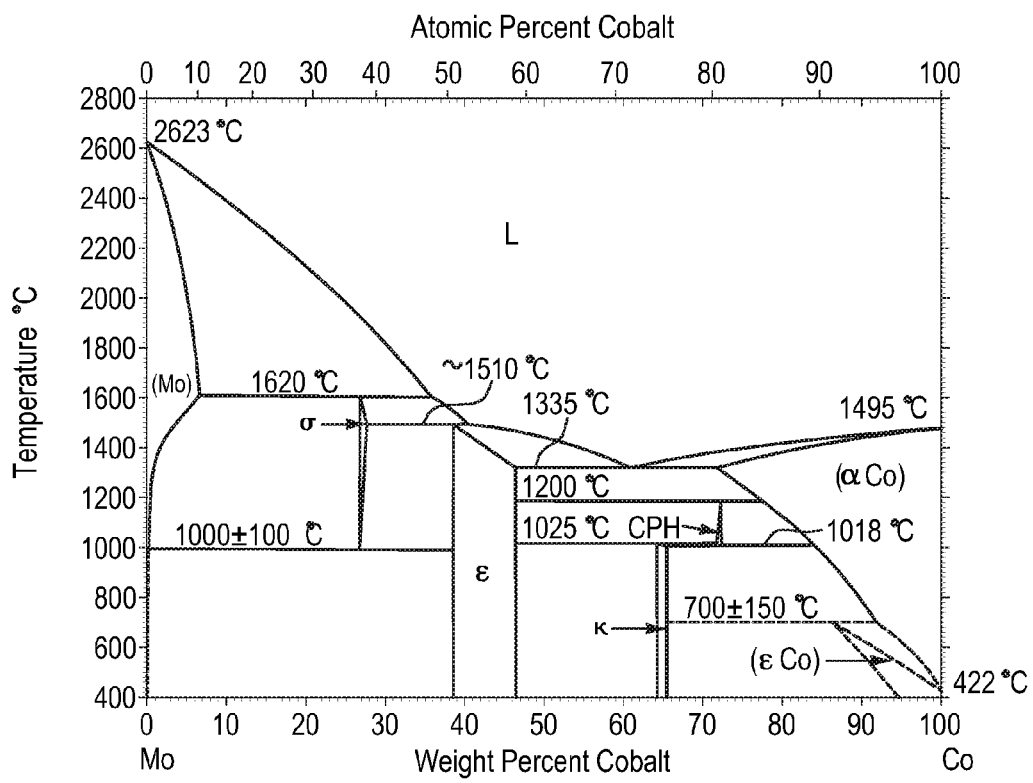

For an alloy containing Mo, the following may be observed:

Co—Mo is a complex phase diagram with two eutectics, a peritectic, peritectoids/ordered phases, and allotropic transformations. Two distinct ordered phases exist at the temperature of interest. The HCP κ phase falls from about 34 to about 36Mo while the rhombohedral E phase falls from about 53 to about 61Mo. Up to about 6Mo, HCP (εCo) appears to be the primary phase. From about 6 to about 34Mo is an HCP (εCo) and HCP κ mixture. From about 36 to about 53Mo a mixture of HCP κ and rhombohedral E exist. Above about 61Mo is a mixture of rhombohedral ε and BCC (Mo) (FIGS. 24A-24B).

Figure 25A:
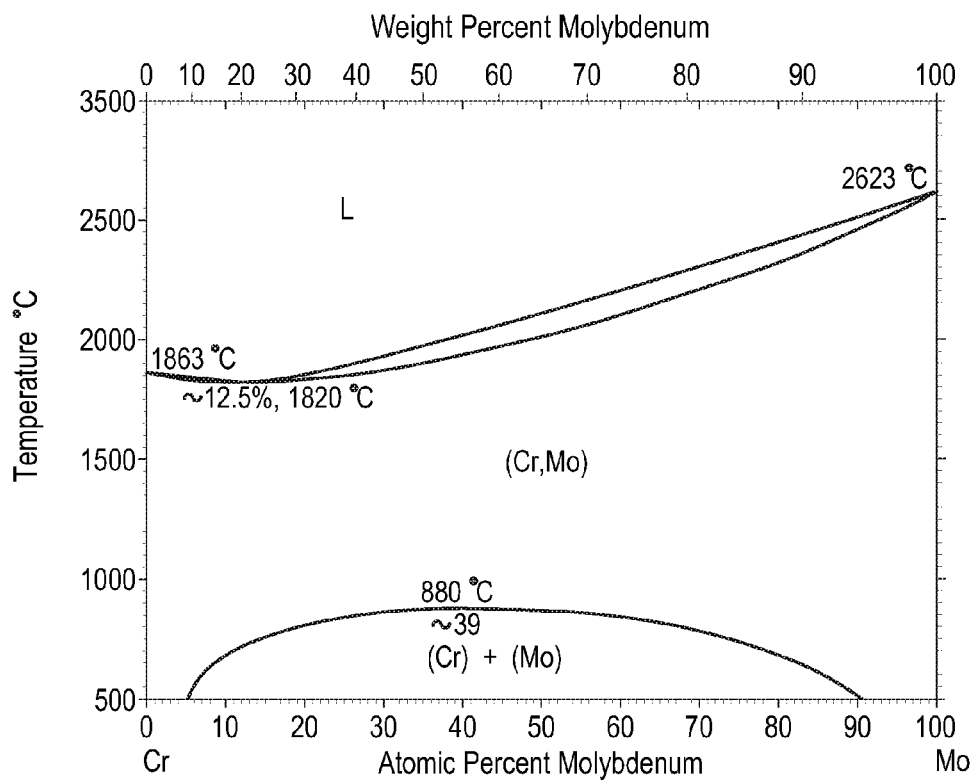
FIGS. 25A and 25B show a phase diagram for chromium-molybdenum.
Figure 25B:
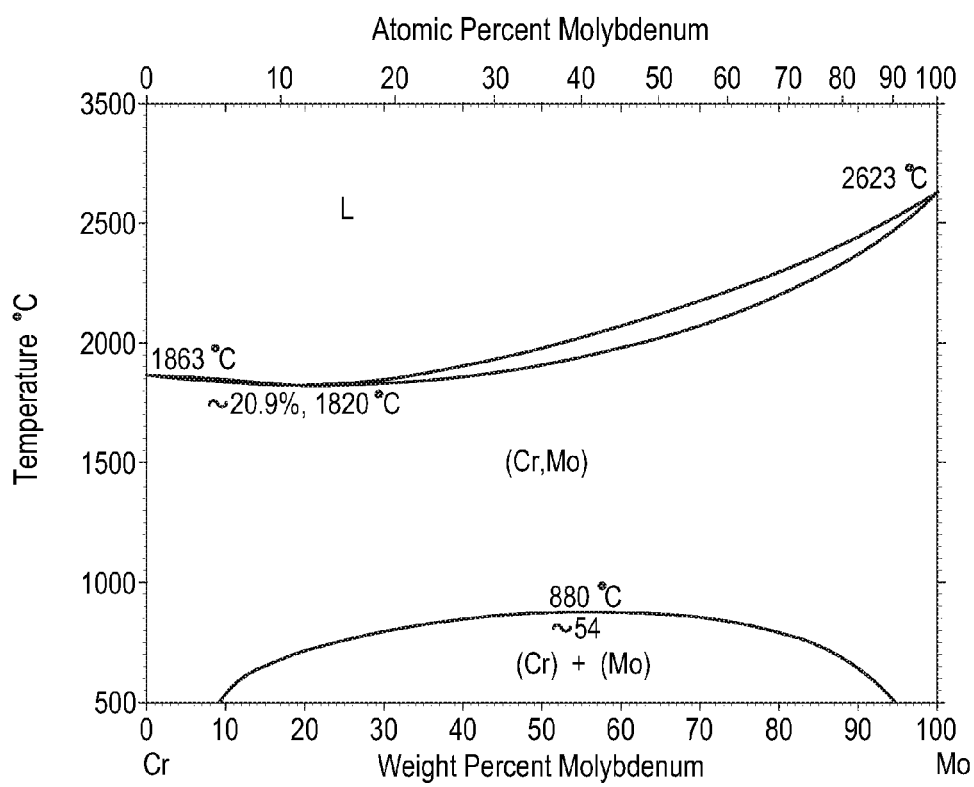

Cr—Mo phase diagram exhibits a miscibility gap from about 9Mo through about 95Mo. Based on the shape of the miscibility curve at 500° C., it is likely that this extends to close to 2Mo through 99+Mo at room/body temperature. This indicates that the microstructure will be a mixture of (Cr)+(Mo) BCC phases (FIGS. 25A-25B).

Figure 26A:
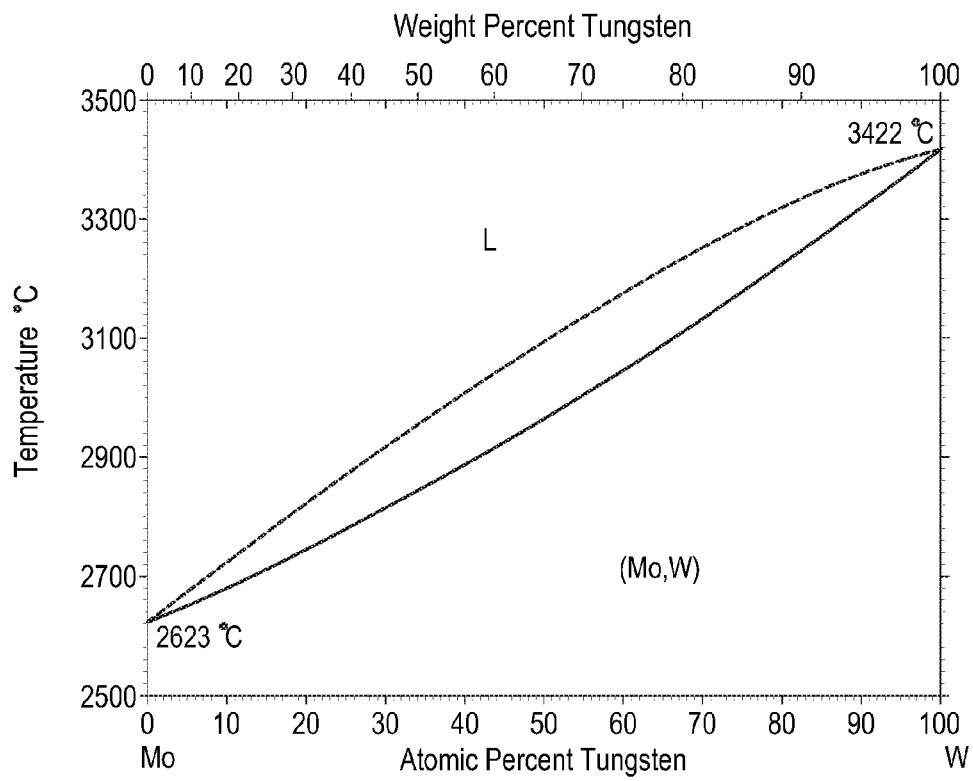
FIGS. 26A and 26B show a phase diagram for molybdenum-tungsten.
Figure 26B:
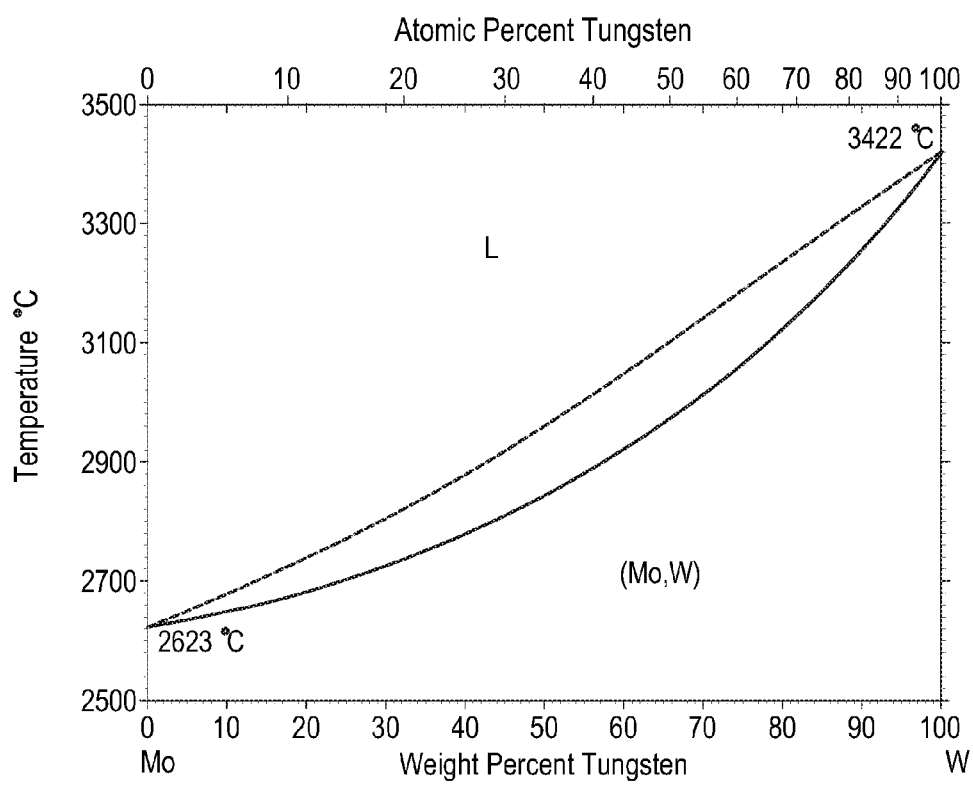

Mo—W phase diagram exhibits a continuous BCC solid solution (Mo,W) regardless of composition (FIGS. 26A-26B).

Figure 27A:
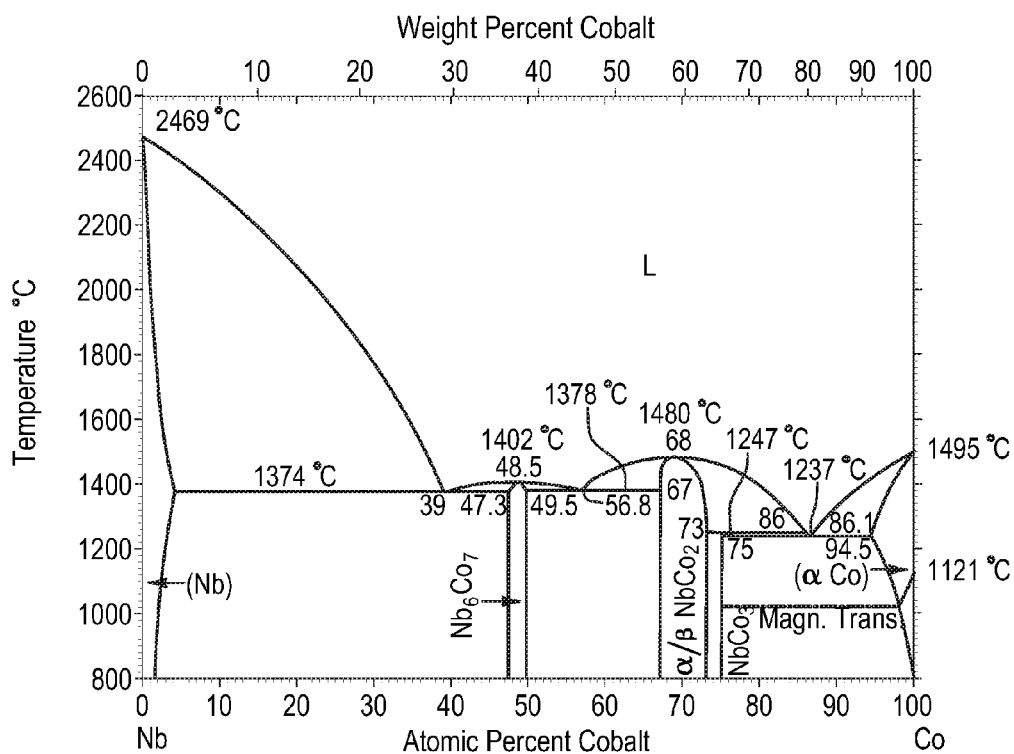
FIGS. 27A and 27B show a phase diagram for niobium-cobalt.
Figure 27B:
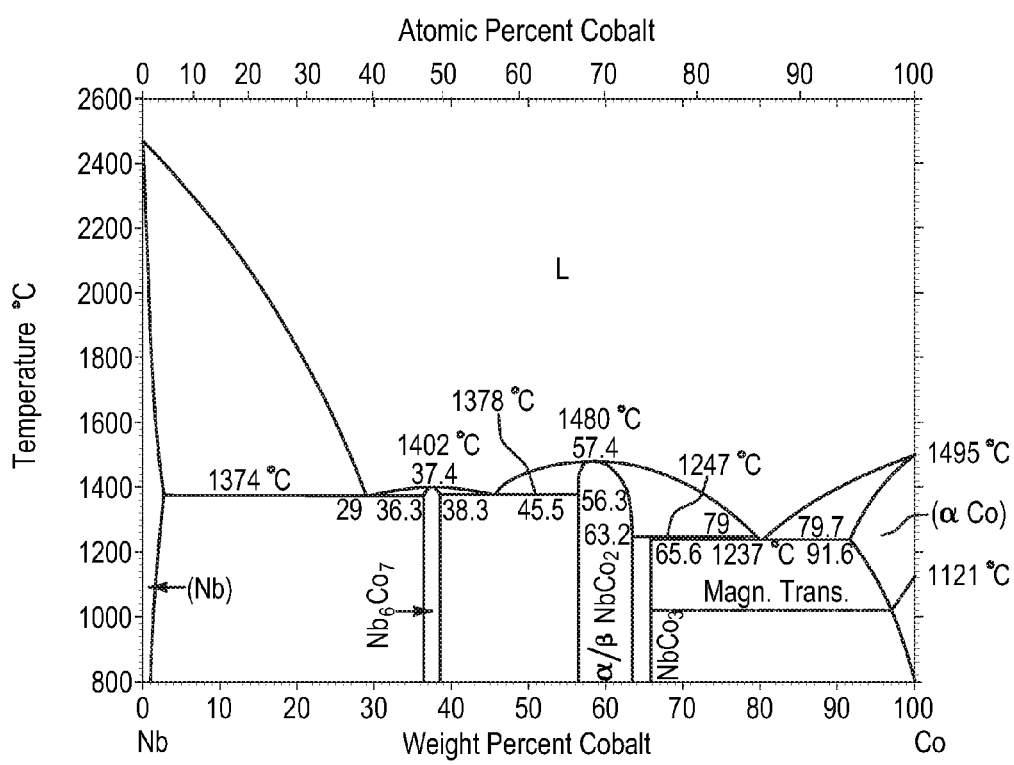

For an alloy containing Nb, considering different compositions that may as include Mo and/or W:

Co—Nb is a complex phase diagram with multiple eutectics and congruent ordered phases, including one phase specific to a single composition. These phases include an HCP NbCo$_3$ phase at about 34.5Nb, an FCC αNbCo$_2$ phase from about 37 to about 44Nb, and rhombohedral Nb$_6$Co$_7$ from about 61 to about 64Nb. Up to about 34.5Nb most likely is a mixture of HCP (εCo) and HCP NbCo$_3$. From about 34.5 to about 37Nb is a mixture of HCP NbCo$_3$ and FCC αNbCo$_2$ phases. From about 44 to about 61Nb is a mixture of FCC αNbCo$_2$ and rhombohedral Nb$_6$Co$_7$. Above about 64Nb is a mixture of rhombohedral Nb$_6$Co$_7$ and BCC (Nb) phases (FIGS. 27A-27B).

Figure 28A:
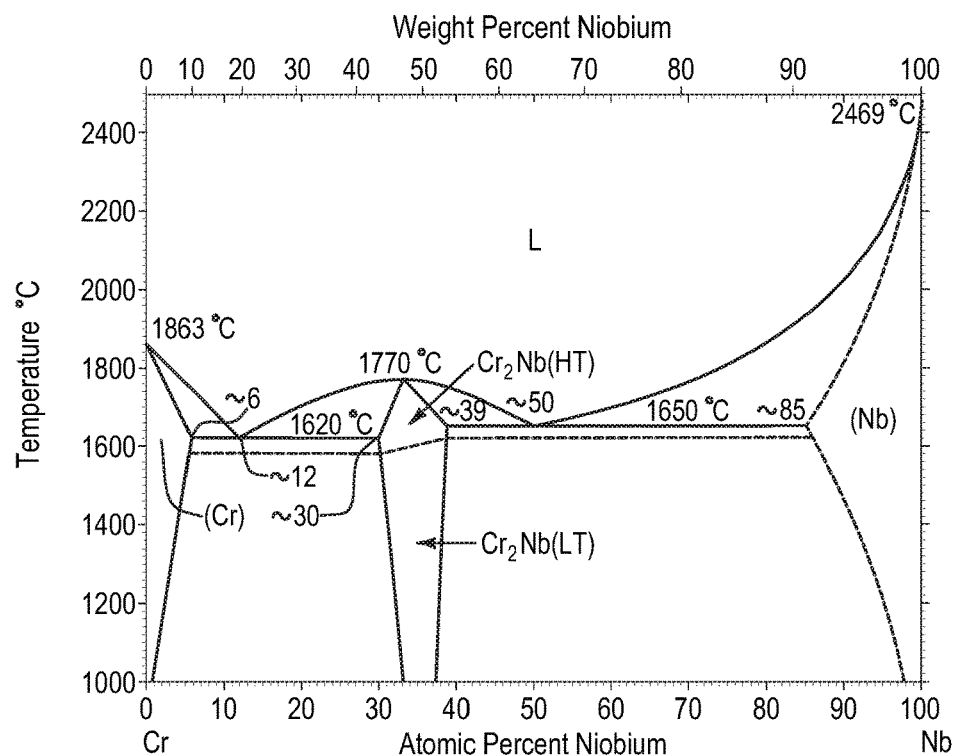
FIGS. 28A and 28B show a phase diagram for chromium-niobium.
Figure 28B:
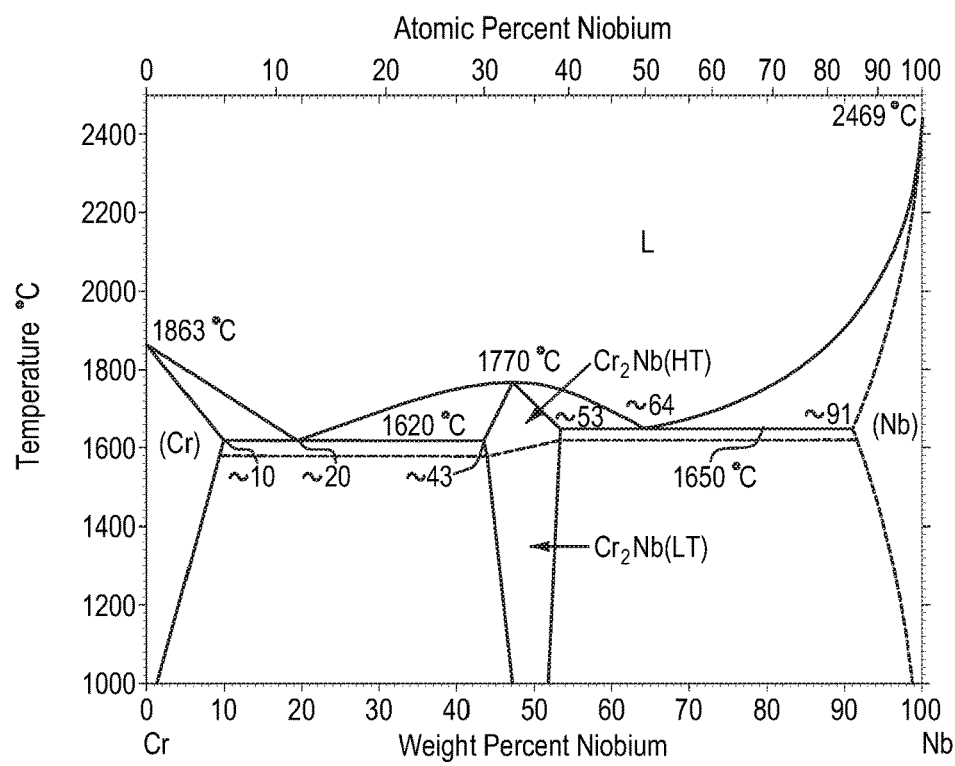

Cr—Nb shows two eutectics and a congruent ordered phase around the middle of the phase diagram. The ordered FCC Cr$_2$Nb phase falls from about 47 to about 52Nb. Up to about 47Nb exists a mix of BCC (Cr) and FCC Cr$_2$Nb phases. Above about 52Nb exists a mix of FCC Cr$_2$Nb and BCC (Nb) phases (FIGS. 28A-28B).

Figure 29A:
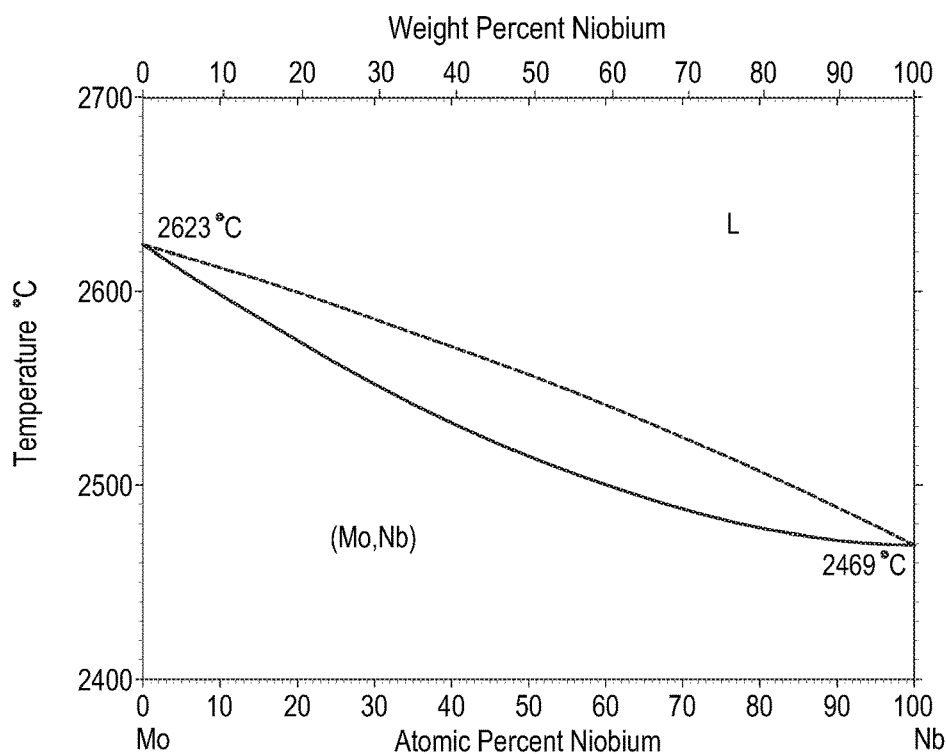
FIGS. 29A and 29B show a phase diagram for molybdenum-niobium.
Figure 29B:
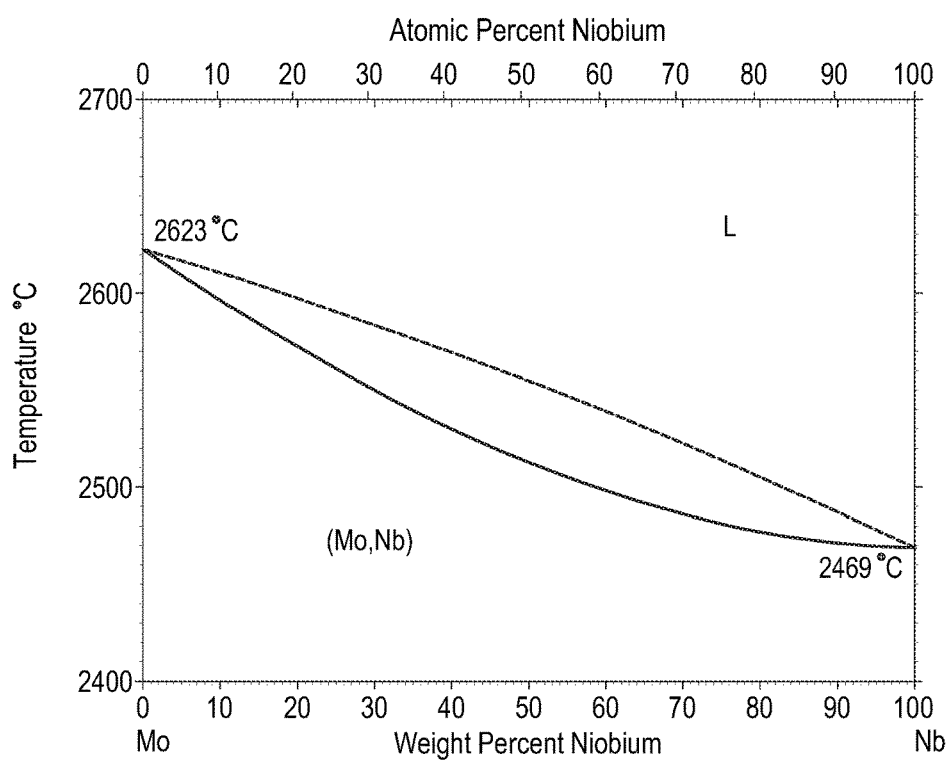

Mo—Nb phase diagram shows a single solid solution BCC (Mo,Nb) phase across the entire range of compositions (FIGS. 29A-29B).

Figure 30A:
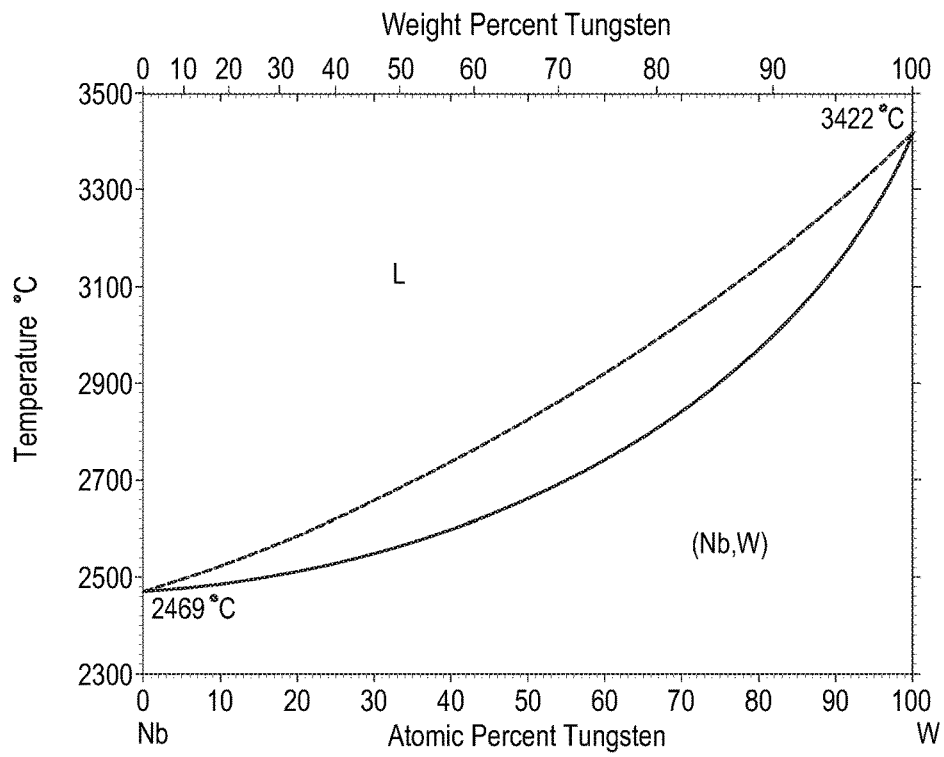
FIGS. 30A and 30B show a phase diagram for niobium-tungsten.
Figure 30B:
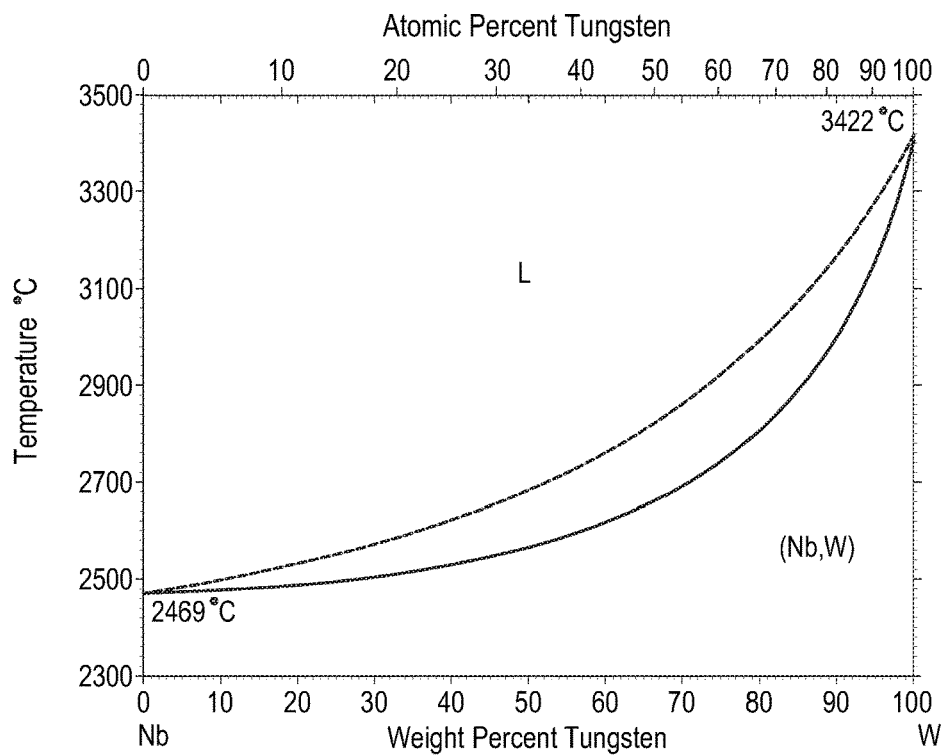

Nb—W phase diagram shows a single solid solution BCC (Nb,W) phase across the entire range of compositions (FIGS. 30A-30B).

Figure 31A:
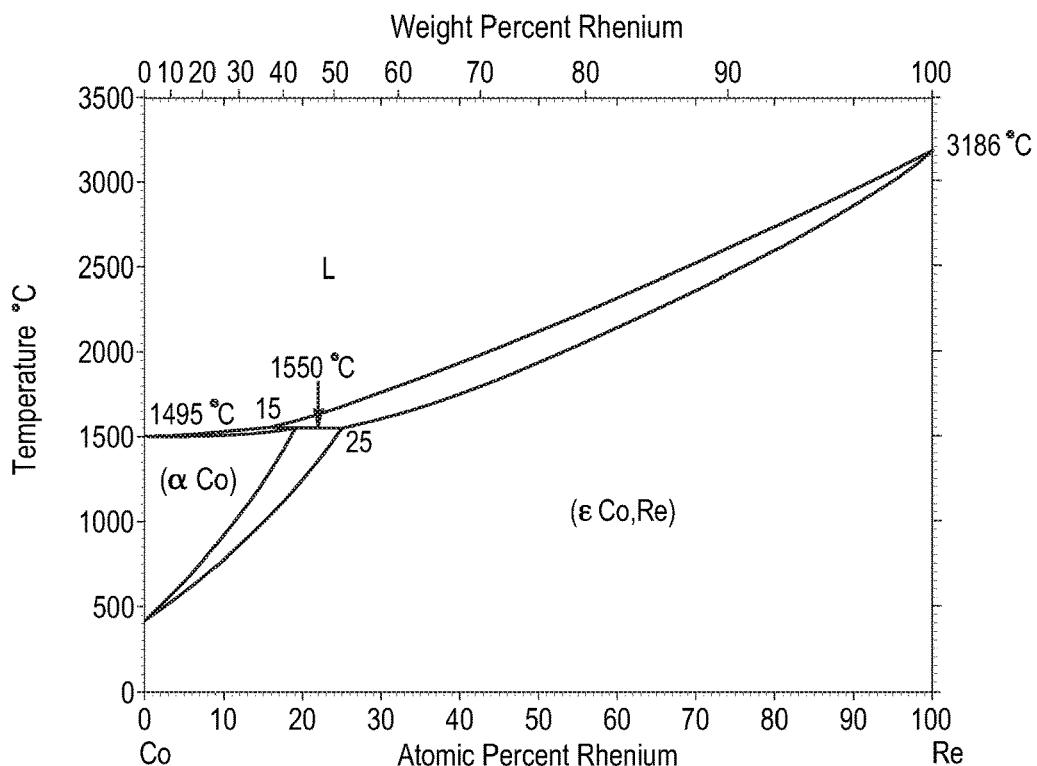
FIGS. 31A and 31B show a phase diagram for cobalt-rhenium.
Figure 31B:
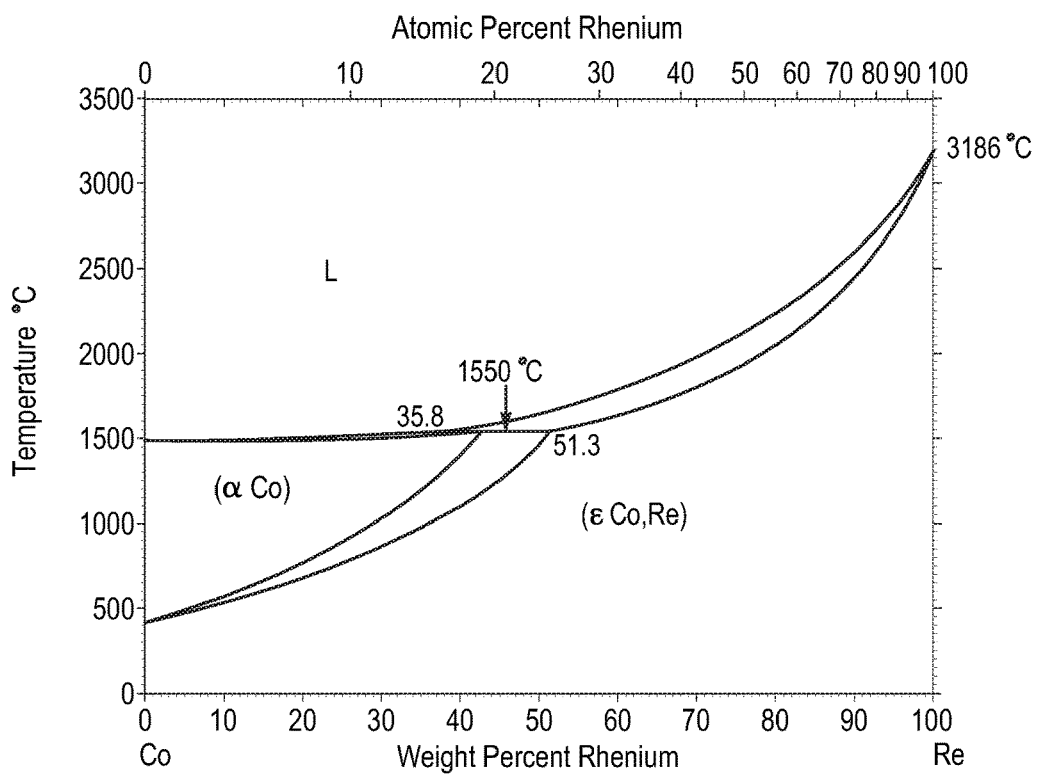

For an alloy containing Re, considering different compositions that may include Mo and/or W:

Co—Re forms an HCP solid solution phase of (εCo, Re) across the entire phase diagram at the temperatures of interest (FIGS. 31A-31B).

Figure 32A:
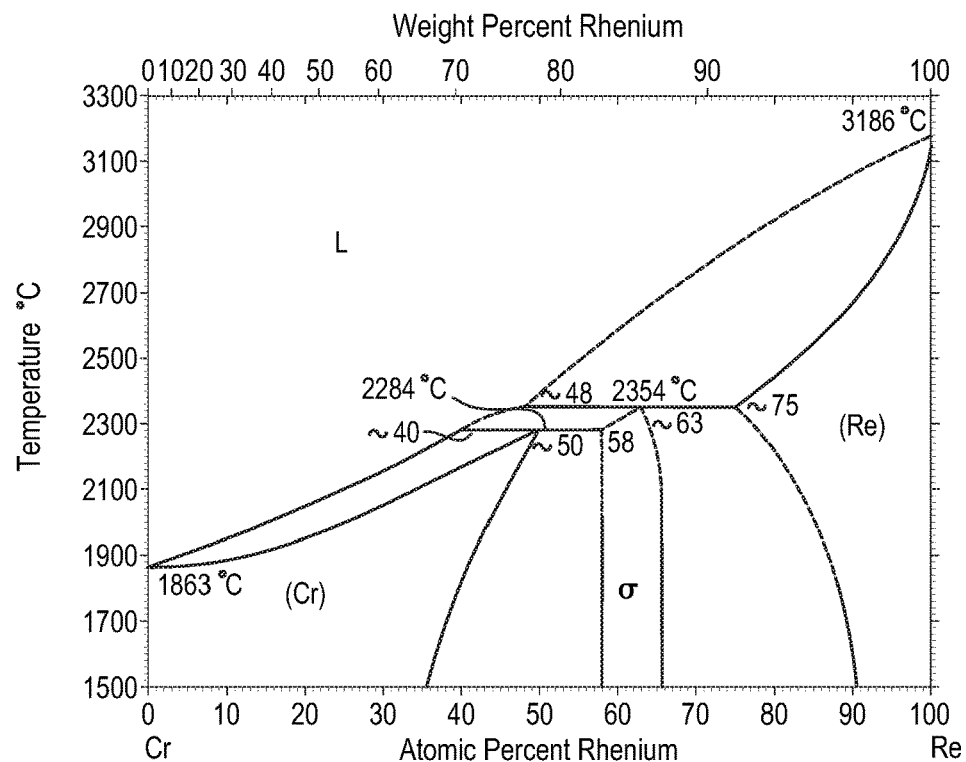
FIGS. 32A and 32B show a phase diagram for chromium-rhenium.
Figure 32B:
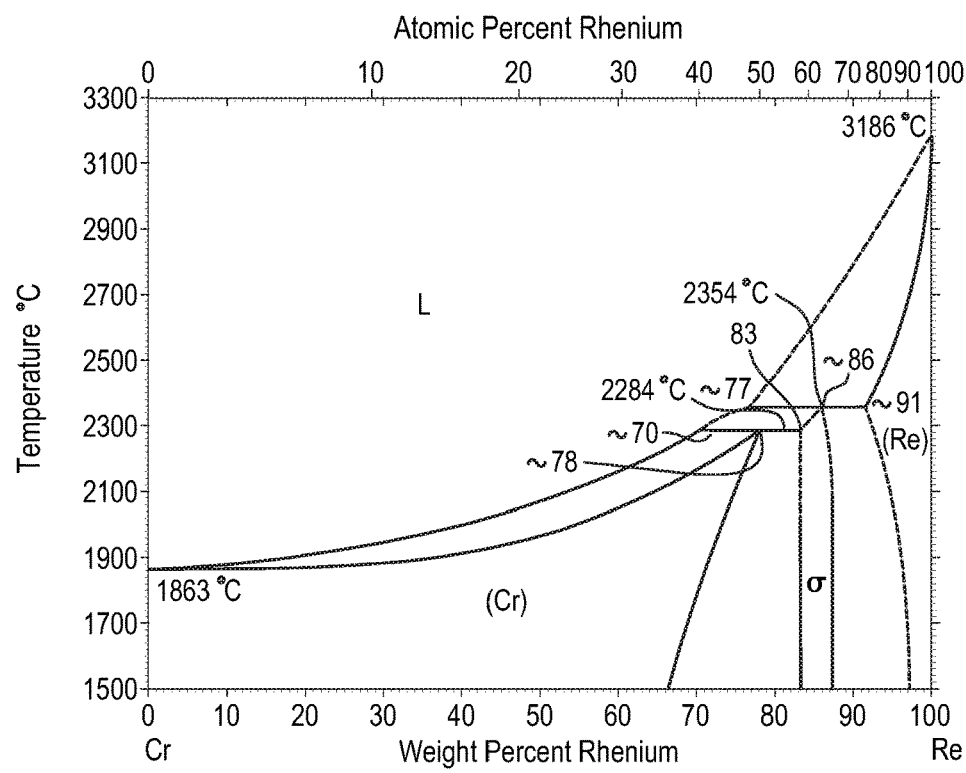

Cr—Re is a phase diagram with eutectic and peritectic reactions. Up to about 66Re the microstructure is primarily BCC (Cr). From about 66 to about 83Re is a mixture of BCC (Cr) and a phases. A tetragonal ordered phase (the σ phase, also written as Cr$_2$Re$_3$) forms from about 83 to about 88Re. Above about 88Re through about 97Re, a mixture of a and HCP (Re) phases exist. Above about 97Re, the dominant microstructure is HCP (Re) (FIGS. 32A-32B).

Figure 33A:
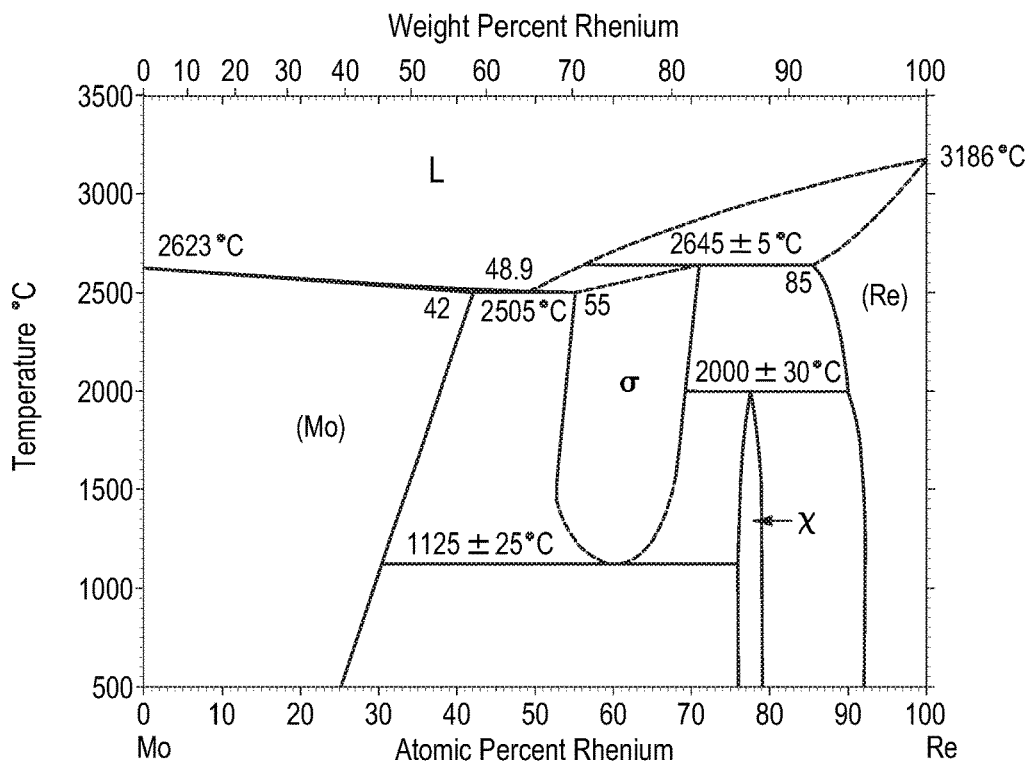
FIGS. 33A and 33B show a phase diagram for molybdenum-rhenium.
Figure 33B:
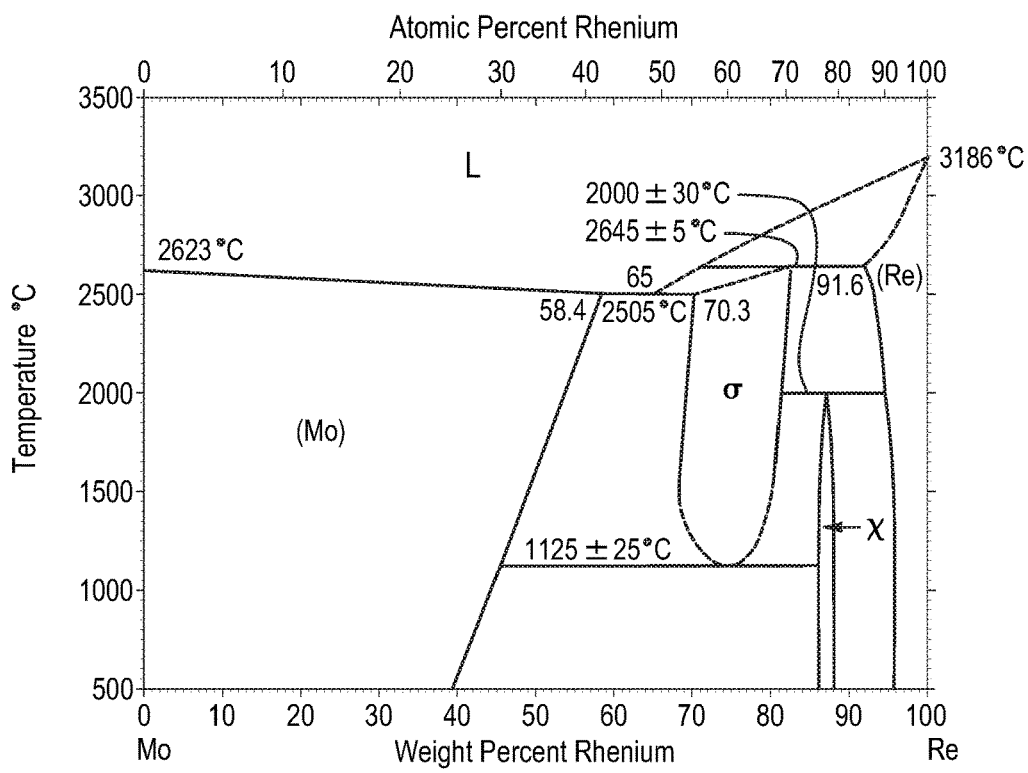

Mo—Re phase diagram is a combination of a eutectic, congruent, peritectoid, and allotropic phase transformation. Up to about 38Re a BCC (Mo) solid solution phase exists. From about 28Re to about 86Re is a mix of BCC (Mo) and BCC χ phases. From about 86 to about 88Re is the ordered BCC χ phase. From about 88 to about 95.5Re a combination of BCC χ and HCP (Re) phases exist. Above about 96 relative weight percent the structure is a solid solution HCP (Re) phase (FIGS. 33A-33B).

Figure 34A:
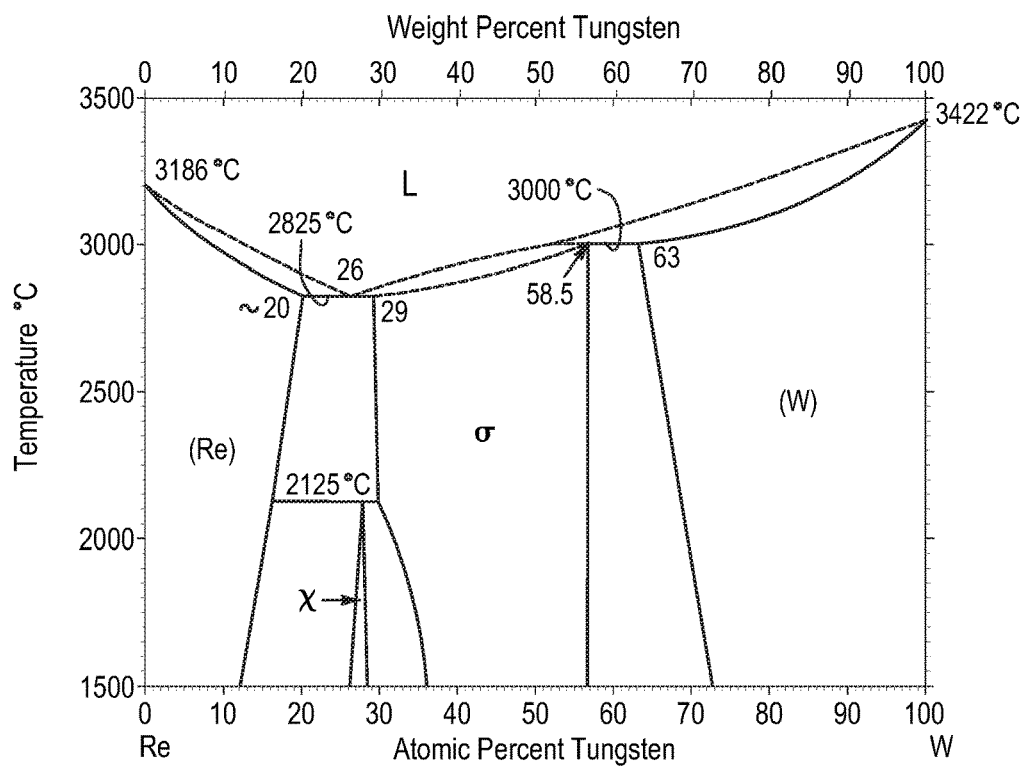
FIGS. 34A and 34B show a phase diagram for rhenium-tungsten.
Figure 34B:
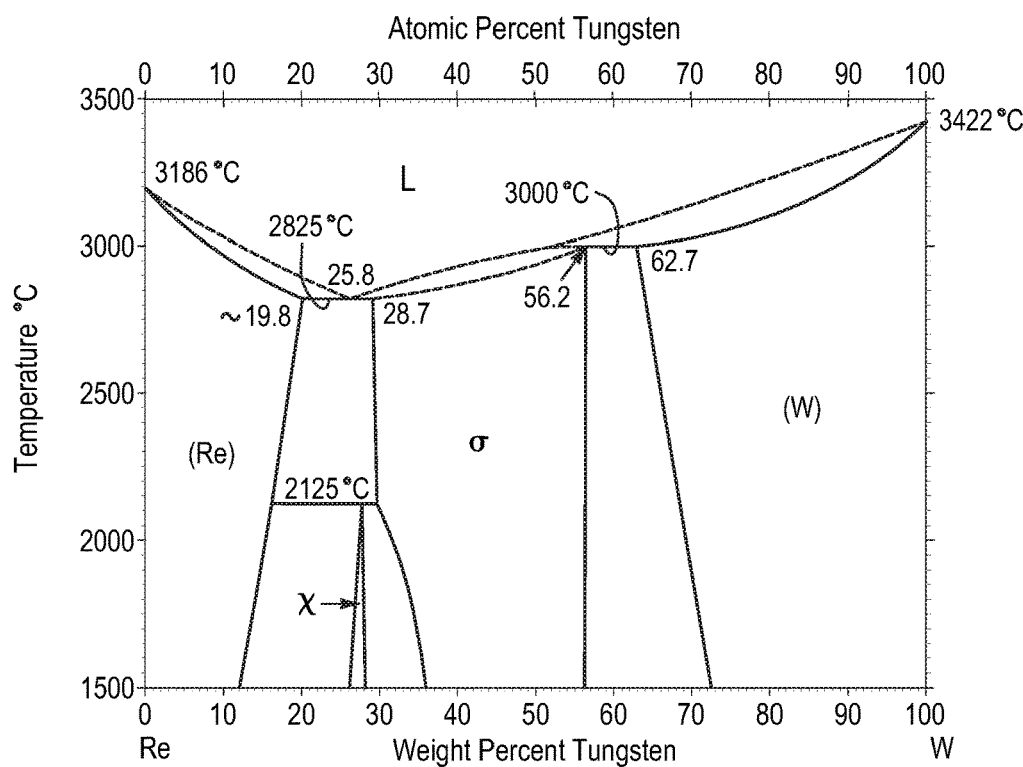

Re—W is a complex phase diagram with eutectic, peritectoid, and congruent features. Up to about 28Re is a solid solution BCC (W) phase. From about 28 to about 44Re is a combination of BCC (W) and tetragonal σ phases. From about 44 to about 64Re is the ordered tetragonal σ phase. From about 64 to about 72Re is a combination of tetragonal σ and BCC χ phases. From about 72 to about 74Re is the ordered BCC χ phase. From about 74 to about 88Re is a combination of BCC χ and HCP (Re) phases. Above about 88Re, a HCP solid solution phase with W exists (FIGS. 34A-34B).

Figure 35A:
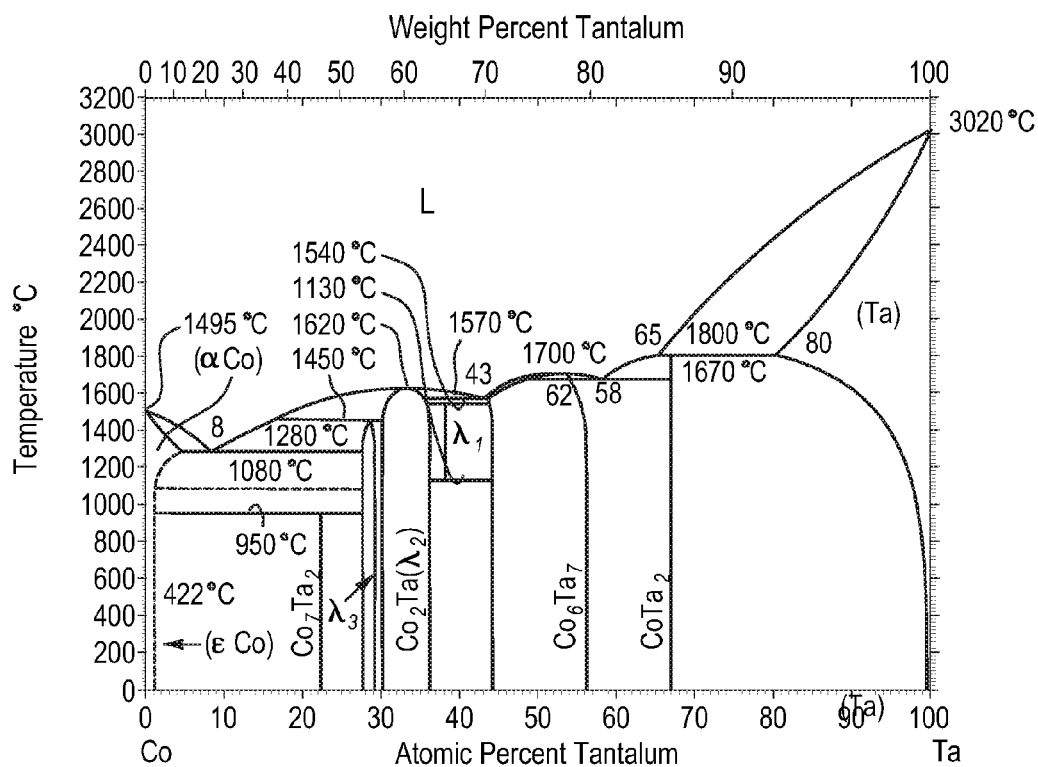
FIGS. 35A and 35B show a phase diagram for cobalt-tantalum.
Figure 35B:
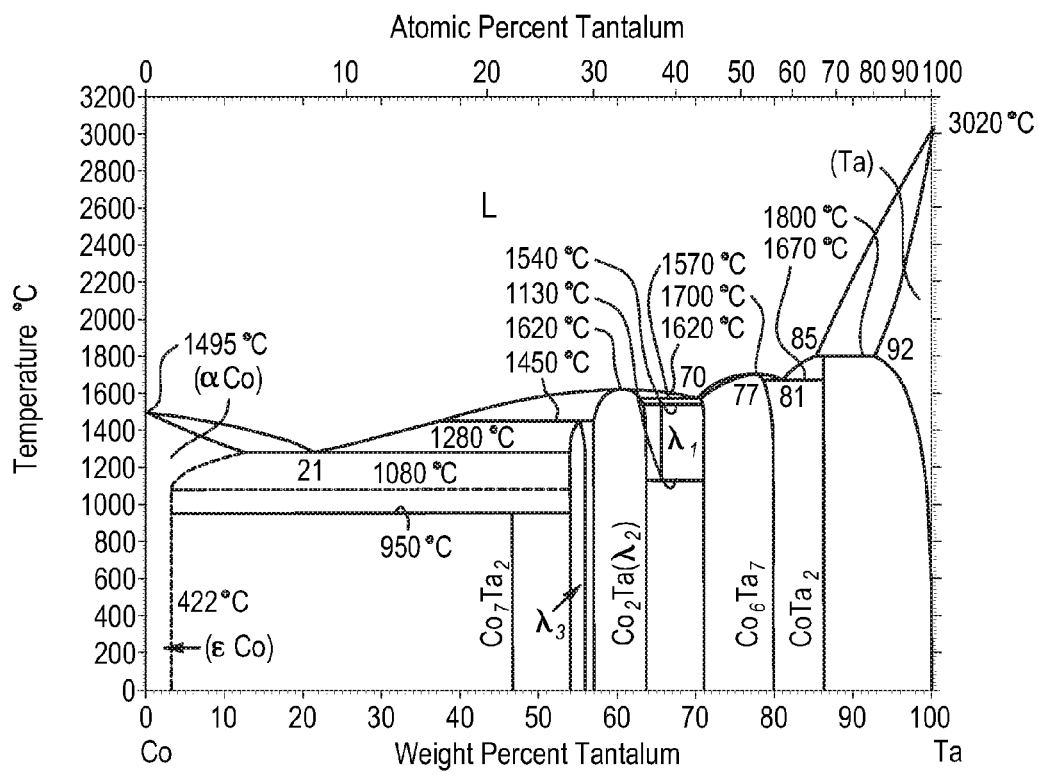

For an alloy containing Ta, considering different compositions that may include Mo and/or W:

Co—Ta is a fairly complex phase diagram that exhibits five ordered phases, three of which are peritectic. Up to about 3Ta is HCP (εCo). From about 3 to about 46.5Ta is a mixture of HCP (εCo) and Co$_7$Ta$_2$ (unknown microstructure). The Co$_7$Ta$_2$ phase sits at about 46.5Ta. From about 46.5 to about 54Ta is a combination of Co$_7$Ta$_2$ and HCP λ$_3$ phases. The HCP λ$_3$ phase sits from about 54 to about 55.5Ta. From about 55.5 to 57Ta is a mixture of HCP λ$_3$ and FCC Co$_2$Ta (λ$_2$) phases. From about 57 to about 63Ta is the FCC Co$_2$Ta (λ$_2$) phase. From about 63 to about 70.5Ta is mixture of FCC Co$_2$Ta (λ$_2$) and rhombohedral Co$_6$Ta$_7$ phases. From about 70.5 to 79.5Ta is the Co$_6$Ta$_7$ rhombohedral phase. From about 79.5 to about 86Ta is a mixture of rhombohedral Co$_6$Ta$_7$ and BCT CoTa$_2$ phases. A BCT CoTa$_2$ phase sits at around 86Ta. Above about 85Ta is a mixture of BCT CoTa$_2$ and BCC (Ta) phases (FIGS. 35A-35B).

Figure 36A:
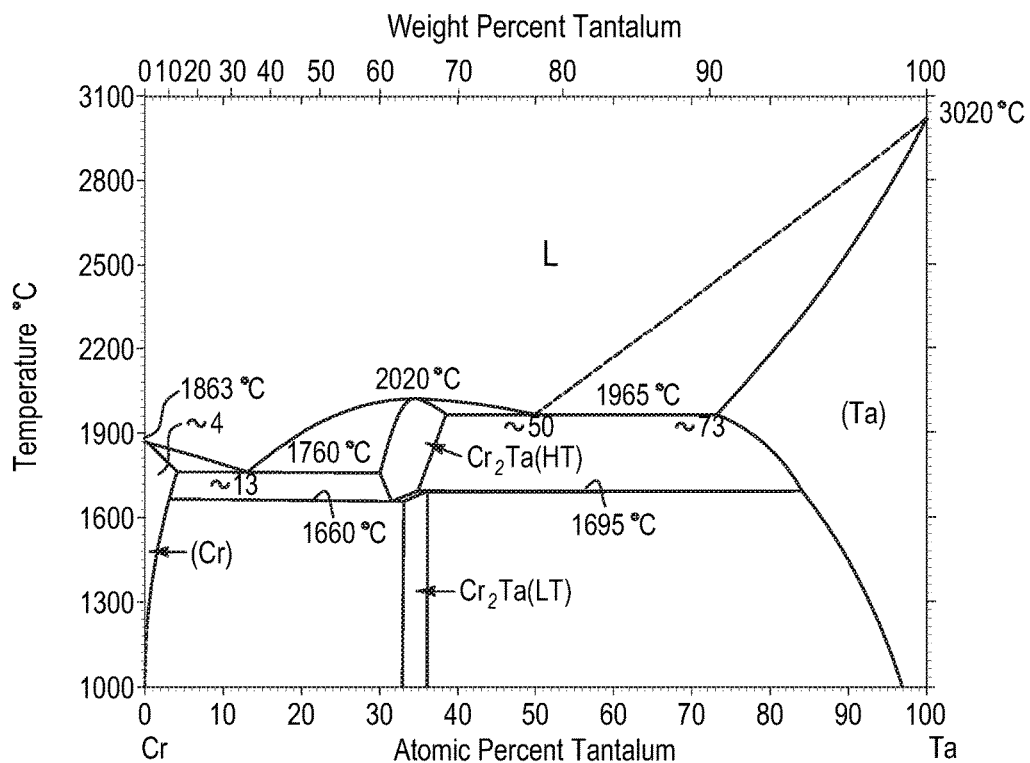
FIGS. 36A and 36B show a phase diagram for chromium-tantalum.
Figure 36B:
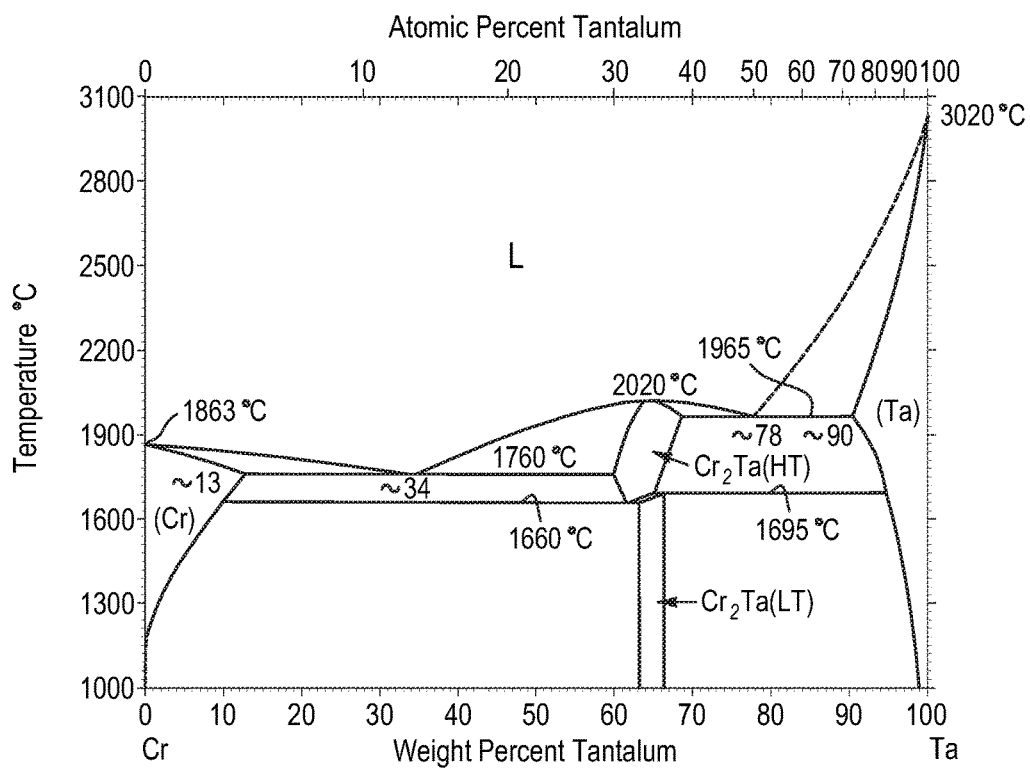

Cr—Ta is a phase diagram with a single intermediate phase that forms a eutectic with each of the (Cr) and (Ta) solid solutions. The intermediate Laves phase formation of FCC Cr$_2$Ta sits from about 63 to about 66.5Ta. Up to about 63Ta, the microstructure is a mixture of BCC (Cr) and FCC Cr$_2$Ta. Above about 66.5Ta is a mixture of FCC Cr$_2$Ta and BCC (Ta) (FIGS. 36A-36B).

Figure 37A:
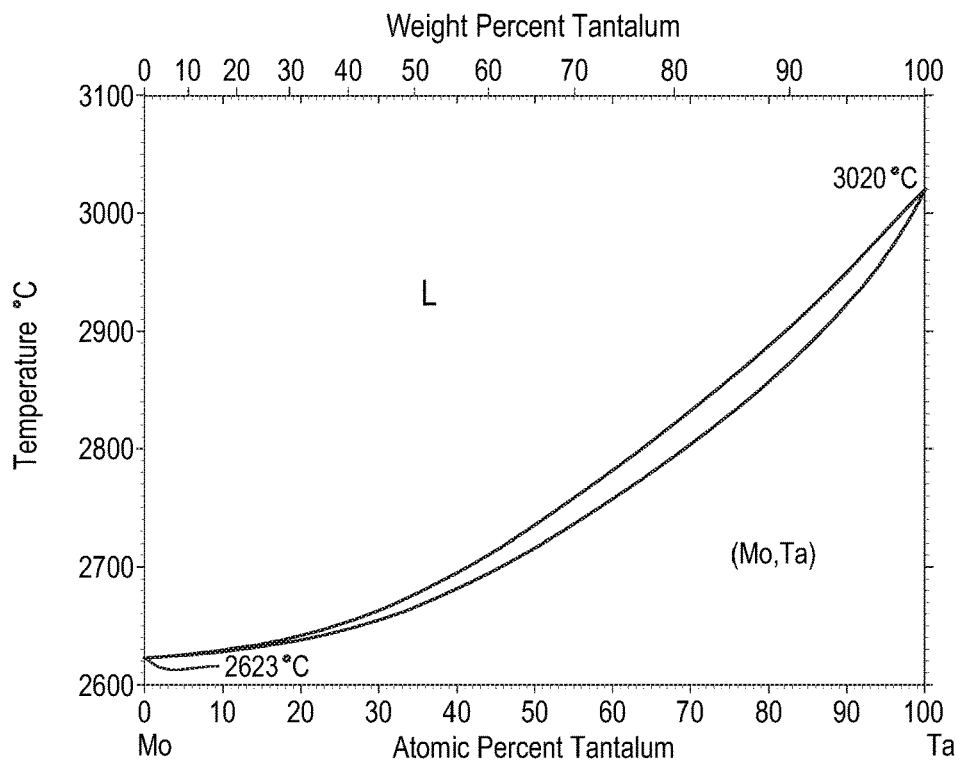
FIGS. 37A and 37B show a phase diagram for molybdenum-tantalum.
Figure 37B:
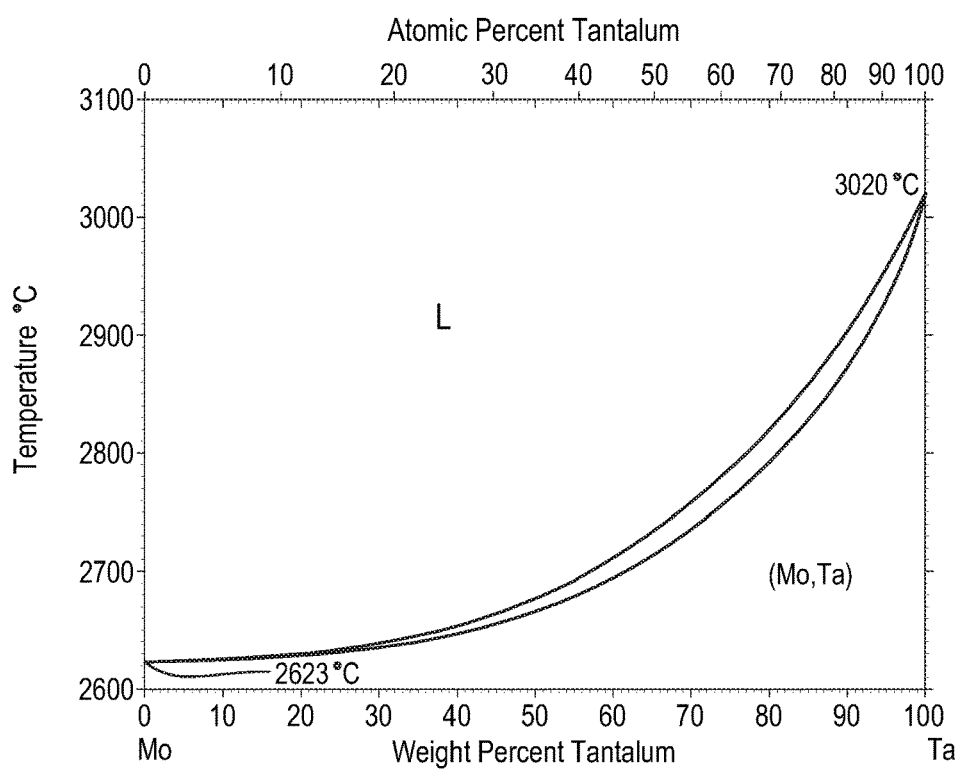

Mo—Ta forms a continuous BCC (Mo,Ta) solid solution at all compositions (FIGS. 37A-37B).

Figure 38A:
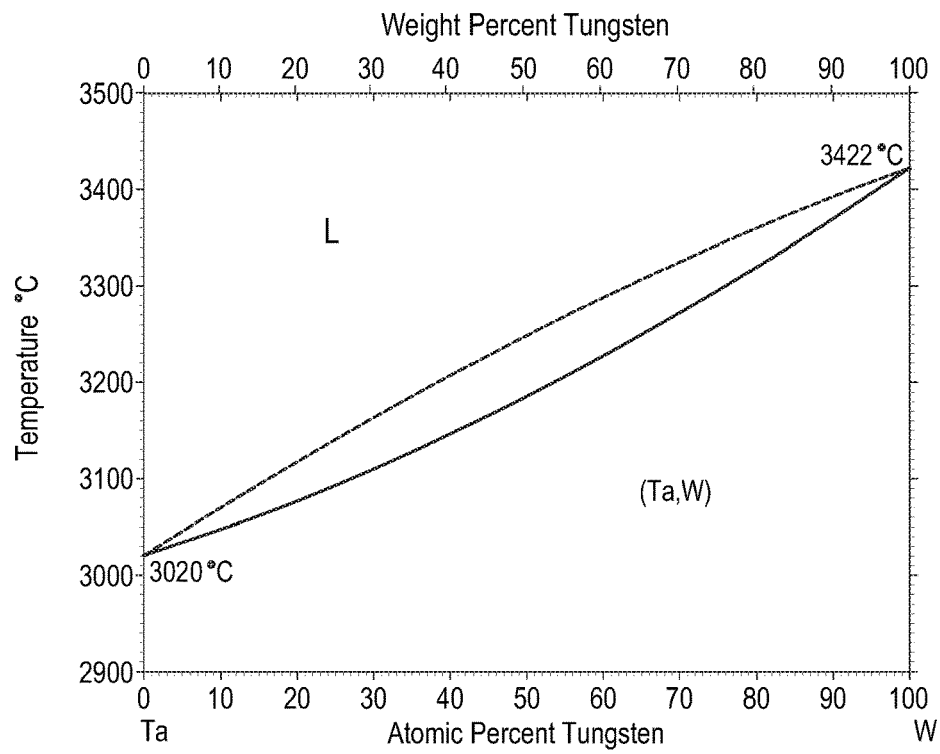
FIGS. 38A and 38B show a phase diagram for tantalum-tungsten.
Figure 38B:
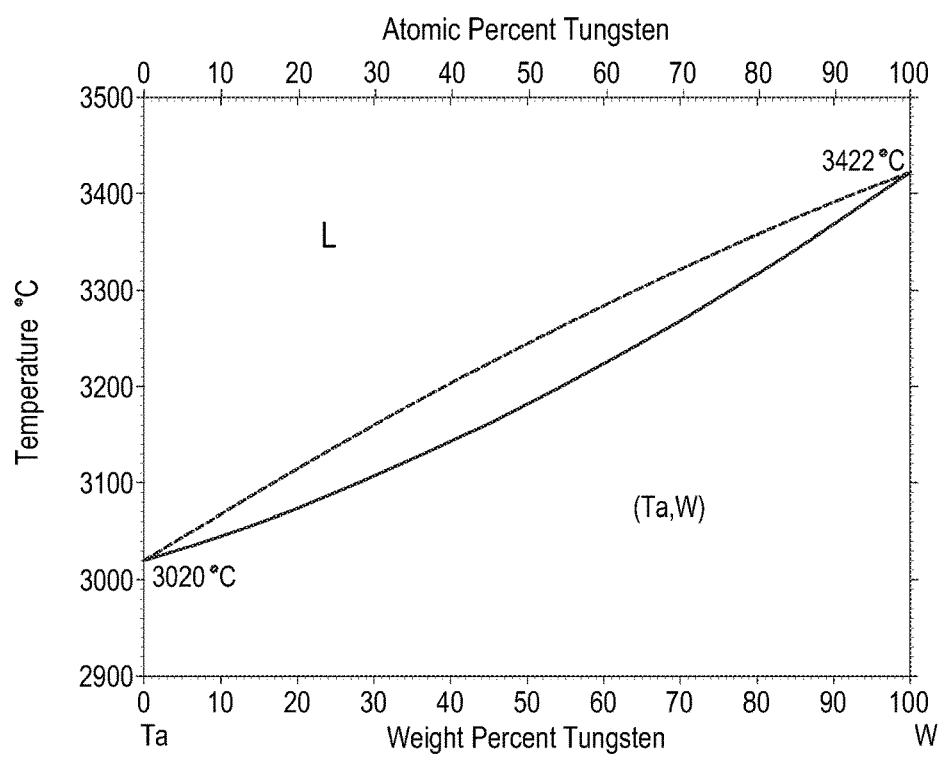

Ta—W forms a continuous BCC (Ta,W) solid solution at all compositions (FIGS. 38A-38B).

Figure 39A:
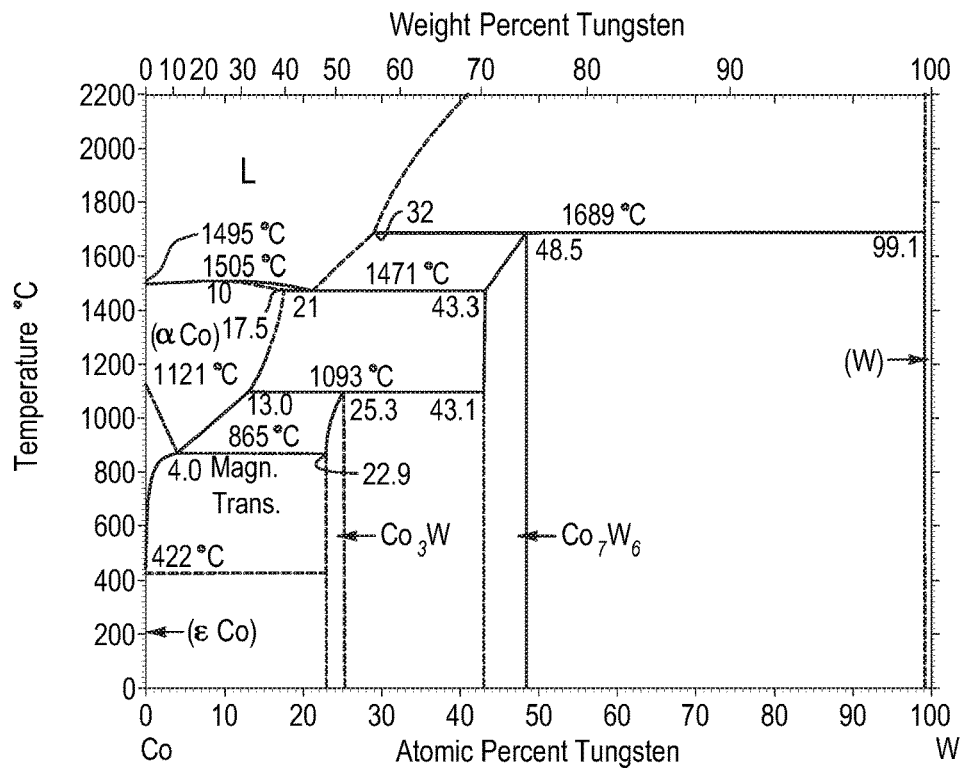
FIGS. 39A and 39B show a phase diagram for cobalt-tungsten.
Figure 39B:
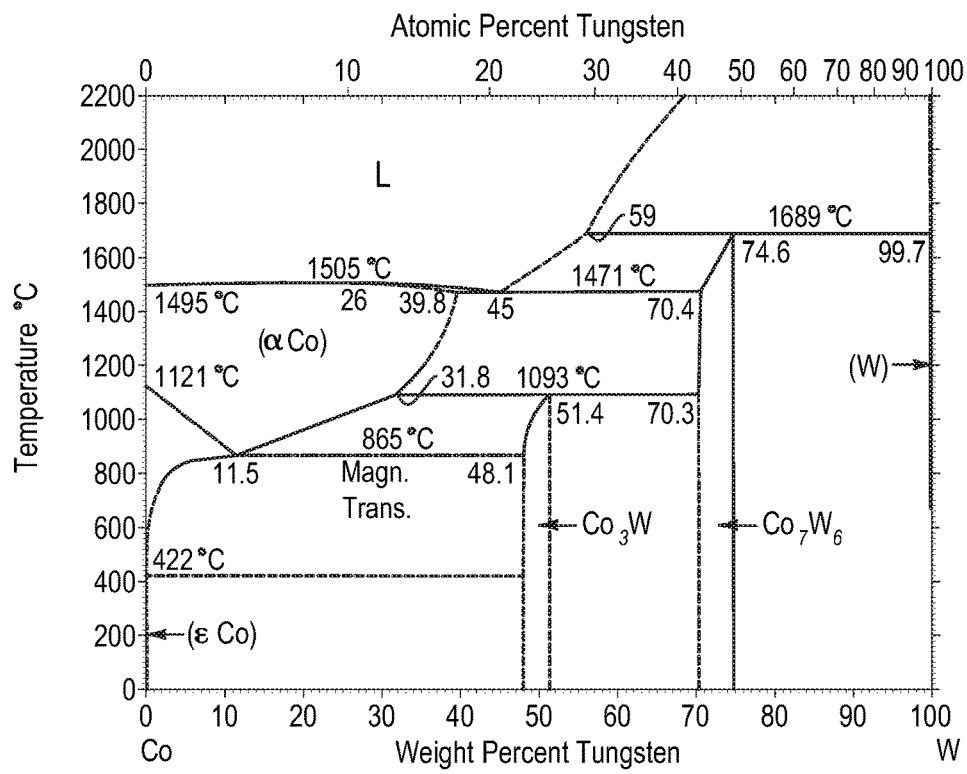

For an alloy containing W, the following may be observed:

Co—W is an extremely complex phase diagram with eutectic, eutectoid, peritectoid, and allotropic transformations featuring two different ordered phases at the temperatures of interest. HCP Co$_3$W forms from about 48 to about 51.5W. Rhombohedral Co$_7$W$_6$ forms from about 70 to about 74.5W. Up to about 48W the microstructure is a mixture of HCP (εCo) and HCP Co$_3$W phases. From about 51.5 to about 70W, the microstructure is a mixture of HCP Co$_3$W and rhombohedral Co$_7$W$_6$ phases. Above about 74.5W is a mixture of rhombohedral Co$_7$W$_6$ and BCC (W) phases. Based on the L-605 information and the similar MP-35N Co—Mo information, alloys that fall outside of the ordered phases allow for a workable alloy (FIGS. 39A-39B).

Figure 40A:
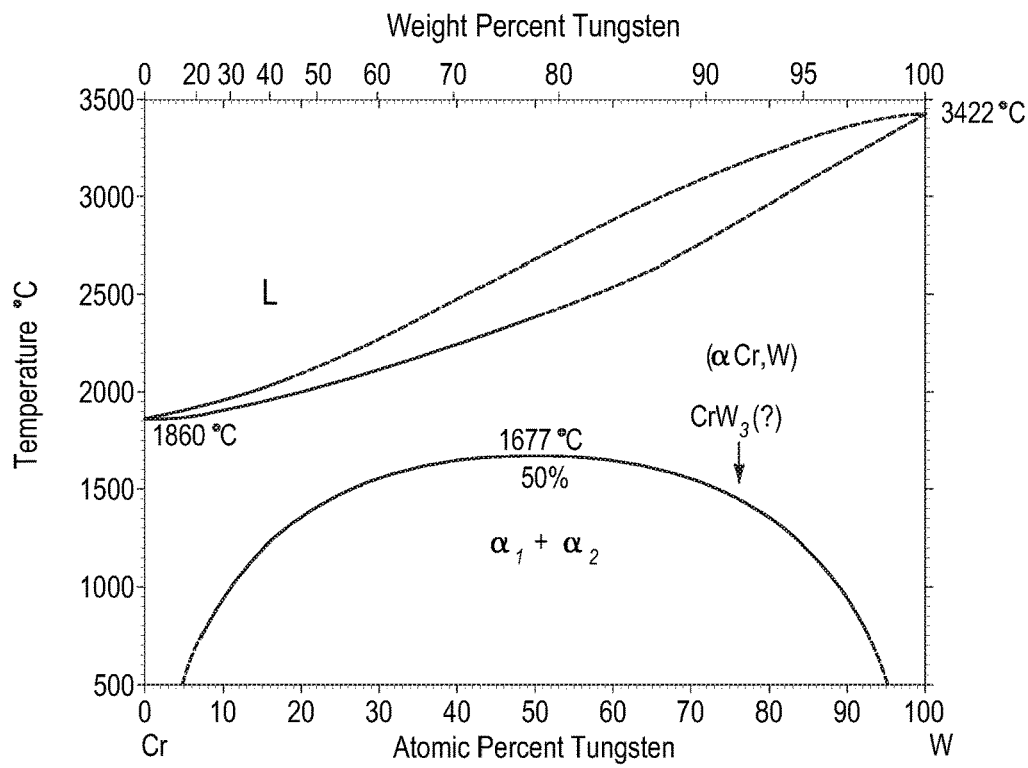
FIGS. 40A and 40B show a phase diagram for chromium-tungsten.
Figure 40B:
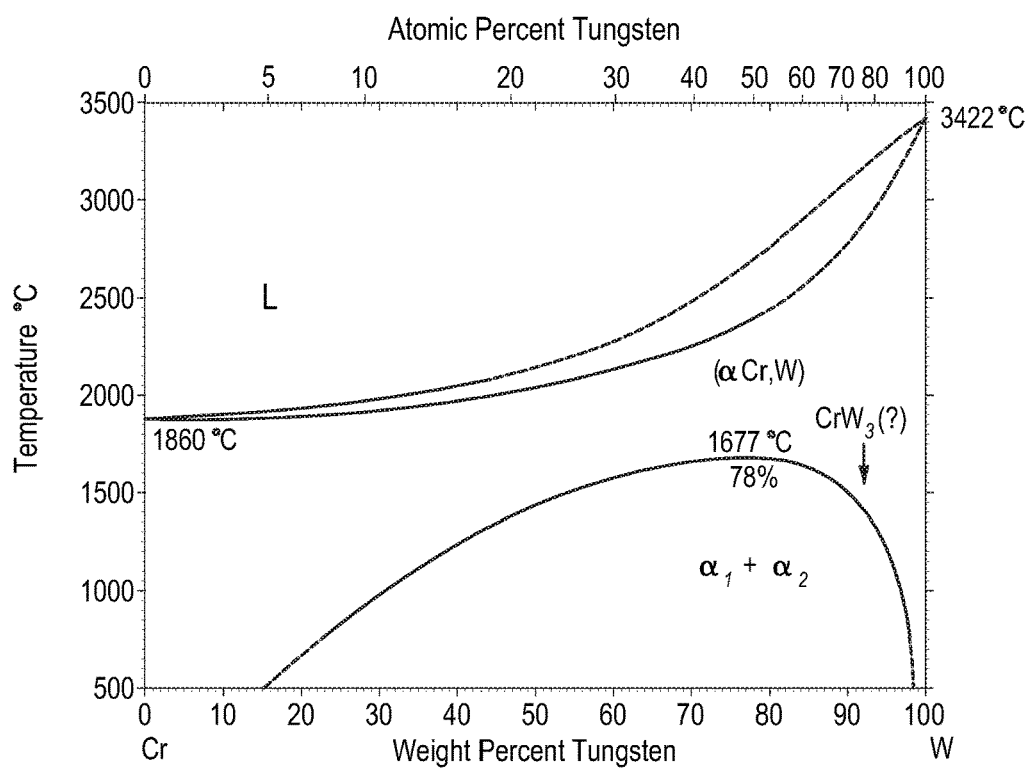

Cr—W is a phase diagram with a large miscibility gap starting around 15 weight percent W. Note that the miscibility gap most likely starts closer to 0-1W at the temperatures of interest, based on the shape of the curve. Below the start of the miscibility gap is a solid solution of BCC (Cr,W). Within the miscibility gap the two BCC ($\alpha_1+\alpha_2$) Cr and W phases exist (FIGS. 40A-40B).

Figure 41A:
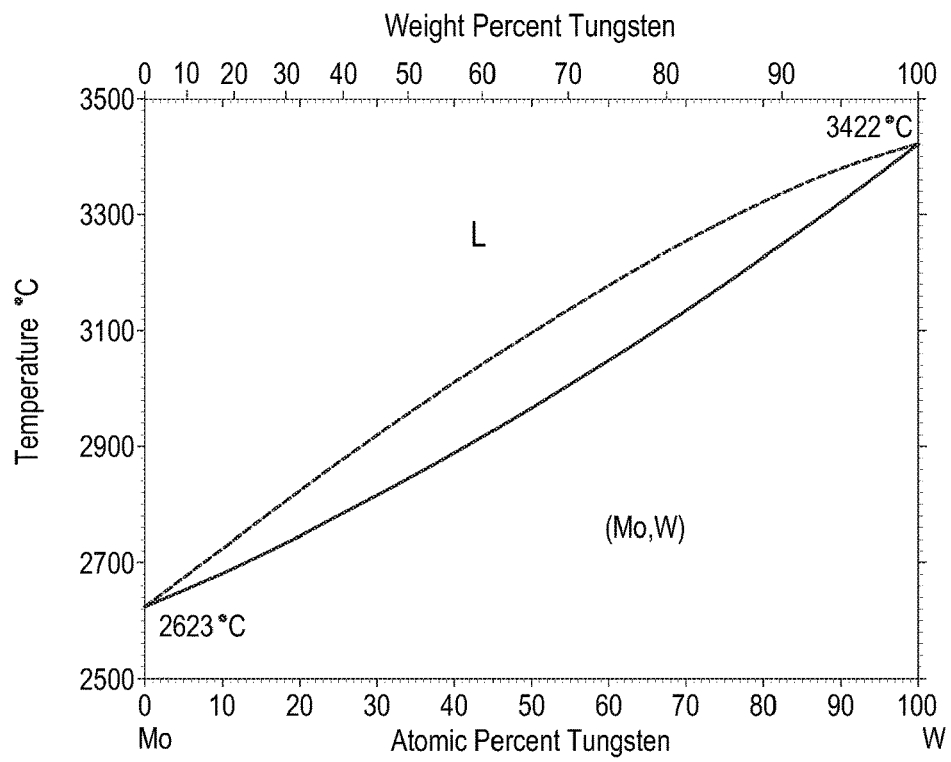
FIGS. 41A and 41B show a phase diagram for molybdenum-tungsten.
Figure 41B:
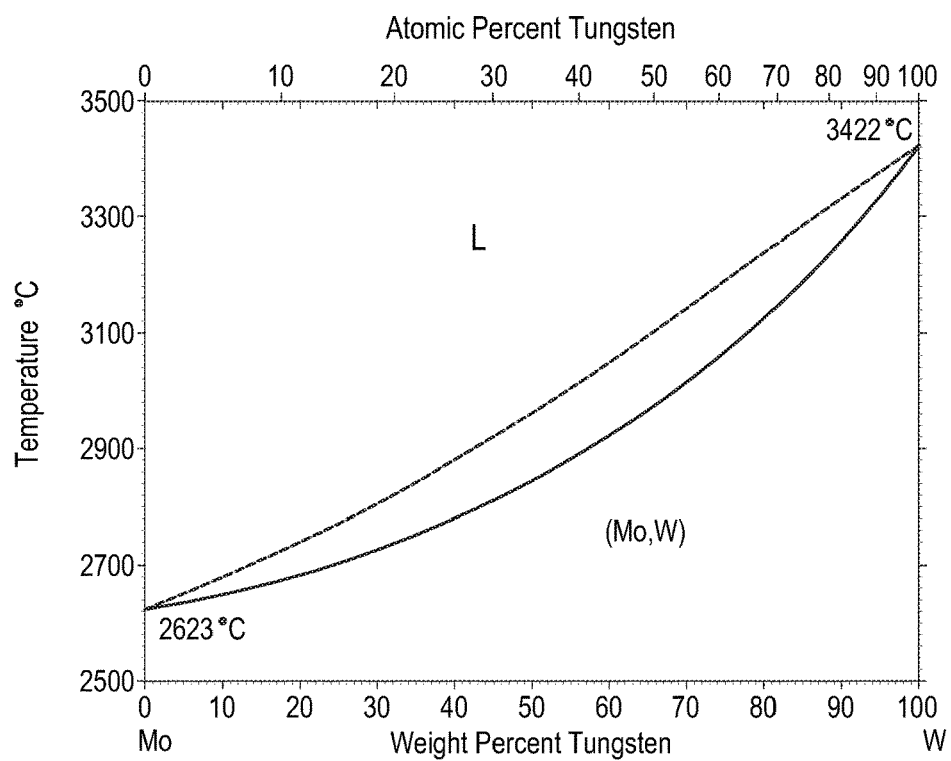

Mo—W forms a continuous BCC (Mo,W) solid solution at all compositions (FIGS. 41A-41B).

Figure 42A:
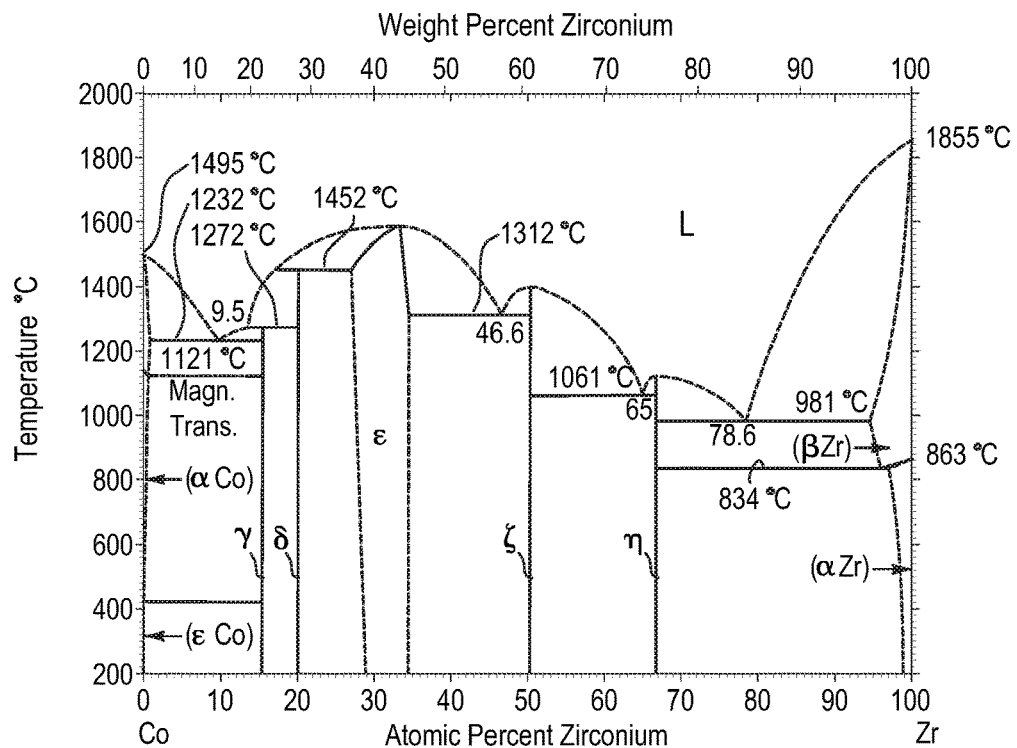
FIGS. 42A and 42B show a phase diagram for cobalt-zirconium.
Figure 42B:
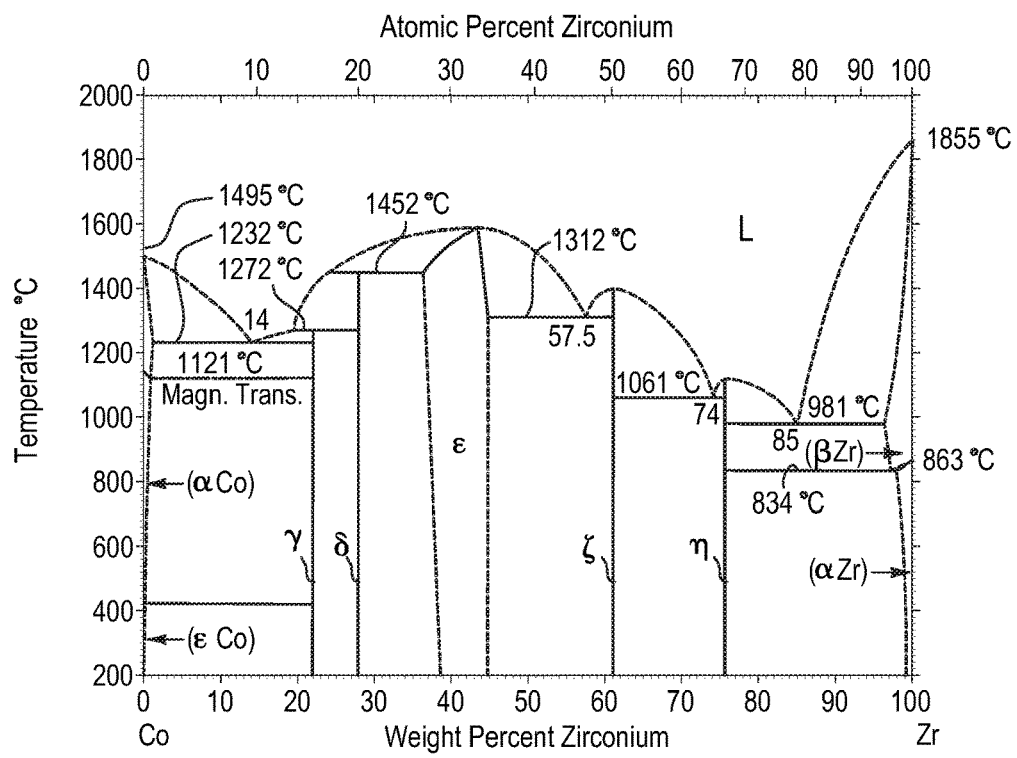

For an alloy containing Zr, the following may be observed:

Co—Zr is a complex phase diagram with eutectic, eutectoid, peritectic, and allotropic transformations. The formation of five different ordered phases are shown. The γ phase, of unknown structure, is at about 22Zr. The FCC δ phase appears at about 28Zr. The FCC ε phase appears roughly from about 39 to about 45Zr. The cubic ζ phase appears at about 61Zr. The BCT η phase appears at about 75.5Zr. Up to about 22Zr, the microstructure is a combination of HCP (εCo) and FCC γ phases. From about 22 to about 28Zr is a mixture of FCC γ and FCC δ phases. From about 28 to about 39Zr is a mixture of FCC δ and FCC ε phases. From about 45 to about 61Zr is a mixture of FCC ε and cubic ζ phases. From about 61 to about 75.5Zr is a mixture of cubic ζ and BCT η phases. From about 75.5 to about 99Zr is a mixture of BCT η phase and HCP (αZr) phases. Above 99Zr is a solid solution HCP (αZr) phase (FIGS. 42A-42B).

Figure 43A:
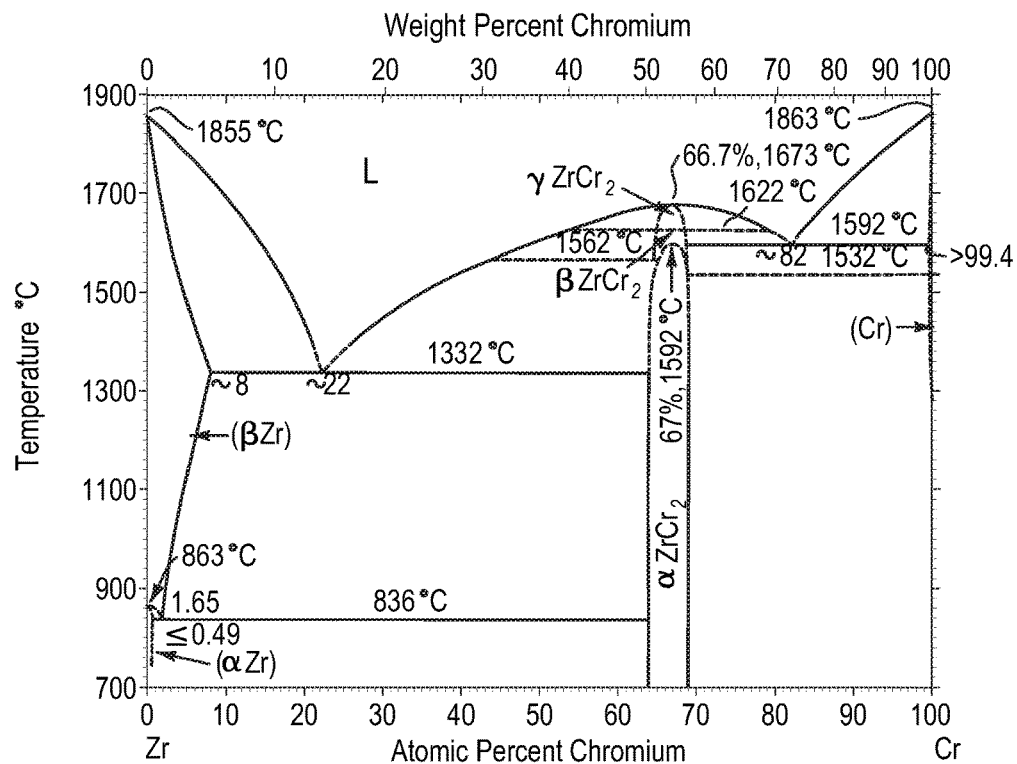
FIGS. 43A and 43B show a phase diagram for zirconium-chromium.
Figure 43B:
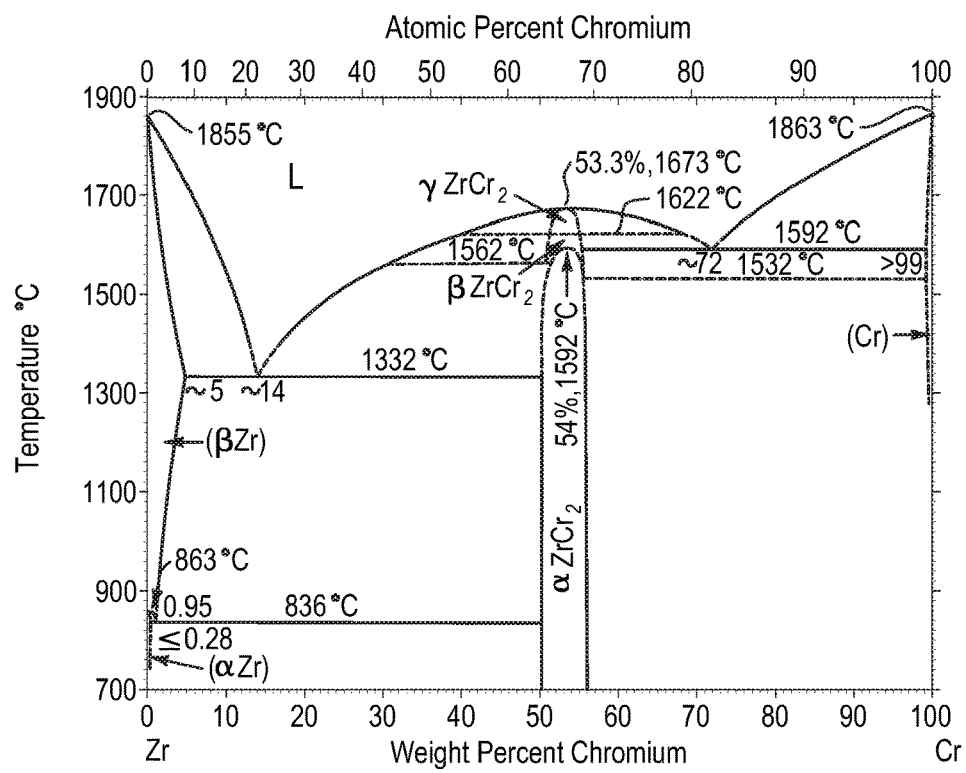

Cr—Zr is a complex phase diagram with eutectic, eutectoid, congruent and allotropic transformation features. One intermediate ordered phase exists at the temperature of interest. That FCC αZrCr$_2$ phase falls from about 44 to about 50Zr. Up to about 44Zr is a combination of BCC (Cr) and FCC αZrCr$_2$ phases. Above about 50Zr is a combination of FCC αZrCr$_2$ and HCP (αZr) phases (FIGS. 43A-43B).

Figure 44A:
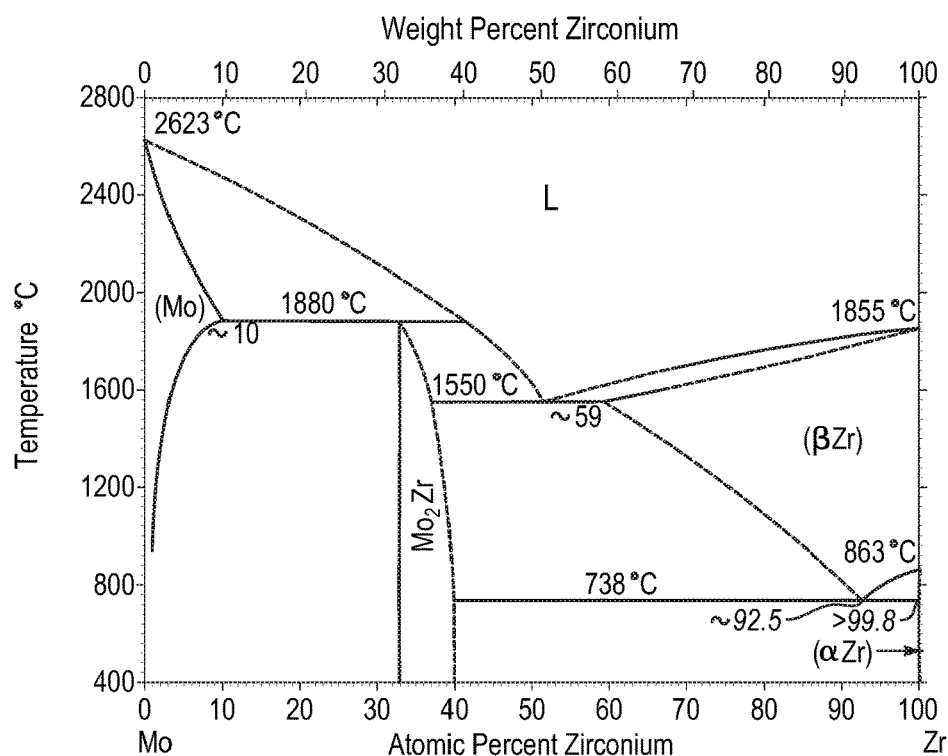
FIGS. 44A and 44B show a phase diagram for molybdenum-zirconium.
Figure 44B:
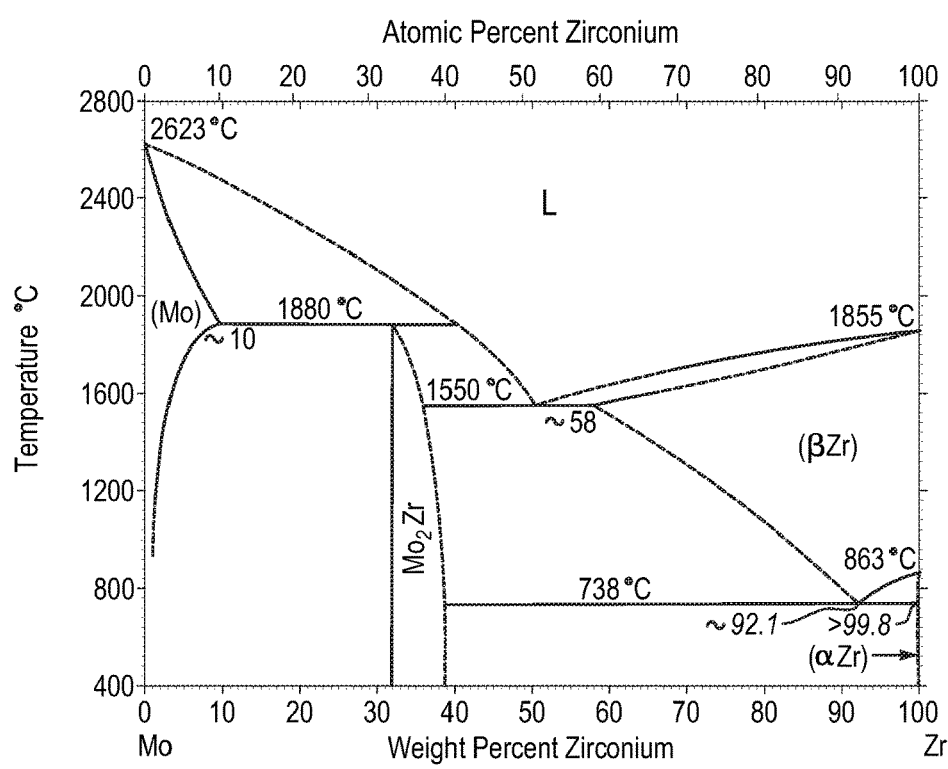

Mo—Zr is a phase diagram with eutectic, peritectic, eutectoid, and allotropic transformation features. A single ordered FCC Mo$_2$Zr phase exists from about 32 to about 39Zr. Up to about 32Zr is a mixture of BCC (Mo) and FCC Mo$_2$Zr phases. Above about 39Zr is a mixture of FCC Mo$_2$Zr and HCP (αZr) phases (FIGS. 44A-44B).

Figure 45A:
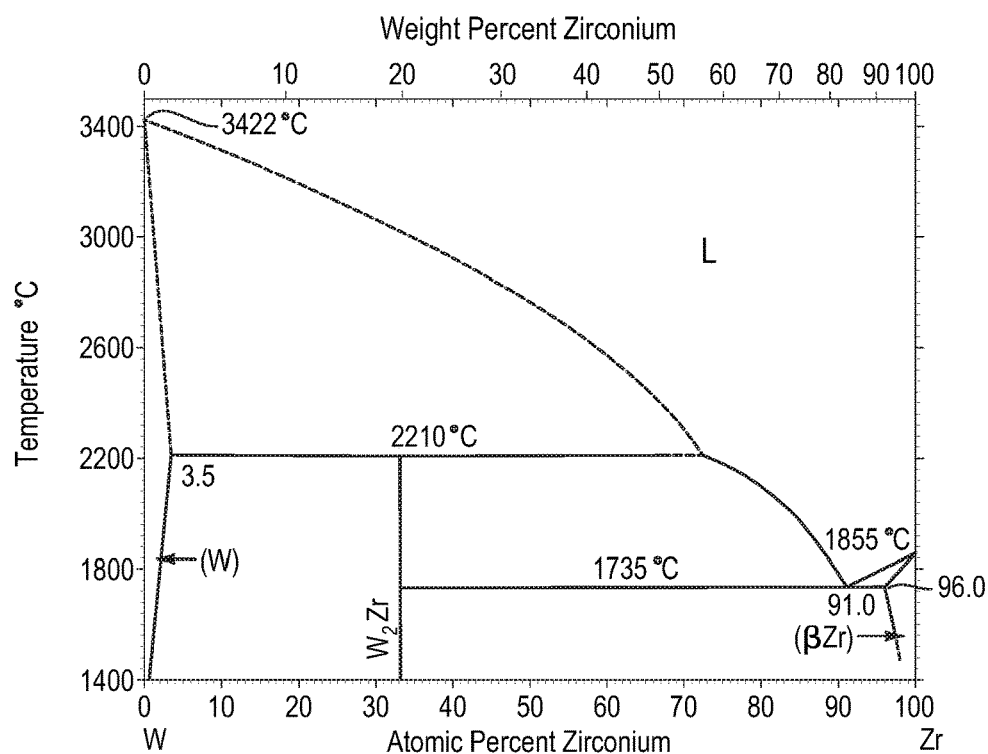
FIGS. 45A and 45B show a phase diagram for tungsten-zirconium.
Figure 45B:
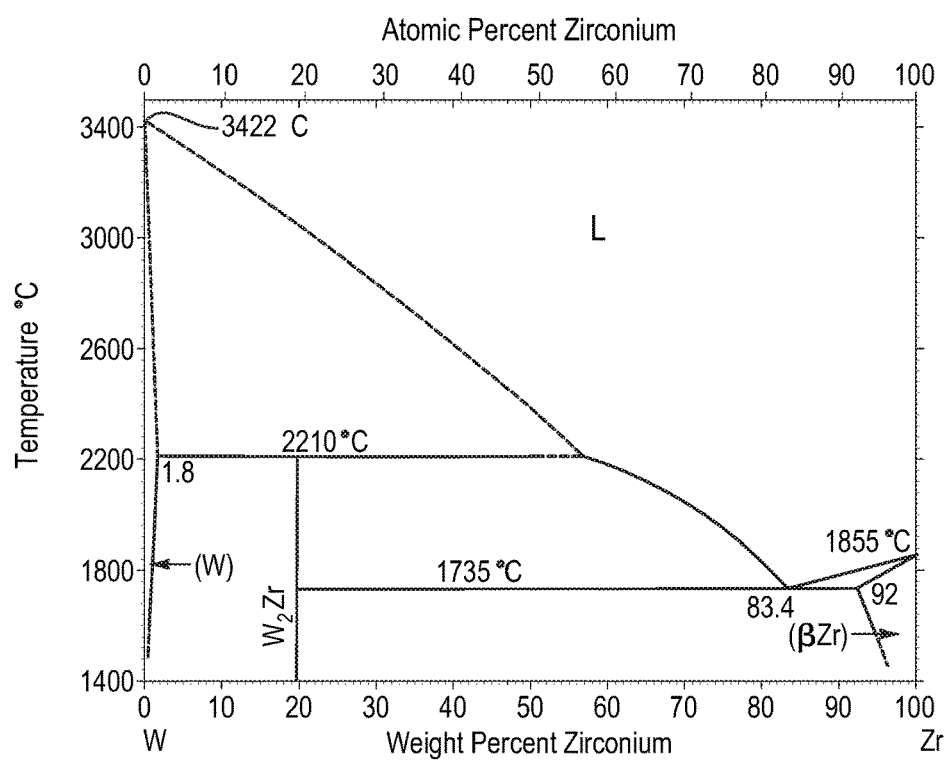

W—Zr is a phase diagram with eutectic features, showing a single ordered FCC W$_2$Zr phase at around 20Zr. Up to about 20Zr is a mixture of BCC (W) and FCC W$_2$Zr phases. Above about 20Zr is a mixture of FCC W$_2$Zr and HCP (αZr) phases (FIGS. 45A-45B).

Figure 46A:
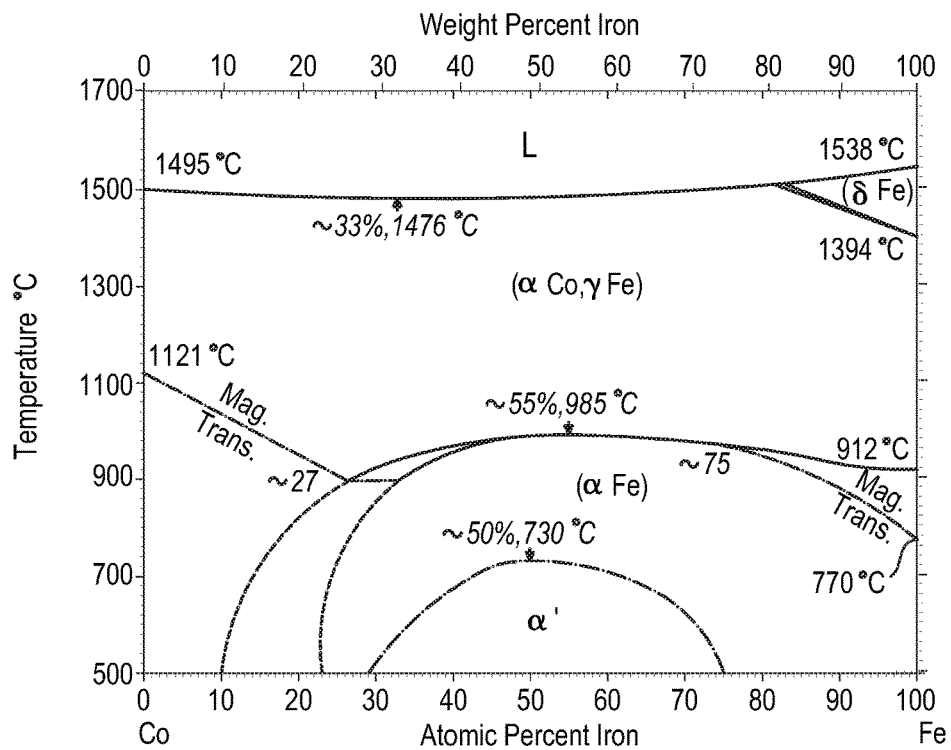
FIGS. 46A and 46B show a phase diagram for cobalt-iron.
Figure 46B:
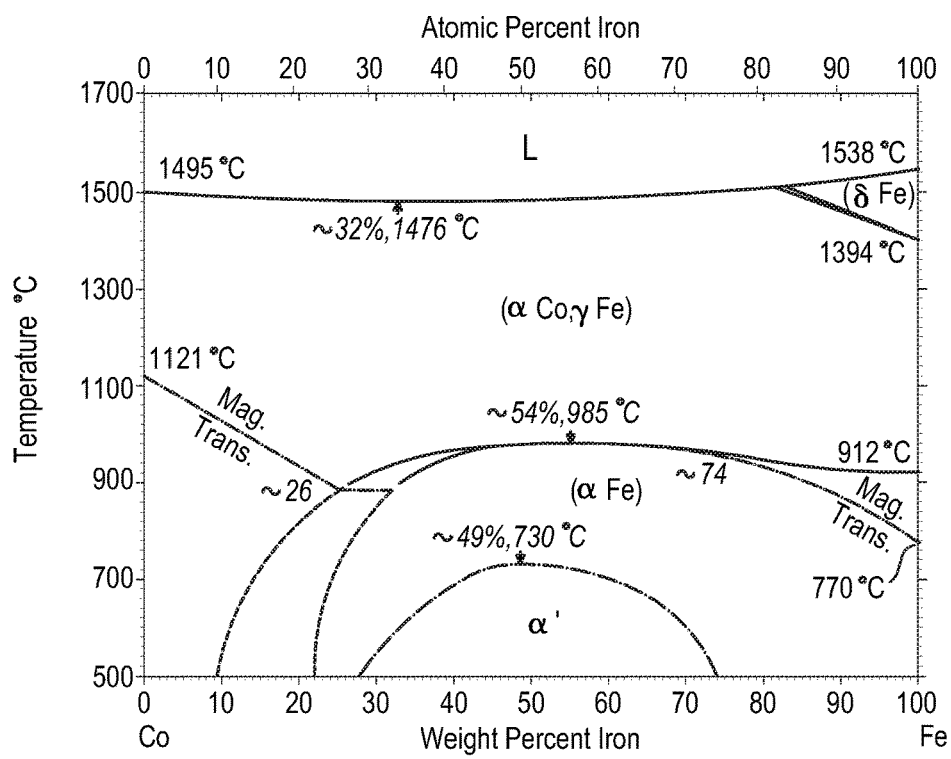

For an alloy containing Co, Cr, Fe and Pd or Pt (e.g., as discussed in more detail in conjunction with Examples 78-89, and particularly Example 85, below), the following may be observed:

Co—Fe is a phase diagram showing a miscibility gap between about 28 and about 74Fe, with a basic cubic structure of the two intermixed Co and Fe phases. Above and below these compositions the structure is a solid solution Co and Fe mixture with a BCC structure (FIGS. 46A-46B).

Figure 47A:
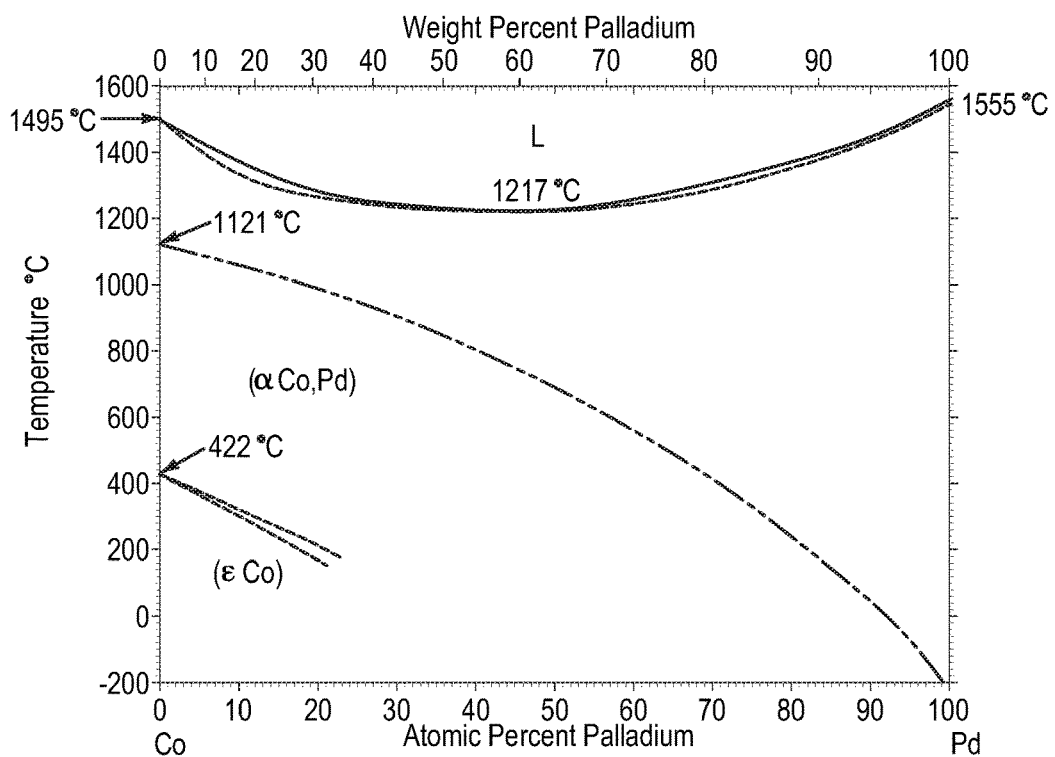
FIGS. 47A and 47B show a phase diagram for cobalt-palladium.
Figure 47B:
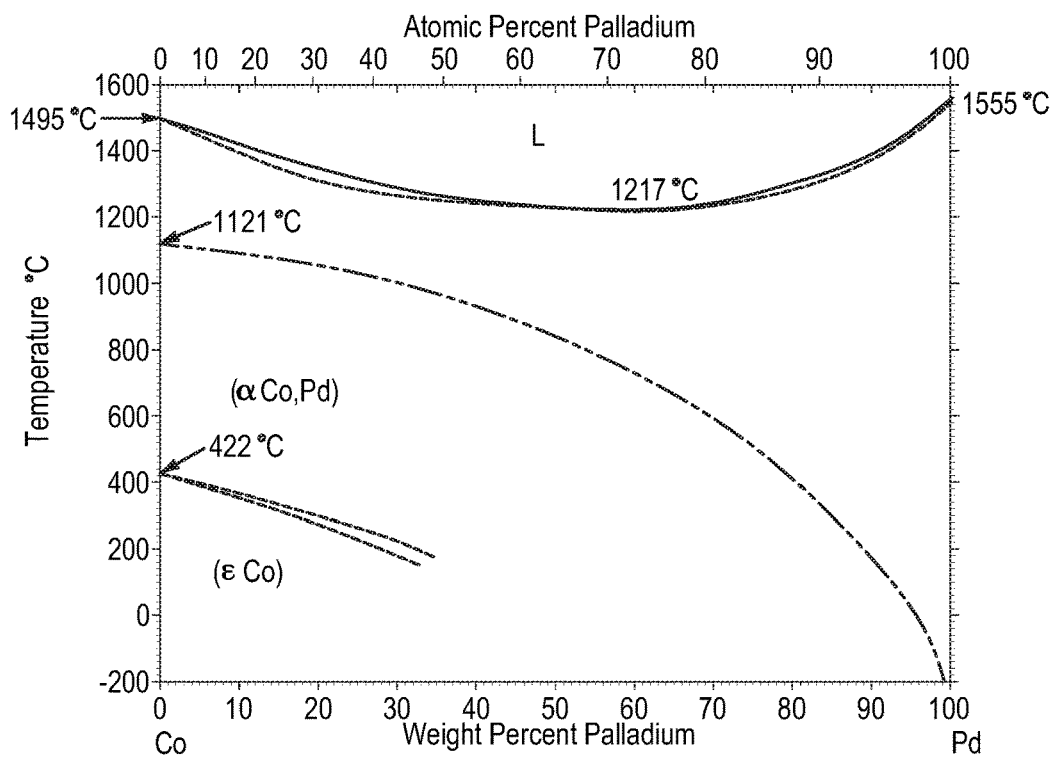

Co—Pd phase diagram shows a continuous solid solution with an HCP (εCo) structure (FIGS. 47A-47B).

Figure 48A:
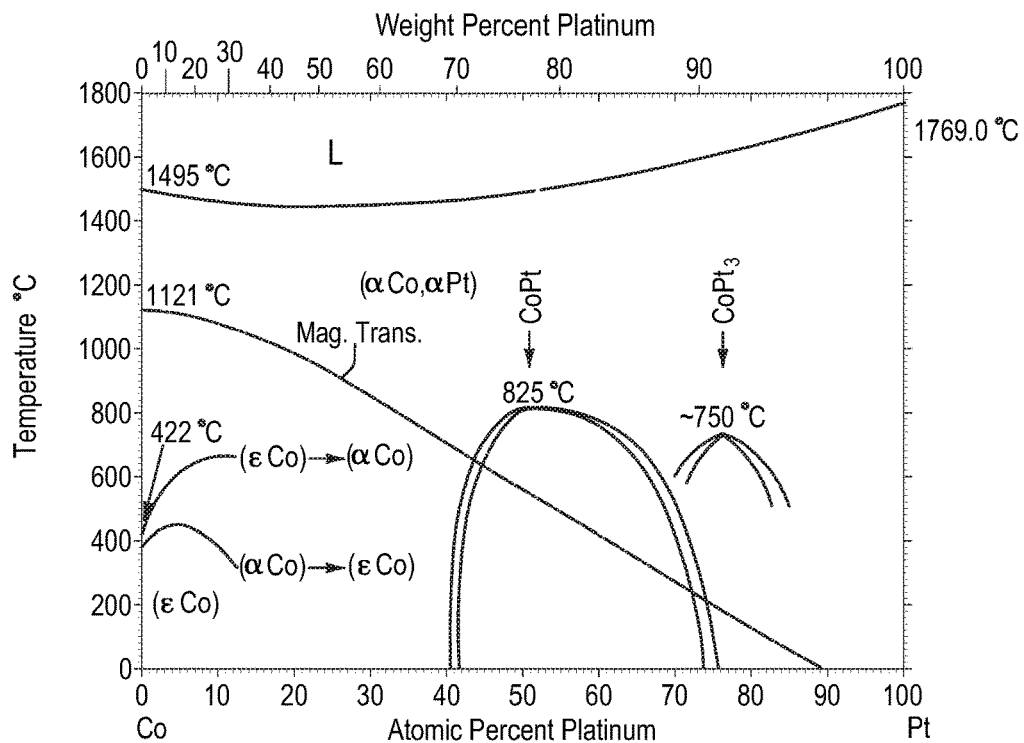
FIGS. 48A and 48B show a phase diagram for cobalt-platinum.
Figure 48B:
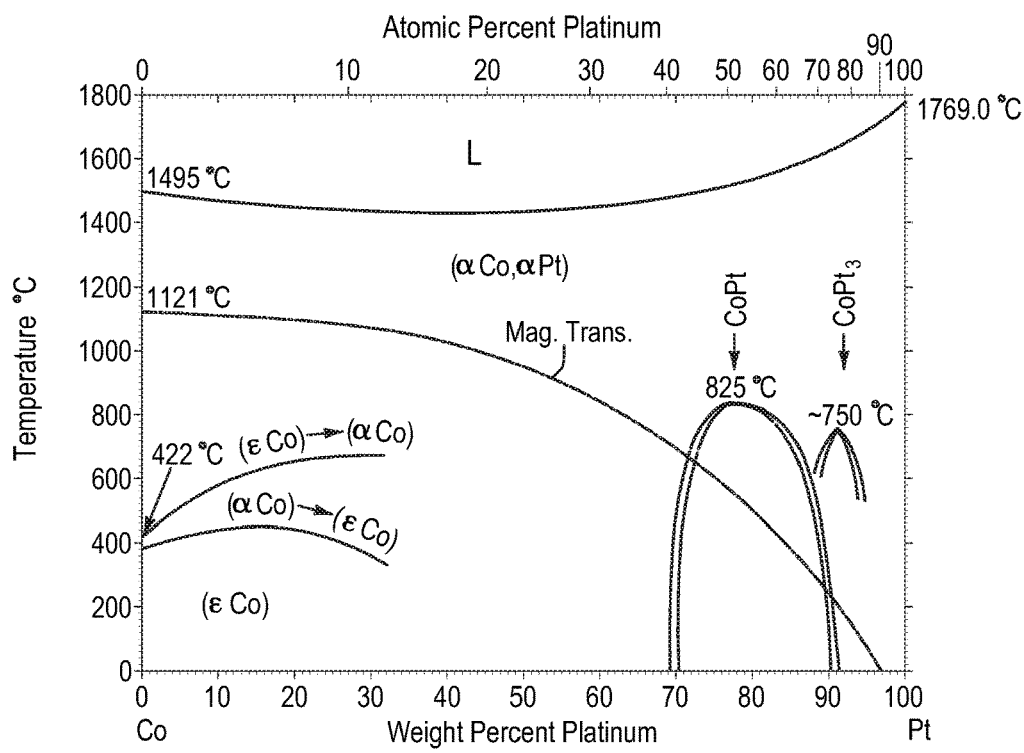

Co—Pt phase diagram shows a solid solution structure with two miscibility gaps and two focal phase formations. Up to about 69Pt the structure is HCP (εCo) and FCC α(Co,Pt). Between about 69 and about 91Pt there is a miscibility gap, with a focal tetragonal CoPt structure at about 76Pt. Above 91Pt there is again FCC α(Co,Pt) (FIGS. 48A-48B).

Figure 49A:
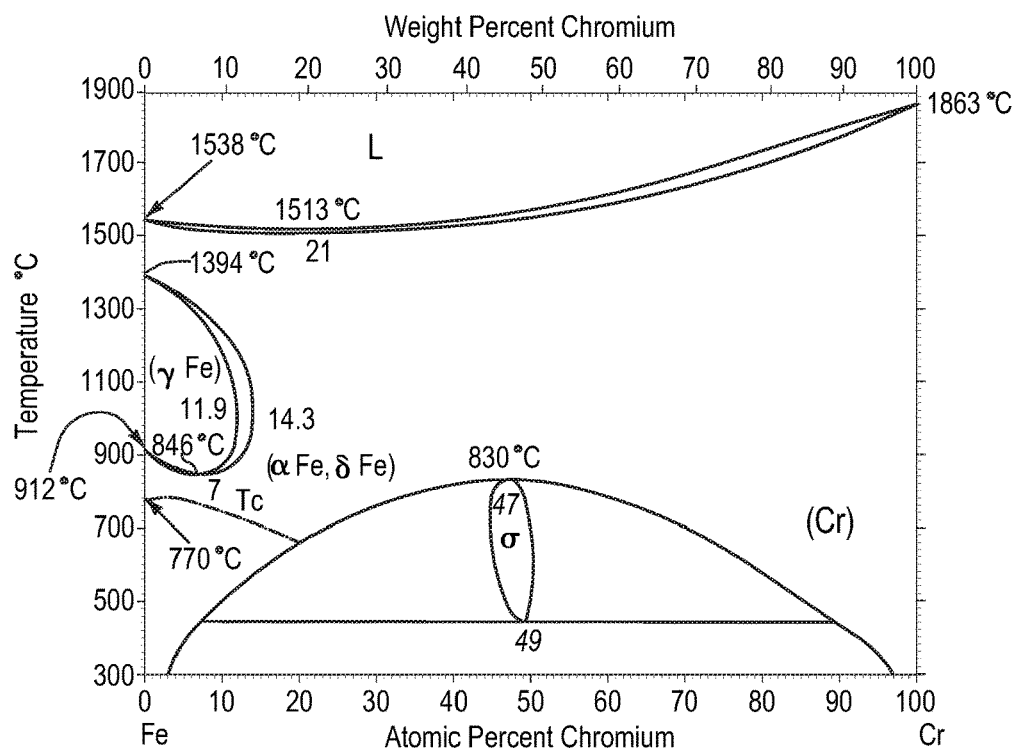
FIGS. 49A and 49B show a phase diagram for chromium-iron.
Figure 49B:
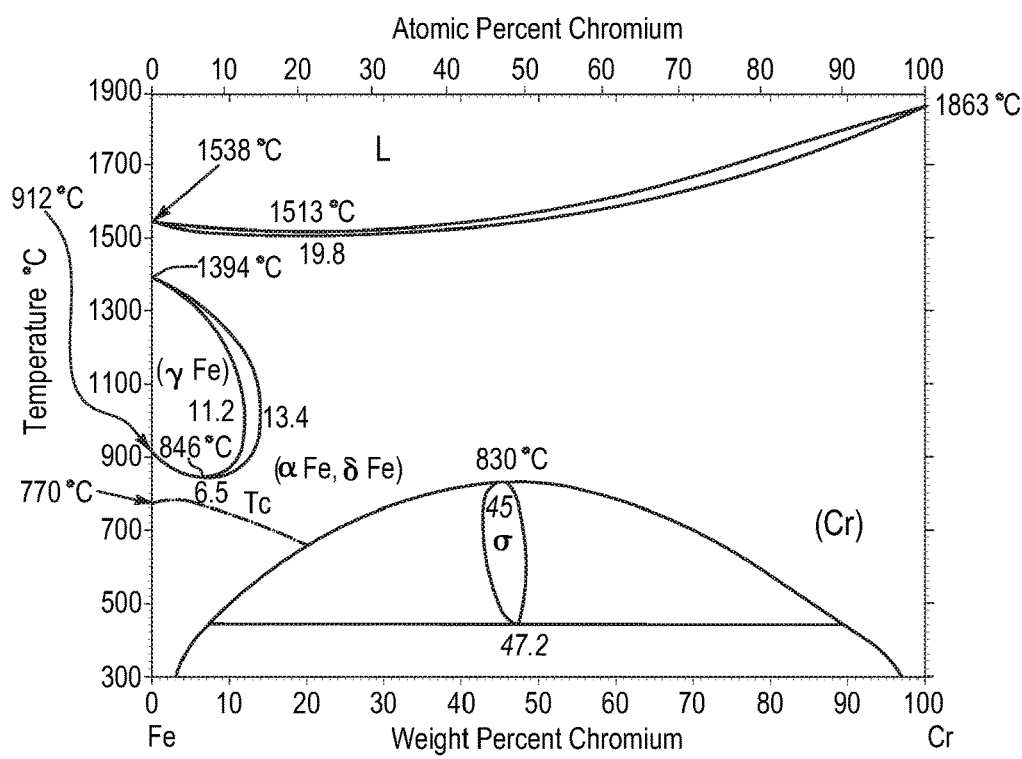

Cr—Fe is a somewhat complex phase diagram with a variety of features. This system displays a BCC eutectic structure between about 3 and about 97Fe. Above 97Fe, the structure is primarily FCC, while below 3Fe the structure is primarily BCC (FIGS. 49A-49B).

Figure 50A:
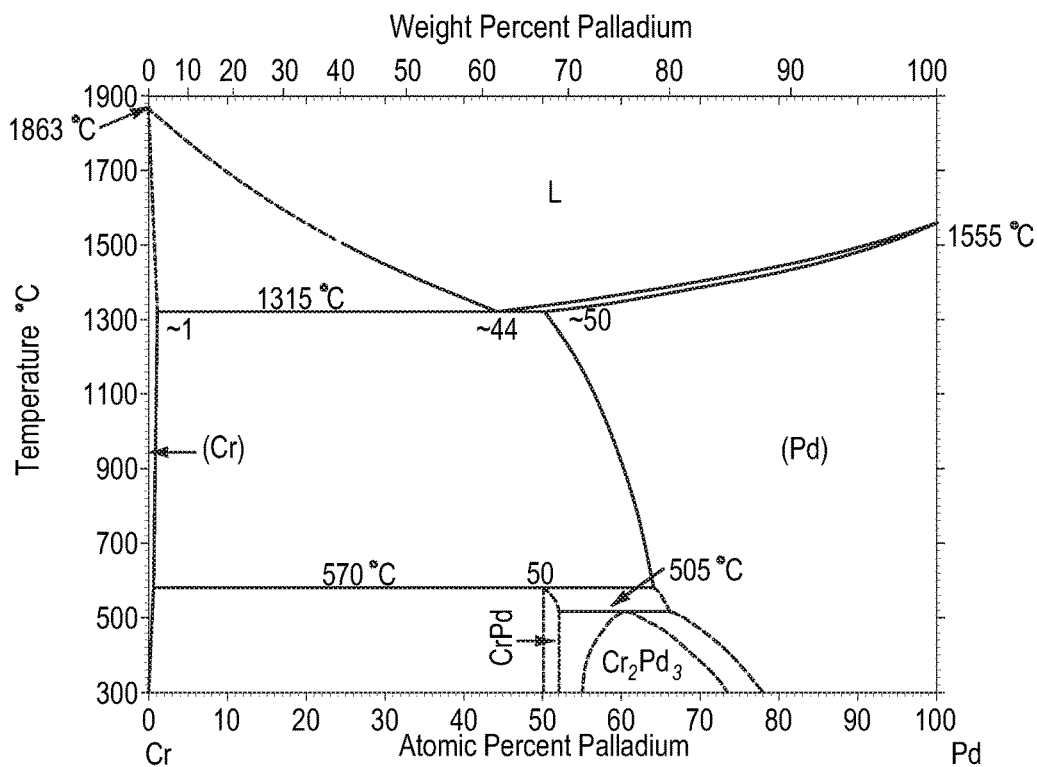
FIGS. 50A and 50B show a phase diagram for chromium-palladium.
Figure 50B:
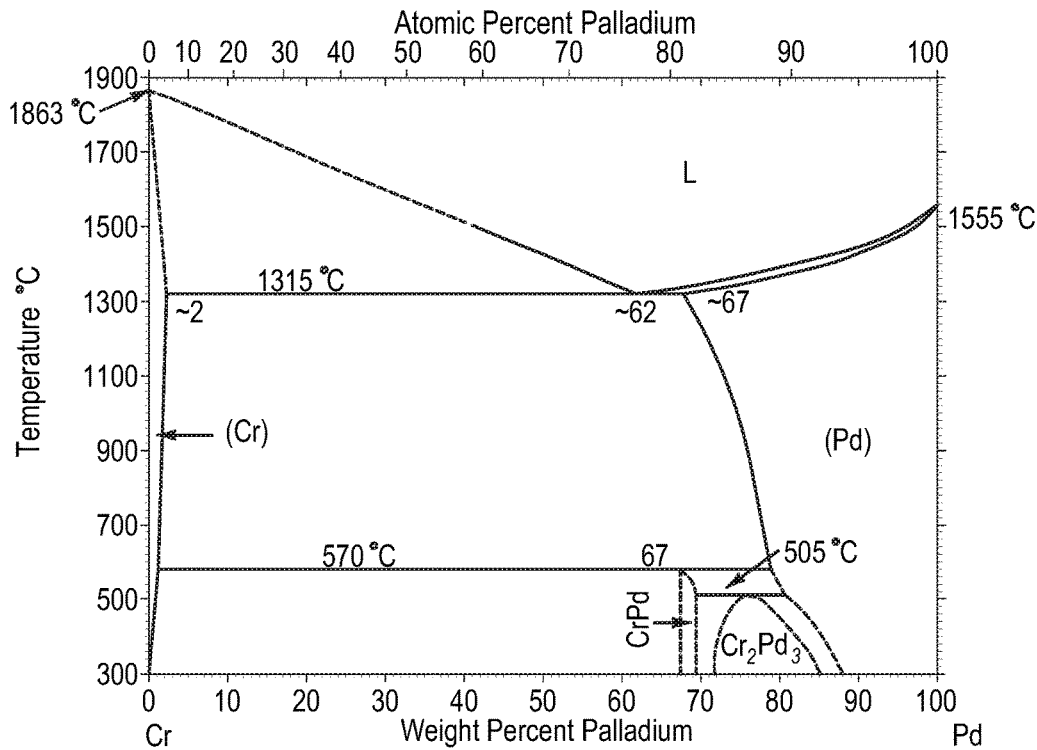

Cr—Pd is a fairly complex phase diagram. Up to about 67Pd, the structure is a mixture of FCC (Cr) and tetragonal CrPd. Between about 67 and about 69Pd the structure is tetragonal CrPd. Between about 69 and about 71Pd, the structure is a mixture of tetragonal CrPd and FCC Cr$_2$Pd$_3$. Between about 71 and about 88Pd the structure is FCC Cr$_2$Pd$_3$. Above about 88Pd, the structure is FCC (Pd) (FIGS. 50A-50B).

Figure 51A:
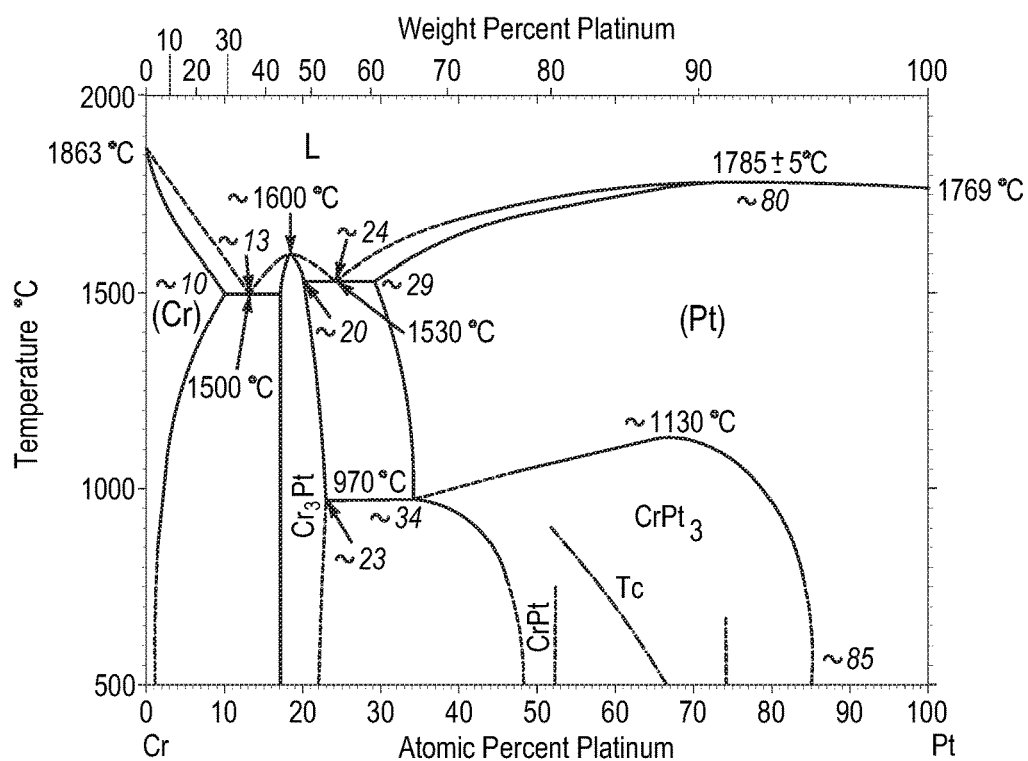
FIGS. 51A and 51B show a phase diagram for chromium-platinum.
Figure 51B:
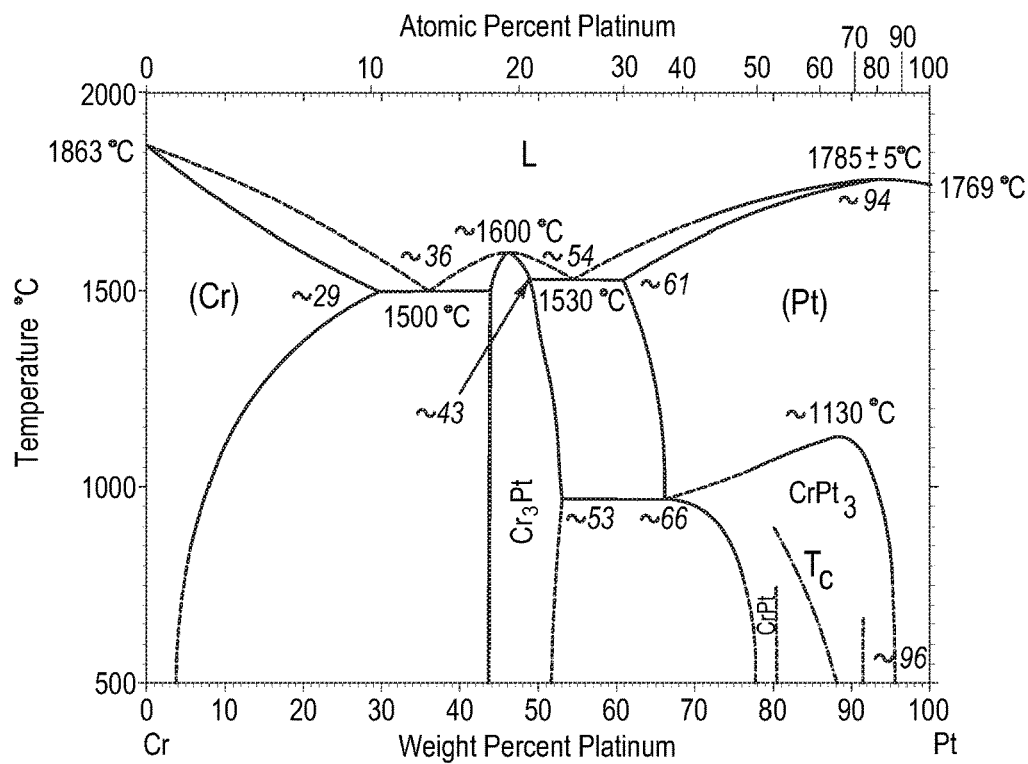

Cr—Pt is a fairly complex phase diagram. Up to about 5Pt, the structure is FCC (Cr). From about 5 to about 43Pt the structure is a mix of FCC (Cr) and cubic Cr$_3$Pt. From about 43 to about 51Pt the structure is cubic Cr$_3$Pt. From about 51 to about 78Pt the structure is a mix of cubic Cr$_3$Pt and tetragonal CrPt. From about 78 to about 80Pt the structure is tetragonal CrPt. From about 80 to about 96Pt the structure is primarily cubic CrPt$_3$. Above about 96Pt the structure is FCC (Pt) (FIGS. 51A-51B).

Figure 52A:
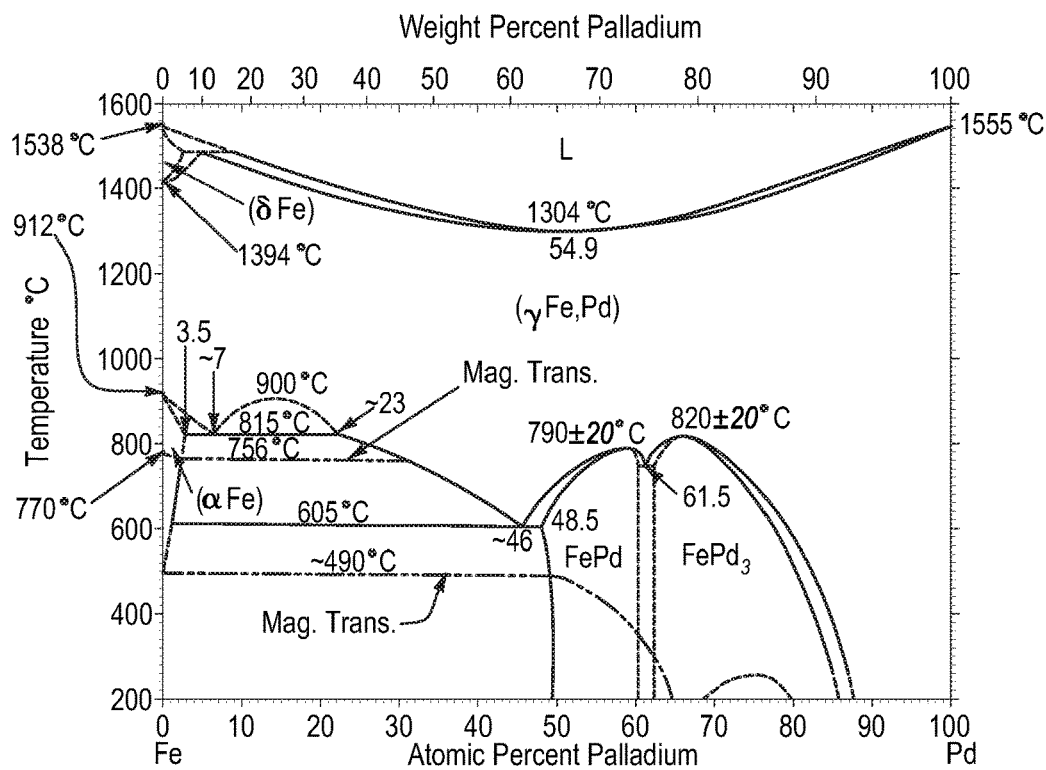
FIGS. 52A and 52B show a phase diagram for iron-palladium.
Figure 52B:
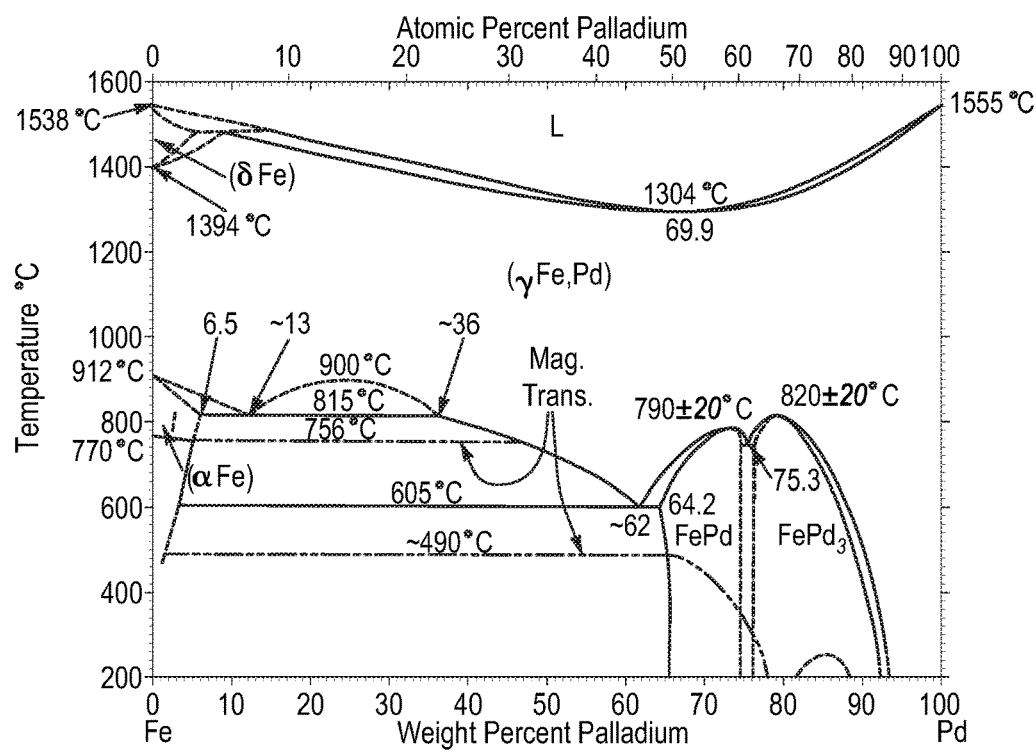

Fe—Pd is a complex phase diagram. Up to about 65Pd is a combination of FCC (γFe,Pd) and tetragonal FePd. From about 65 to about 75Pd is tetragonal FePd. From about 75 to about 93Pd is cubic FePd$_3$. Above around 93Pd is FCC (γFe,Pd) (FIGS. 52A-52B).

Figure 53A:
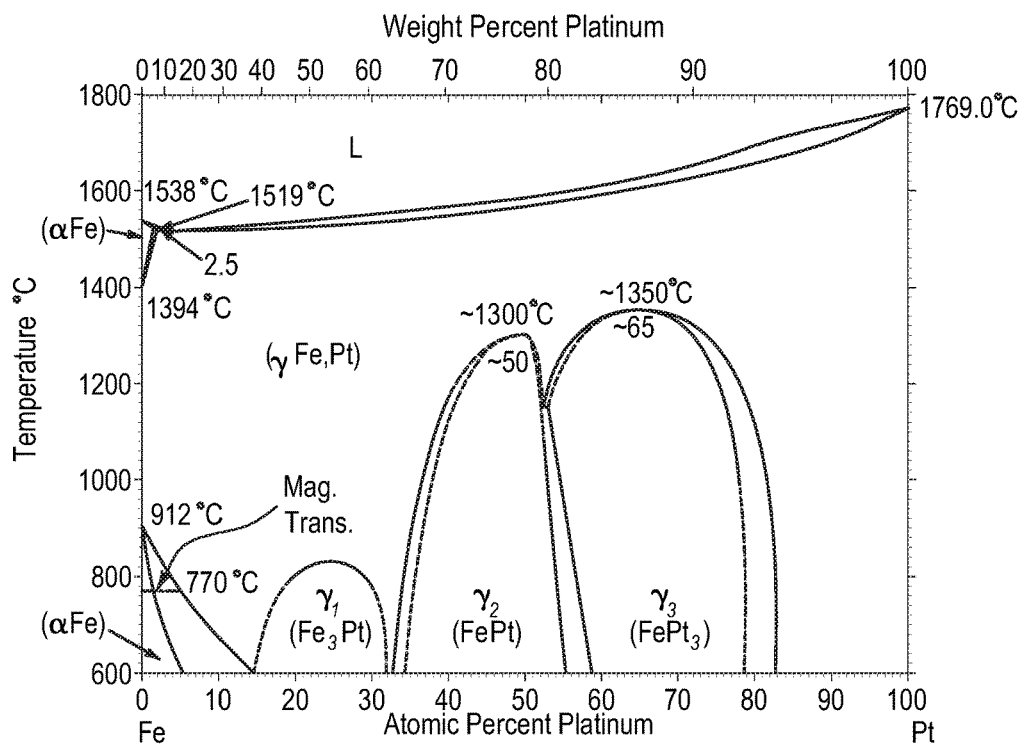
FIGS. 53A and 53B show a phase diagram for iron-platinum.
Figure 53B:
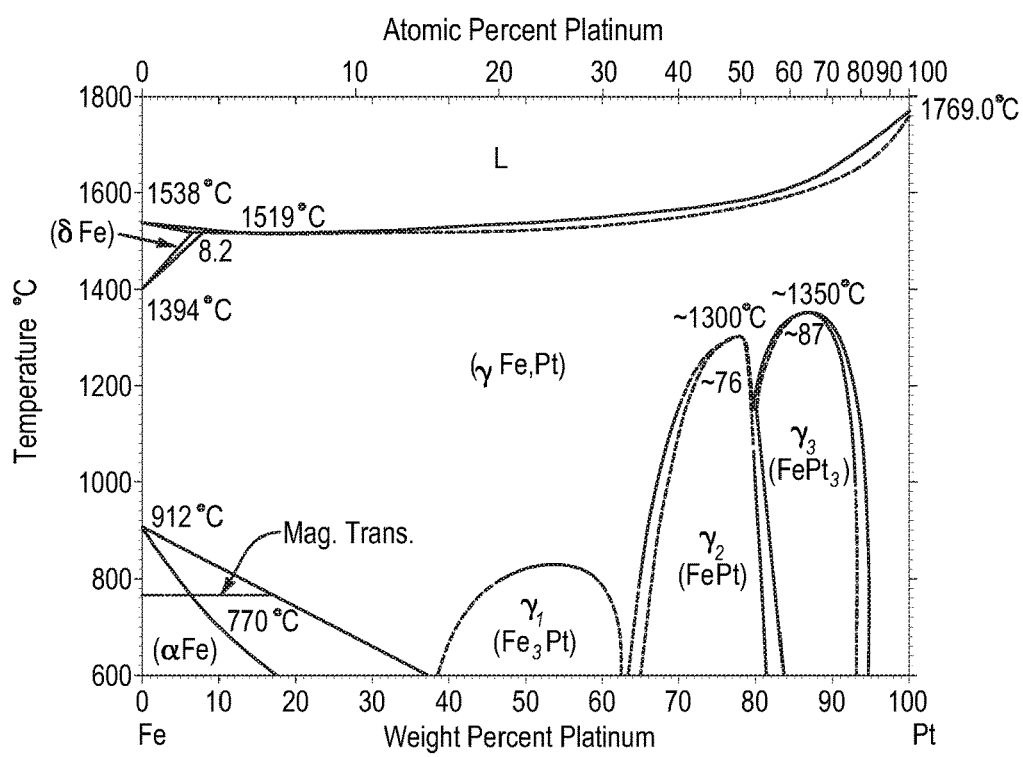

Fe—Pt phase diagram shows a eutectic with multiple intermediate phases. Up to about 18Pt is a BCC solid solution. Between about 18 and about 38Pt is an FCC solid solution. Between about 38 and about 62Pt is cubic $\gamma_1$ (Fe$_3$Pt). Between about 63 and about 82Pt is tetragonal $\gamma_2$ (FePt). Between about 82 and about 94Pt is cubic $\gamma_3$ (FePt$_3$). Above about 94Pt, the structure is a continuous solid solution with a FCC structure (FIGS. 53A-53B).

Figure 54A:
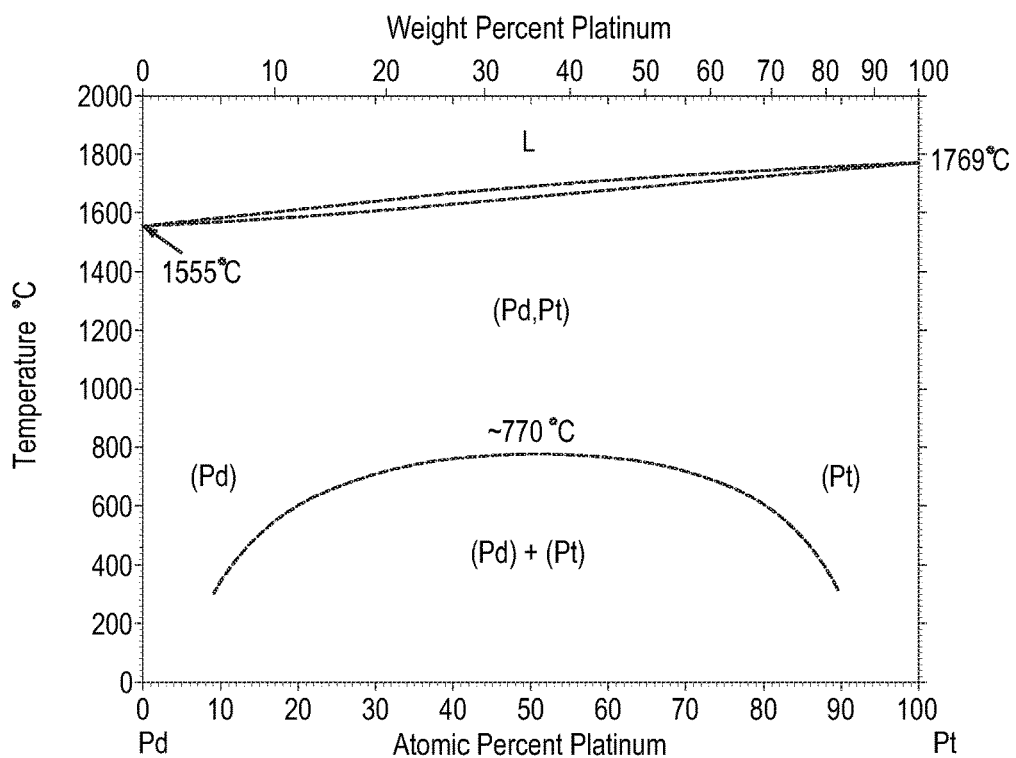
FIGS. 54A and 54B show a phase diagram for palladium-platinum.
Figure 54B:
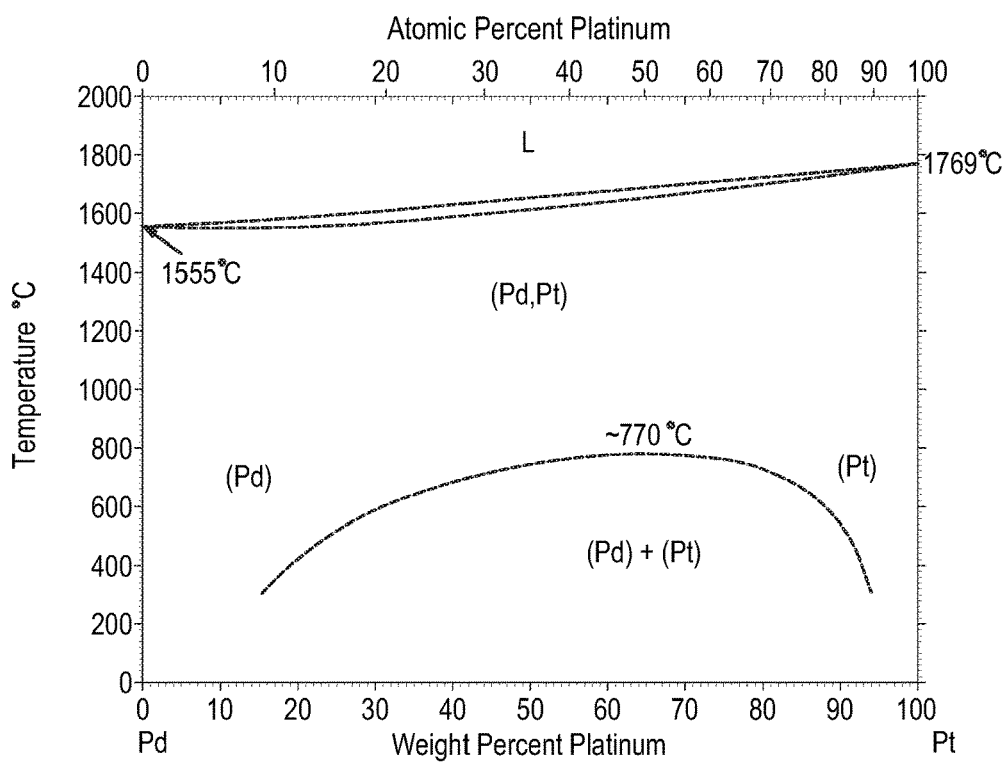

Pd—Pt phase diagram shows a continuous solid solution that is a mixture of FCC (Pd)+(Pt) across the majority of compositions. At some undefined lower and upper compositions the phase is primarily FCC (Pd) or FCC (Pt) (FIGS. 54A-54B).

In considering the possible alloys from both a radiopacity and a compatibility perspective, the following possible compositions come to the forefront. Note that minor and trace elements are not considered in these calculations. It is important to avoid the Co—Cr σ intermetallic phase, because this phase is quite brittle. The examples below will explicitly discuss avoidance of this phase by remaining below the 51-64 weight percent Cr in the Co—Cr regime. It is also envisioned that viable alloy compositions may be provided above this regime (i.e., greater than about 64Cr in the Co—Cr regime) that would provide workable alloys. For example, 10Co and 20Cr would give a relative composition of 33.3Co and 66.7Cr, moving above the σ intermetallic regime.

Examples 25-30 below are based on the nominal compositions of the ASTM F90 L-605 Alloy of Table 1 and the ASTM F562 MP-35N Alloy of Table 3 in which at least the nickel, and in some examples, some of the cobalt has been replaced on an weight substitution basis with a refractory metal, silver. Example 31 further replaces the tungsten of L-605 or the molybdenum of MP-35N with silver so that the alloy is essentially a ternary Co—Cr—Ag alloy. Trace elements such as beryllium, boron, carbon, iron, manganese, phosphorus, silicon, sulfur, and titanium are not listed.

Example 25—ASTM F90 L-605 Alloy with Weight Substitution of Nickel with Silver

| Element | Weight Percent |
| --- | --- |
| Cobalt | 55 |
| Chromium | 20 |
| Tungsten | 15 |
| Silver | 10 |

From a metallurgical perspective, the Co—Cr, Co—W, and Cr—W will fall in the same regions as for L-605. Otherwise the alloy will also include a series of eutectic immiscible phases of FCC Ag, HCP εCo, BCC Cr, and BCC W. This alloy would otherwise behave similarly to L-605, but with increased relatively radiopacity (to about 4.7 barnes/cc).

Example 26—ASTM F90 L-605 Alloy with Weight Substitution of Nickel and a Portion of the Cobalt with Silver

| Element | Weight Percent |
| --- | --- |
| Cobalt | 35 |
| Chromium | 20 |
| Tungsten | 15 |
| Silver | 30 |

In order to increase the radiopacity, the silver may be increased (beyond simply substituting for Ni) to also substitute for a portion of the cobalt. For example, increasing the silver to 30 weight percent would lower cobalt to 35 weight percent, leaving the other elements the same. This results in a calculated radiopacity of 7.0 barnes/cc. Similar to Example 25, the silver would result in a series of immiscible phases with Co, Cr, and W. Co—Cr would shift to be in the same region as MP-35N. Co—W would shift higher but still remain in the same phase region as L-605. Cr—W would remain the same as L-605. This would result in a workable alloy.

Example 27—ASTM F90 L-605 Alloy with Weight Substitution of Nickel and a Portion of the Cobalt with Silver

| Element | Weight Percent |
| --- | --- |
| Cobalt | 25 |
| Chromium | 20 |
| Tungsten | 15 |
| Silver | 40 |

If even higher radiopacity is desired, the silver may be increased to 40 weight percent. This results in a calculated radiopacity of 8.2 barnes/cc. Similar to Example 26, the silver would remain a series of immiscible phases with Co, Cr, and W. Co—Cr would shift to be in the same region as MP-35N, closer to the middle of the phase. Co—W shifts higher but remains in the same phase region as L-605. Cr—W would remain the same as for L-605. This would result in a workable alloy.

Example 28—ASTM F90 L-605 Alloy with Weight Substitution of Nickel and a Portion of the Cobalt with Silver

| Element | Weight Percent |
| --- | --- |
| Cobalt | at least 20 |
| Chromium | 20 |
| Tungsten | 15 |
| Silver | up to 45 |

Assuming that Cr and W are not changed, Ag should remain at or below about 45 weight percent (e.g., 10 to 45 weight percent) in order to avoid the Co—Cr a intermetallic phase. At 45 weight percent Ag, calculated radiopacity would be 8.8 barnes/cc.

Example 29—ASTM F562 MP-35N Alloy with Weight Substitution of Nickel with Silver

| Element | Weight Percent |
| --- | --- |
| Cobalt | 35 |
| Chromium | 20 |
| Molybdenum | 10 |
| Silver | 35 |

Utilizing a straight substitution of silver for nickel on a weight percentage basis results in the calculated radiopacity increasing from 3.4 barnes/cc to 7.0 barnes/cc. From a metallurgical perspective, the alloy includes a series of eutectic immiscible phases of FCC Ag, HCP εCo, BCC Cr, and BCC Mo with Co—Cr, Co—Mo, and Cr—Mo falling in the same regions as MP-35N. This alloy would otherwise behave similarly to MP-35N, but with increased relatively radiopacity (to about 7.0 barnes/cc).

Example 30—ASTM F562 MP-35N Alloy with Weight Substitution of Nickel and a Portion of the Cobalt with Silver

| Element | Weight Percent |
| --- | --- |
| Cobalt | at least 20 |
| Chromium | 20 |
| Molybdenum | 10 |
| Silver | up to 50 |

Assuming that Cr and Mo are not changed, Ag should remain at or below about 50 weight percent (e.g., 35 to 50 weight percent) in order to avoid the Co—Cr σ intermetallic phase. At 50 weight percent Ag, calculated radiopacity would be 8.7 barnes/cc.

Example 31—ASTM F90 L-605 Alloy or ASTM F562 NIP-35N Alloy with Weight Substitution of Nickel and Tungsten or Molybdenum with Silver

| Element | Weight Percent |
| --- | --- |
| Cobalt | at least 20 |
| Chromium | 20 |
| Silver | up to 60 |

When considering the disparity in melting temperature between Ag and Mo and W, the alloy may be considered without either of these elements (the Mo or W), i.e., consisting of Ag—Co—Cr only. In this instance, the Ag may range up to about 60 weight percent to avoid the Co—Cr a intermetallic phase. At 60 weight percent Ag, calculated radiopacity would be 9.0 barnes/cc. Ag—Co and Ag—Cr both fall into the eutectic regimes of these phase diagrams.

Examples 32-35 below are based on the nominal compositions of the ASTM F90 L-605 Alloy of Table 1 and the ASTM F562 MP-35N Alloy of Table 3 in which at least the nickel, and in some examples, some of the cobalt has been replaced on an weight substitution basis with a refractory metal, gold. Example 36 further replaces the tungsten of L-605 or the molybdenum of MP-35N with gold so that the alloy is essentially a ternary Co—Cr—Au alloy. Trace elements such as berylium, boron, carbon, iron, manganese, phosphorus, silicon, sulfur, and titanium are not listed.

Example 32—ASTM F90 L-605 Alloy with Weight Substitution of Nickel with Gold

| Element | Weight Percent |
| --- | --- |
| Cobalt | 55 |
| Chromium | 20 |
| Tungsten | 15 |
| Gold | 10 |

Substituting Au for Ni on a weight percentage basis increases the calculated radiopacity from 3.6 to 4.6 barnes/cc. From a metallurgical perspective, the Co—Cr, Co—W, and Cr—W will fall in the same regions as for L-605. Otherwise the alloy will also include a series of eutectic immiscible phases of FCC Au, BCC α' and HCP εCo, BCC Cr, and BCC W. This alloy would otherwise behave similarly to L-605, but with increased relatively radiopacity (to about 4.6 barnes/cc).

Example 33—ASTM F90 L-605 Alloy with Weight Substitution of Nickel and a Portion of the Cobalt with Gold

| Element | Weight Percent |
| --- | --- |
| Cobalt | at least 20 |
| Chromium | 20 |
| Tungsten | 15 |
| Gold | up to 45 |

As with Ag, assuming that Cr and W are not changed, Au should remain at or below about 45 weight percent (e.g., 10 to 45 weight percent) in order to avoid the Co—Cr a intermetallic phase. At 45 weight percent Au, calculated radiopacity would be 8.9 barnes/cc.

Example 34—ASTM F562 NIP-35N Alloy with Weight Substitution of Nickel with Gold

| Element | Weight Percent |
| --- | --- |
| Cobalt | 35 |
| Chromium | 20 |
| Molybdenum | 10 |
| Gold | 35 |

Utilizing a straight substitution of gold for nickel on a weight percentage basis results in the calculated radiopacity increasing from 3.4 barnes/cc to 6.8 barnes/cc. From a metallurgical perspective, the alloy includes a series of eutectic immiscible phases of FCC Au, BCC α' and HCP εCo, BCC Cr, and BCC Mo with Co—Cr, Co—Mo, and Cr—Mo falling in the same regions as MP-35N. Similar to the MP-35N alloy, this would result in a workable alloy.

Example 35—ASTM F562 MP-35N Alloy with Weight Substitution of Nickel and a Portion of the Cobalt with Gold

| Element | Weight Percent |
| --- | --- |
| Cobalt | at least 20 |
| Chromium | 20 |
| Molybdenum | 10 |
| Gold | up to 50 |

Assuming that Cr and Mo are not changed, Au should remain at or below about 50 weight percent (e.g., 35 to 50 weight percent) in order to avoid the Co—Cr σ intermetallic phase. At 50 weight percent Au, calculated radiopacity would be 8.7 barnes/cc.

Example 36—ASTM F90 L-605 Alloy or ASTM F562 NIP-35N Alloy with Weight Substitution of Nickel and Tungsten or Molybdenum with Gold

| Element | Weight Percent |
| --- | --- |
| Cobalt | at least 20 |
| Chromium | 20 |
| Gold | up to 60 |

When considering the disparity in melting temperature between Au and Mo and W, the alloy may be considered without either of these elements (the Mo or W), i.e., consisting of Au—Co—Cr only. In this instance, the Au may range up to about 60 weight percent to avoid the Co—Cr a intermetallic phase. At 60 weight percent Au, calculated radiopacity would be 9.2 barnes/cc. Au—Co and Au—Cr both fall into the eutectic regimes of these phase diagrams.

Examples 37-40 below are based on the nominal compositions of the ASTM F90 L-605 Alloy of Table 1 and the ASTM F562 MP-35N Alloy of Table 3 in which at least the nickel, and in some examples, some of the cobalt has been replaced on an weight substitution basis with a refractory metal, hafnium. Example 41 further replaces the tungsten of L-605 or the molybdenum of MP-35N with hafnium so that the alloy is essentially a ternary Co—Cr—Hf alloy. Trace elements such as beryllium, boron, carbon, iron, manganese, phosphorus, silicon, sulfur, and titanium are not listed.

When considering such systems, a few items should be taken into account. As Hf falls in the refractory metal category and L-605 and MP-35N Co alloys already include tungsten or Mo, respectively, which also fall into this category, the metallurgical behavior of Hf may be inferred from Co—Mo and Co—W phase diagrams. It is noted that Hf has a large effect on other refractory metals and on Ni and Fe based alloys in small amounts. The grain boundary pinning effect that is experienced in smaller additions will not continue with larger additions. Furthermore, the Co—Hf mixture may be partially paramagnetic as early as around 47 weight percent Hf. As with other alloys, it is likely that this behavior is repressed by the other elements in the alloy, resulting in a workable alloy.

Example 37—ASTM F90 L-605 Alloy with Weight Substitution of Nickel with Hafnium

| Element | Weight Percent |
| --- | --- |
| Cobalt | 55 |
| Chromium | 20 |
| Tungsten | 15 |
| Hafnium | 10 |

Substituting Hf for Ni on a weight percentage basis increases the calculated radiopacity from 3.6 to 4.3 barnes/cc. From a metallurgical perspective, the Co—Cr, Co—W, and Cr—W will fall in the same regions as for L-605. For Hf—Co, the alloy will fall within the mixed HCP εCo and tetragonal $Co_7Hf_2$ regime. For Hf—Cr, the alloy will fall within the FCC $Cr_2Hf$ plus BCC Cr phases. For Hf—Mo the mixture would include BCC W and FCC $HfW_2$. It is expected that this alloy may be stronger than L-605.

Example 38—ASTM F90 L-605 Alloy with Weight Substitution of Nickel and a Portion of the Cobalt with Hafnium

| Element | Weight Percent |
| --- | --- |
| Cobalt | at least 20 |
| Chromium | 20 |
| Tungsten | 15 |
| Hafnium | up to 45 |

As with Ag and Au, here it is assumed that Cr and W are not changed. At around 30 weight percent Hf, radiopacity would be 5.8 barnes/cc. Phases would include a combination of HCP εCo and tetragonal $Co_7Hf_2$, $Cr_2Hf$, HCP αHf, and FCC $HfW_2$. If the suppression of the paramagnetism is successful and strengthening is not too much to allow workability, Hf may be increased up to 45 weight percent. At 45 weight percent Hf, the radiopacity is 7.2 barnes/cc, and metallurgically would result in a mix of FCC $Co_2Hf$ and cubic CoHf, FCC $Cr_2Hf$ and some HCP αHf, and FCC $HfW_2$ and HCP αHf phases.

Example 39—ASTM F562 MP-35N Alloy with Weight Substitution of Nickel with Hafnium

| Element | Weight Percent |
| --- | --- |
| Cobalt | 35 |
| Chromium | 20 |
| Molybdenum | 10 |
| Hafnium | 35 |

Utilizing a straight substitution of hafnium for nickel on a weight percentage basis results in the calculated radiopacity increasing from 3.4 barnes/cc to 5.7 barnes/cc. From a metallurgical perspective, Co—Cr, Co—Mo, and Cr—Mo will fall in the same regions as MP-35N. Co—Hf falls into the possible partially paramagnetic regime with the combination of tetragonal $Co_7Hf_2$ and FCC $Co_2Hf$. Presuming the suppression of the paramagnetism by the presence of the other elements in the alloy, this alloy would also include a combination of FCC $Cr_2Hf$, FCC $αMo_2Hf$ and HCP αHf phases.

Example 40—ASTM F562 NIP-35N Alloy with Weight Substitution of Nickel and a Portion of the Cobalt with Hafnium

| Element | Weight Percent |
| --- | --- |
| Cobalt | at least 20 |
| Chromium | 20 |
| Molybdenum | 10 |
| Hafnium | up to 50 |

If the suppression of the paramagnetism is successful and strengthening is not too much to still allow workability, Hf may be included up to about 50 weight percent. This would result in a radiopacity of 6.9 barnes/cc. Phases in this alloy beyond the MP-35N Co—Cr, Co—Mo and Cr—Mo phase mixtures would include FCC $Co_2Hf$ and cubic CoHf, FCC $Cr_2Hf$ and HCP αHf, and FCC $αMo_2Hf$ and HCP αHf phases.

Example 41—ASTM F90 L-605 Alloy or ASTM F562 MP-35N Alloy with Weight Substitution of Nickel and Tungsten or Molybdenum with Hafnium

| Element | Weight Percent |
| --- | --- |
| Cobalt | at least 20 |
| Chromium | 20 |
| Hafnium | up to 60 |

When considering a simpler mixture, the alloy may be considered without either Mo or W, i.e., consisting of Hf—Co—Cr only. In this instance, the Hf may range up to about 60 weight percent to avoid the Co—Cr σ intermetallic phase. At 60 weight percent Hf, calculated radiopacity would be 6.9 barnes/cc. Co—Hf falls in the cubic CoHf phase and Cr—Hf falls in the FCC Cr$_2$Hf plus HCP αHf regime.

Examples 42-44 below are based on the nominal compositions of the ASTM F90 L-605 Alloy of Table 1 and the ASTM F562 MP-35N Alloy of Table 3 in which at least the nickel, and in some examples, some of the cobalt has been replaced on an weight substitution basis with a refractory metal, molybdenum. Example 45 further replaces the tungsten of L-605 (or is relative to MP-35N, which already includes some molybdenum) with molybdenum so that the alloy is essentially a ternary Co—Cr—Mo alloy. Trace elements such as beryllium, boron, carbon, iron, manganese, phosphorus, silicon, sulfur, and titanium are not listed.

Example 42—ASTM F90 L-605 Alloy with Weight Substitution of Nickel with Molybdenum

| Element | Weight Percent |
| --- | --- |
| Cobalt | 55 |
| Chromium | 20 |
| Tungsten | 15 |
| Molybdenum | 10 |

Substituting Mo for Ni on a weight percentage basis increases the calculated radiopacity from 3.6 to 4.4 barnes/cc. From a metallurgical perspective, the Co—Cr, Co—W, and Cr—W will fall in the same regions as for L-605. Otherwise the alloy will contain a mixture of HCP εCo and HCP κ phases, BCC Cr and BCC Mo phases, and solid solution Mo and W phases.

Example 43—ASTM F90 L-605 Alloy with Weight Substitution of Nickel and a Portion of the Cobalt with Molybdenum

| Element | Weight Percent |
| --- | --- |
| Cobalt | at least 20 |
| Chromium | 20 |
| Tungsten | 15 |
| Molybdenum | up to 45 |

As with the above alloys of Ag, Au, and Hf, here it is assumed that Cr and W are not changed, thus Co—Cr, Co—W, and Cr—W are the same as for L-605. From a metallurgical phase diagram perspective, Mo may be included up to about 45 weight percent. At 45 weight percent Mo, this gives a radiopacity of 7.2 barnes/cc and metallurgically would result in a mix of rhombohedral ε and BCC Mo, BCC Cr and BCC Mo, and BCC Mo and BCC W phases.

Example 44—ASTM F562 MP-35N Alloy with Weight Substitution of Nickel with Molybdenum

| Element | Weight Percent |
| --- | --- |
| Cobalt | 35 |
| Chromium | 20 |
| Molybdenum | 45 |

Utilizing a straight substitution of molybdenum for nickel on a weight percentage basis increases the radiopacity from 3.4 barnes/cc to 5.8 barnes/cc. From a metallurgical perspective, Co—Cr falls in the same region as MP-35N. Co—Mo and Cr—Mo shift, as the Mo has increased by 35 weight percentage points. Co—Mo shifts into the rhombohedral E phase region, and Cr—Mo stays in the BCC Cr and BCC Mo regime, shifting closer to the Mo side of the phase diagram.

Example 45—ASTM F90 L-605 Alloy or ASTM F562 MP-35N Alloy with Weight Substitution of Nickel and Tungsten or a Portion of the Cobalt with Molybdenum

| Element | Weight Percent |
| --- | --- |
| Cobalt | at least 20 |
| Chromium | 20 |
| Molybdenum | up to 60 |

When considering a simpler mixture, the alloy may be considered with even more Mo, without W (in the case of L-605), i.e., consisting of Mo—Co—Cr only. In the case of a modified MP-35N alloy, some of the cobalt may be replaced to further increase Mo content. Avoiding the Co—Cr a intermetallic phase, Mo may be used up to 60 weight percent. This increases the radiopacity to 7.0 barnes/cc. This would shift the Co—Mo interaction into the rhombohedral E and BCC Mo phase regime. The Cr—Co would remain in the BCC Cr and BCC Mo regime, shifting further toward the Mo side of the phase diagram.

Examples 46-49 below are based on the nominal compositions of the ASTM F90 L-605 Alloy of Table 1 and the ASTM F562 MP-35N Alloy of Table 3 in which at least the nickel, and in some examples, some of the cobalt has been replaced on an weight substitution basis with a refractory metal, niobium. Example 50 further replaces the tungsten of L-605 or the molybdenum of MP-35N with niobium so that the alloy is essentially a ternary Co—Cr—Nb alloy. Trace elements such as beryllium, boron, carbon, iron, manganese, phosphorus, silicon, sulfur, and titanium are not listed.

Example 46—ASTM F90 L-605 Alloy with Weight Substitution of Nickel with Niobium

| Element | Weight Percent |
| --- | --- |
| Cobalt | 55 |
| Chromium | 20 |
| Tungsten | 15 |
| Niobium | 10 |

Substituting Nb for Ni on a weight percentage basis increases the calculated radiopacity from 3.6 to 4.2 barnes/cc. From a metallurgical perspective, the Co—Cr, Co—W, and Cr—W will fall in the same regions as for L-605. Otherwise the alloy will contain a mixture of HCP εCo and HCP NbCo$_3$ phases, BCC Cr and BCC Cr$_2$Nb phases, and solid solution Nb and W phases.

Example 47—ASTM F90 L-605 Alloy with Weight Substitution of Nickel and a Portion of the Cobalt with Niobium

| Element | Weight Percent |
| --- | --- |
| Cobalt | at least 20 |
| Chromium | 20 |
| Tungsten | 15 |
| Niobium | up to 45 |

As with the above alloys of Ag, Au, Hf, and Mo, here it is assumed that Cr and W are not changed, thus Co—Cr, Co—W, and Cr—W are the same as for L-605. From a metallurgical phase diagram perspective, Nb may be included up to about 45 weight percent. At 45 weight percent Nb, this gives a radiopacity of 6.3 barnes/cc and metallurgically would result in a mix of rhombohedral Nb$_6$Co$_7$ and BCC Nb, FCC Cr$_2$Nb and BCC Nb, and BCC Nb and BCC W phases.

Example 48—ASTM F562 MP-35N Alloy with Weight Substitution of Nickel with Niobium

| Element | Weight Percent |
| --- | --- |
| Cobalt | 35 |
| Chromium | 20 |
| Molybdenum | 10 |
| Niobium | 35 |

Utilizing a straight substitution of niobium for nickel on a weight percentage basis increases the radiopacity from 3.4 barnes/cc to 5.3 barnes/cc. From a metallurgical perspective, Co—Cr, Co—Mo, and Cr—Mo fall in the same regions as MP-35N. Other phases will include rhombohedral Nb$_6$Co$_7$ and BCC Nb phases, FCC Cr$_2$Nb and BCC Nb phases, and BCC Nb and BCC Mo phases.

Example 49—ASTM F562 NIP-35N Alloy with Weight Substitution of Nickel and a Portion of the Cobalt with Niobium

| Element | Weight Percent |
| --- | --- |
| Cobalt | at least 20 |
| Chromium | 20 |
| Molybdenum | 10 |
| Niobium | up to 50 |

While avoiding the Co—Cr a intermetallic phase Nb may be included up to 50 weight percent. This increases radiopacity to 6.1 barnes/cc. Metallurgically, this results in the presence of rhombohedral Nb$_6$Co$_7$ and BCC Nb phases, FCC Cr$_2$Nb and BCC Nb phases, and BCC Nb and BCC Mo phases.

Example 50—ASTM F90 L-605 Alloy or ASTM F562 MP-35N Alloy with Weight Substitution of Nickel and Tungsten or Molybdenum with Niobium

| Element | Weight Percent |
| --- | --- |
| Cobalt | at least 20 |
| Chromium | 20 |
| Niobium | up to 60 |

When considering a simpler mixture, the alloy may be considered without either Mo or W, i.e., consisting of Nb—Co—Cr only. In this instance, the Nb may range up to about 60 weight percent to avoid the Co—Cr σ intermetallic phase. At 60 weight percent Nb, calculated radiopacity would be 5.9 barnes/cc. Co—Nb falls in the rhombohedral Nb$_6$Co$_7$ and BCC Nb regime, while the Cr—Nb falls in the FCC Cr$_2$Nb and BCC Nb regime.

Examples 51-54 below are based on the nominal compositions of the ASTM F90 L-605 Alloy of Table 1 and the ASTM F562 MP-35N Alloy of Table 3 in which at least the nickel, and in some examples, some of the cobalt has been replaced on an weight substitution basis with a refractory metal, rhenium. Example 55 further replaces the tungsten of L-605 or the molybdenum of MP-35N with rhenium so that the alloy is essentially a ternary Co—Cr—Re alloy. Trace elements such as beryllium, boron, carbon, iron, manganese, phosphorus, silicon, sulfur, and titanium are not listed.

Example 51—ASTM F90 L-605 Alloy with Weight Substitution of Nickel with Rhenium

| Element | Weight Percent |
| --- | --- |
| Cobalt | 55 |
| Chromium | 20 |
| Tungsten | 15 |
| Rhenium | 10 |

Substituting Re for Ni on a weight percentage basis increases the calculated radiopacity from 3.6 to 4.4 barnes/cc. From a metallurgical perspective, the Co—Cr, Co—W, and Cr—W will fall in the same regions as for L-605. Otherwise the alloy will contain a mixture of HCP εCo and HCP Re phases, BCC Cr and BCC Re phases, and the Re—W will contain tetragonal σ phase and BCC W phase.

Example 52—ASTM F90 L-605 Alloy with Weight Substitution of Nickel and a Portion of the Cobalt with Rhenium

| Element | Weight Percent |
|---|---|
| Cobalt | at least 20 |
| Chromium | 20 |
| Tungsten | 15 |
| Rhenium | up to 45 |

As with the above alloys of Ag, Au, Hf, Mo, and Nb, here it is assumed that Cr and W are not changed, thus Co—Cr, Co—W, and Cr—W are the same as for L-605. From a metallurgical phase diagram perspective, Re may be included up to about 45 weight percent. At 45 weight percent Re, this gives a radiopacity of 8.0 barnes/cc and metallurgically would result in a mix of HCP (εCo,Re), BCC Cr and tetragonal σ($Cr_2Re_3$), and BCC χ and HCP Re phases.

Example 53—ASTM F562 MP-35N Alloy with Weight Substitution of Nickel with Rhenium

| Element | Weight Percent |
|---|---|
| Cobalt | 35 |
| Chromium | 20 |
| Molybdenum | 10 |
| Rhenium | 35 |

Utilizing a straight substitution of rhenium for nickel on a weight percentage basis increases the radiopacity from 3.4 barnes/cc to 6.1 barnes/cc. From a metallurgical perspective, Co—Cr, Co—Mo, and Cr—Mo fall in the same regions as MP-35N. Other phases will include HCP (εCo,Re), BCC Cr and BCC Re phases, and BCC Mo and BCC χ phases.

Example 54—ASTM F562 MP-35N Alloy with Weight Substitution of Nickel and a Portion of the Cobalt with Rhenium

| Element | Weight Percent |
|---|---|
| Cobalt | at least 20 |
| Chromium | 20 |
| Molybdenum | 10 |
| Rhenium | up to 50 |

While avoiding the Co—Cr σ intermetallic phase Re may be included up to 50 weight percent. This increases radiopacity to 7.8 barnes/cc. Metallurgically, this results in the presence of HCP (εCo,Re), BCC Cr and tetragonal σ($Cr_2Re_3$), and BCC Mo and BCC χ phases.

Example 55—ASTM F90 L-605 Alloy or ASTM F562 NIP-35N Alloy with Weight Substitution of Nickel and Tungsten or Molybdenum with Rhenium

| Element | Weight Percent |
|---|---|
| Cobalt | at least 20 |
| Chromium | 20 |
| Rhenium | up to 60 |

When considering a simpler mixture, the alloy may be considered without either Mo or W, i.e., consisting of Re—Co—Cr only. In this instance, the Re may range up to about 60 weight percent to avoid the Co—Cr σ intermetallic phase. At 60 weight percent Re, calculated radiopacity would be 8.1 barnes/cc. Co—Re falls in the HCP (εCo,Re) regime while Cr—Re falls into the BCC Cr and tetragonal σ($Cr_2Re_3$) regime.

Examples 56-59 below are based on the nominal compositions of the ASTM F90 L-605 Alloy of Table 1 and the ASTM F562 MP-35N Alloy of Table 3 in which at least the nickel, and in some examples, some of the cobalt has been replaced on an weight substitution basis with a refractory metal, tantalum. Example 60 further replaces the tungsten of L-605 or the molybdenum of MP-35N with tantalum so that the alloy is essentially a ternary Co—Cr—Ta alloy. Trace elements such as beryllium, boron, carbon, iron, manganese, phosphorus, silicon, sulfur, and titanium are not listed.

Example 56—ASTM F90 L-605 Alloy with Weight Substitution of Nickel with Tantalum

| Element | Weight Percent |
|---|---|
| Cobalt | 55 |
| Chromium | 20 |
| Tungsten | 15 |
| Tantalum | 10 |

Substituting Ta for Ni on a weight percentage basis increases the calculated radiopacity from 3.6 to 4.4 barnes/cc. From a metallurgical perspective, the Co—Cr, Co—W, and Cr—W will fall in the same regions as for L-605. Otherwise the alloy will contain a mixture of HCP εCo and $Co_7Ta_2$, BCC Cr and FCC $Cr_2Ta$, and BCC (Ta,W) phases.

Example 57—ASTM F90 L-605 Alloy with Weight Substitution of Nickel and a Portion of the Cobalt with Tantalum

| Element | Weight Percent |
|---|---|
| Cobalt | at least 20 |
| Chromium | 20 |
| Tungsten | 15 |
| Tantalum | up to 45 |

As with the above alloys of Ag, Au, Hf, Mo, Nb and Re, here it is assumed that Cr and W are not changed, thus Co—Cr, Co—W, and Cr—W are the same as for L-605. From a metallurgical phase diagram perspective, Ta may be included up to about 45 weight percent. At 45 weight percent Ta, this gives a radiopacity of 7.9 barnes/cc and metallurgically would result in a mix of FCC $\lambda_2$ (Co$_2$Ta) and rhombohedral Co$_6$Ta$_7$, FCC Cr$_2$Ta and BCC Ta, and BCC (Ta,W) phases.

Example 58—ASTM F562 MP-35N Alloy with Weight Substitution of Nickel with Tantalum

| Element | Weight Percent |
| --- | --- |
| Cobalt | 35 |
| Chromium | 20 |
| Molybdenum | 10 |
| Tantalum | 35 |

Utilizing a straight substitution of tantalum for nickel on a weight percentage basis increases the radiopacity from 3.4 barnes/cc to 6.1 barnes/cc. From a metallurgical perspective, Co—Cr, Co—Mo, and Cr—Mo fall in the same regions as MP-35N. Other phases will include Co$_7$Ta$_2$ and HCP $\lambda_3$, FCC Cr$_2$Ta, and BCC Mo and BCC Ta phases.

Example 59—ASTM F562 MP-35N Alloy with Weight Substitution of Nickel and a Portion of the Cobalt with Tantalum

| Element | Weight Percent |
| --- | --- |
| Cobalt | at least 20 |
| Chromium | 20 |
| Molybdenum | 10 |
| Tantalum | up to 50 |

While avoiding the Co—Cr a intermetallic phase Ta may be included up to 50 weight percent. This increases radiopacity to 7.7 barnes/cc. Metallurgically, this results in the presence of Co$_6$Ta$_7$, FCC Cr$_2$Ta and BCC Ta, and BCC Mo and BCC Ta phases.

Example 60—ASTM F90 L-605 Alloy or ASTM F562 NIP-35N Alloy with Weight Substitution of Nickel and Tungsten or Molybdenum with Tantalum

| Element | Weight Percent |
| --- | --- |
| Cobalt | at least 20 |
| Chromium | 20 |
| Tantalum | up to 60 |

When considering a simpler mixture, the alloy may be considered without either Mo or W, i.e., consisting of Ta—Co—Cr only. In this instance, the Ta may range up to about 60 weight percent to avoid the Co—Cr a intermetallic phase. At 60 weight percent Ta, calculated radiopacity would be 7.9 barnes/cc. Co—Ta falls in the rhombohedral Co$_6$Ta$_7$ regime and Cr—Ta falls in the FCC Cr$_2$Ta and BCC Ta regime.

Examples 61-64 below are based on the nominal compositions of the ASTM F90 L-605 Alloy of Table 1 and the ASTM F562 MP-35N Alloy of Table 3 in which at least the nickel, and in some examples, some of the cobalt has been replaced on an weight substitution basis with a refractory metal, tungsten. The modified L-605 alloys are essentially ternary Co—Cr—W alloys. Trace elements such as beryllium, boron, carbon, iron, manganese, phosphorus, silicon, sulfur, and titanium are not listed.

Example 61—ASTM F90 L-605 Alloy with Weight Substitution of Nickel with Tungsten

| Element | Weight Percent |
| --- | --- |
| Cobalt | 55 |
| Chromium | 20 |
| Tungsten | 25 |

Substituting W for Ni on a weight percentage basis increases the calculated radiopacity from 3.6 to 4.4 barnes/cc. From a metallurgical perspective, Co—Cr will fall in the same region as for L-605. Otherwise, the alloy will contain a mixture of HCP $\varepsilon$Co and HCP Co$_3$W, and BCC ($\alpha_1$+$\alpha_2$) phases.

Example 62—ASTM F90 L-605 Alloy with Weight Substitution of Nickel and a Portion of the Cobalt with Tungsten

| Element | Weight Percent |
| --- | --- |
| Cobalt | at least 35 |
| Chromium | 20 |
| Tungsten | up to 45 |

It is assumed that Cr is not changed, thus Co—Cr is the same as for L-605. From a metallurgical phase diagram perspective, W may be included up to about 45 weight percent. At 45 weight percent W, this gives a radiopacity of 7.9 barnes/cc and metallurgically would result in a mix of rhombohedral Co$_7$W$_6$ and HCP Co$_3$W, and BCC ($\alpha_1$+$\alpha_2$) phases.

Example 63—ASTM F562 MP-35N Alloy with Weight Substitution of Nickel with Tungsten

| Element | Weight Percent |
| --- | --- |
| Cobalt | 35 |
| Chromium | 20 |
| Molybdenum | 10 |
| Tungsten | 35 |

Utilizing a straight substitution of tungsten for nickel on a weight percentage basis increases the radiopacity from 3.4 barnes/cc to 6.1 barnes/cc. From a metallurgical perspective, Co—Cr, Co—Mo, and Cr—Mo fall in the same regions as MP-35N. Other phases will include HCP Co$_3$W, BCC ($\alpha_1$+$\alpha_2$), and BCC Mo and BCC W phases.

Example 64—ASTM F562 NIP-35N Alloy with Weight Substitution of Nickel and a Portion of the Cobalt with Tungsten

| Element | Weight Percent |
| --- | --- |
| Cobalt | at least 20 |
| Chromium | 20 |
| Molybdenum | 10 |
| Tungsten | up to 50 |

While avoiding the Co—Cr σ intermetallic phase W may be included up to 50 weight percent. This increases radiopacity to 7.7 barnes/cc. Metallurgically, this results in the presence of rhombohedral $Co_7W_6$ BCC ($\alpha_1+\alpha_2$) and BCC Mo and BCC W phases. Another example may further increase the tungsten to up to 60% by replacing the molybdenum with tungsten. This would further increase radiopacity, and result in the same phases present as described relative to an alloy including up to 50 weight percent tungsten. Of course, such a modified alloy could also be relative to (or derived from) L-605, as both would include at least 20% Co, 20% Cr, and up to 60% W.

Examples 65-68 below are based on the nominal compositions of the ASTM F90 L-605 Alloy of Table 1 and the ASTM F562 MP-35N Alloy of Table 3 in which at least the nickel, and in some examples, some of the cobalt has been replaced on an weight substitution basis with a refractory metal, zirconium. Example 69 further replaces the tungsten of L-605 or the molybdenum of MP-35N with zirconium so that the alloy is essentially a ternary Co—Cr—Zr alloy. Trace elements such as beryllium, boron, carbon, iron, manganese, phosphorus, silicon, sulfur, and titanium are not listed.

Example 65—ASTM F90 L-605 Alloy with Weight Substitution of Nickel with Zirconium

| Element | Weight Percent |
| --- | --- |
| Cobalt | 55 |
| Chromium | 20 |
| Tungsten | 15 |
| Zirconium | 10 |

Substituting Zr for Ni on a weight percentage basis increases the calculated radiopacity from 3.6 to 4.1 barnes/cc. From a metallurgical perspective, the Co—Cr, Co—W, and Cr—W will fall in the same regions as for L-605. Otherwise the alloy will contain a mixture of HCP εCo and γ(CoZr), FCC $\alpha ZrCr_2$ and BCC Cr, FCC $W_2Zr$, and HCP (αZr) phases.

Example 66—ASTM F90 L-605 Alloy with Weight Substitution of Nickel and a Portion of the Cobalt with Zirconium

| Element | Weight Percent |
| --- | --- |
| Cobalt | at least 20 |
| Chromium | 20 |
| Tungsten | 15 |
| Zirconium | up to 45 |

As with the above alloys of Ag, Au, Hf, Mo, Nb, Re, and Ta, here it is assumed that Cr and W are not changed, thus Co—Cr, Co—W, and Cr—W are the same as for L-605. From a metallurgical phase diagram perspective, Zr may be included up to about 45 weight percent. At 45 weight percent Zr, this gives a radiopacity of 5.5 barnes/cc and metallurgically would result in a mix of cubic ζ(CoZr) and BCT η (CoZr), FCC $\alpha ZrCr_2$ and HCP αZr, and FCC $W_2Zr$ and HCP αZr phases.

Example 67—ASTM F562 MP-35N Alloy with Weight Substitution of Nickel with Zirconium

| Element | Weight Percent |
| --- | --- |
| Cobalt | 35 |
| Chromium | 20 |
| Molybdenum | 10 |
| Zirconium | 35 |

Utilizing a straight substitution of zirconium for nickel on a weight percentage basis increases the radiopacity from 3.4 barnes/cc to 4.8 barnes/cc. From a metallurgical perspective, Co—Cr, Co—Mo, and Cr—Mo fall in the same regions as MP-35N. Other phases will include FCC ε(CoZr) and cubic ζ(CoZr), FCC $\alpha ZrCr_2$ and HCP αZr, and FCC $Mo_2Zr$, and BCC Mo phases.

Example 68—ASTM F562 MP-35N Alloy with Weight Substitution of Nickel and a Portion of the Cobalt with Zirconium

| Element | Weight Percent |
| --- | --- |
| Cobalt | at least 20 |
| Chromium | 20 |
| Molybdenum | 10 |
| Zirconium | up to 50 |

While avoiding the Co—Cr σ intermetallic phase Zr may be included up to 50 weight percent. This increases radiopacity to 5.3 barnes/cc. Metallurgically, this results in the presence of cubic ζ(CoZr) and BCT η(CoZr), FCC $\alpha ZrCr_2$ and HCP αZr, FCC $Mo_2Zr$, and HCP αZr phases.

Example 69—ASTM F90 L-605 Alloy or ASTM F562 MP-35N Alloy with Weight Substitution of Nickel and Tungsten or Molybdenum with Zirconium

| Element | Weight Percent |
|---|---|
| Cobalt | at least 20 |
| Chromium | 20 |
| Zirconium | up to 60 |

When considering a simpler mixture, the alloy may be considered without either Mo or W, i.e., consisting of Zr—Co—Cr only. In this instance, the Zr may range up to about 60 weight percent to avoid the Co—Cr σ intermetallic phase. At 60 weight percent Zr, calculated radiopacity would be 5.0 barnes/cc. Co—Zr falls close to the BCT η(CoZr) phase, but would also likely include some cubic ζ(CoZr) phase as well. The Cr—Zr falls in the FCC αZrCr$_2$ and HCP αZr phase regime.

Exemplary alloys of Examples 25-69, even those with relatively complex phase diagrams, are expected to provide viable alloys for use in stent fabrication. Enhancing the radiopacity of the alloy while remaining viable from metallurgical and engineering perspectives allows the fabrication of improved medical devices, particularly stents where greater radiopacity is beneficial.

Examples 70-73 describe particular ternary cobalt-chromium-iridium alloys that are somewhat similar to Examples 7-8, but which are essentially ternary alloys and do not include elements other than cobalt, chromium, and iridium. Such an embodiment may include chromium at a level from about 10 to about 25 atomic percent, more particularly from about 15 to about 25 (e.g., about 20 atomic percent) atomic percent to impart the desired tightly adhering Cr$_2$O$_3$ oxide layer that provides excellent corrosion resistance. The cobalt and iridium levels may be varied in virtually any ratio, depending on desired radiopacity, degree of ferromagnetism, and mechanical strength because cobalt and iridium are mutually soluble in one another and therefore do not form undesirable intermetallic phases. In order to avoid ferromagnetism at room temperature, the ratio of iridium to cobalt may be selected so as to be greater than about 1:1 on an atomic percentage basis. The result is a radiopaque, corrosion resistant, and relatively inexpensive ternary alloy system for stents. Iridium is attractive because it has slightly better radiopacity than platinum and has a cost approximately half that of platinum and similar to that of palladium. Similar ternary alloys including only cobalt, chromium, and a metal other than iridium (e.g., Pt, Pd, Ru, Rh, or Os) could similarly be provided. Such ternary alloys may include similar atomic fractions as those described above and in Examples 70-73 but in which the Iridium is substituted with Pt, Pd, Ru, Rh, or Os. Similar ternary alloys could also be formed from Co, Cr, and a refractory metal or precious metal (i.e., silver or gold).

According to one embodiment, such a ternary alloy is not based on any existing commercially available alloy composition such as L-605 or MP-35N so that it does not contain extra elements such as tungsten, molybdenum, iron, manganese, etc. and thus minimizes the complexity in terms of intermetallics, precipitate formation, etc.

Example 70—Ternary Cobalt-Chromium-Iridium Alloy

| Element | Atomic Percent |
|---|---|
| Cobalt | 35 |
| Chromium | 20 |
| Iridium | 45 |

Example 71—Ternary Cobalt-Chromium-Iridium Alloy

| Element | Atomic Percent |
|---|---|
| Cobalt | 30 |
| Chromium | 20 |
| Iridium | 50 |

Example 72—Ternary Cobalt-Chromium-Iridium Alloy

| Element | Atomic Percent |
|---|---|
| Cobalt | 25 |
| Chromium | 20 |
| Iridium | 55 |

Example 73—Ternary Cobalt-Chromium-Iridium Alloy

| Element | Atomic Percent |
|---|---|
| Cobalt | 20 |
| Chromium | 20 |
| Iridium | 60 |

As mentioned previously, a platinum group metal, refractory metal, or precious metal may replace elements in addition to the nickel of an existing commercially available alloy such as L-605, MP-35N, Elgiloy, or Phynox. For example, in L-605, the nickel is included as an austenitic stabilizer. Nickel and the platinum group elements palladium and platinum are group 10 elements. Thus, platinum and palladium may also be expected to act as austentic stabilizers in cobalt. In addition, cobalt and each of the three group 10 elements (nickel, palladium, and platinum) are mutually dissolvable in each other. Platinum and/or palladium may be substituted for nickel in L-605 to improve radiopacity. Where insufficient radiopacity is provided under atomic percentage substitution as described in Examples 1 and 3, at least some of the cobalt of an alloy such as L-605 may also be replaced with the platinum group metal to further increase the radiopacity. Examples 74-75 and Examples 76-77 describe such examples that are similar to 1 and 3, respectively, but also replace at least a portion of the cobalt to further increase radiopacity. Similar examples could be provided based on alloys other than L-605 (e.g., MP-35N, Elgiloy, or Phynox)

Example 74—ASTM F90 L-605 Alloy with Atomic Substitution of Nickel and a Portion of the Cobalt with Platinum

| Element | Atomic Percent |
| --- | --- |
| Cobalt | 48.9 |
| Chromium | 24.4 |
| Tungsten | 5.2 |
| Platinum | 15.8 |
| Manganese (maximum) | 2.3 |
| Iron (maximum) | 3.4 |

Example 75—ASTM F90 L-605 Alloy with Atomic Substitution of Nickel and a Portion of the Cobalt with Platinum

| Element | Atomic Percent |
| --- | --- |
| Cobalt | 43.9 |
| Chromium | 24.4 |
| Tungsten | 5.2 |
| Platinum | 20.8 |
| Manganese (maximum) | 2.3 |
| Iron (maximum) | 3.4 |

Example 76—ASTM F90 L-605 Alloy with Atomic Substitution of Nickel and a

Portion of the Cobalt with Palladium

| Element | Atomic Percent |
| --- | --- |
| Cobalt | 48.9 |
| Chromium | 24.4 |
| Tungsten | 5.2 |
| Palladium | 15.8 |
| Manganese (maximum) | 2.3 |
| Iron (maximum) | 3.4 |

Example 77—ASTM F90 L-605 Alloy with Atomic Substitution of Nickel and a

Portion of the Cobalt with Palladium

| Element | Atomic Percent |
| --- | --- |
| Cobalt | 43.9 |
| Chromium | 24.4 |
| Tungsten | 5.2 |
| Palladium | 20.8 |
| Manganese (maximum) | 2.3 |
| Iron (maximum) | 3.4 |

As mentioned previously, a platinum group metal, refractory metal, or precious metal may replace elements in addition to the nickel of an existing commercially available alloy such as L-605, MP-35N, Elgiloy, or Phynox. Several of the above embodiments include substitution of a portion of the cobalt in addition to substitution of the nickel. Another embodiment may specifically substitute the refractory metal (e.g., molybdenum or tungsten) present within the commercial alloy, replacing this refractory metal with a platinum group metal (particularly preferred substituting platinum group metals include Pt, Pd, Ir, and Rh. Another embodiment may substitute with another refractory metal (e.g., substitute Mo with Re). Another embodiment may substitute the refractory metal with iron, which if done, is may be present in a small amount, as described herein. Many of these alloy embodiments may also replace the nickel, and optionally a portion of the cobalt, chromium, or even both, with a platinum group metal, particularly preferred of which would be Pt.

For example, a base research alloy which still includes the refractory metal (e.g., molybdenum) is herein designated MP1 has a composition as shown below in Table 5. MP1 may be considered to be a more heavily substituted variant of MP-35N, as the amount of chromium is lower (13.5% vs. 20% by weight) and the amount of molybdenum is lower (6.7% vs. 10%). Some of the chromium and molybdenum, as well as all the nickel and a portion of the cobalt has been replaced with platinum.

TABLE 5

| MP1 Alloy | | |
| --- | --- | --- |
| Element | Weight Percent | Atomic Percent |
| Cobalt | 23.3 | 39.0 |
| Chromium | 13.5 | 25.6 |
| Molybdenum | 6.7 | 6.9 |
| Platinum | 56.5 | 28.5 |

In evaluating various of the earlier described cobalt-chromium-platinum group alloys described above in conjunction with Examples 1-24, it was found that as ingots were prepared by melting and then worked to evaluate their workability, a greater understanding of ambient temperature workability (i.e., cold workability) of these alloys was gained. Ordinarily significant reduction in workability when platinum is added to 316L stainless steel at greater than 33 weight percent is expected. However, this reduction in workability did not occur in at least some of the present alloy systems described herein. Rather, some of the initial platinum substituted alloy melts with greater than 33 weight percent platinum were workable as evidenced by being rolled at up to 50% deformation.

One of the most promising precious metal substitution alloys melted and processed was MP1, described in Table 5 above. Other alloys with greater percentages of Pd that were investigated with off stoichiometric alloy compositions showed good workability, but resulted in lower than desired densities. Pd (density of 12.02 g/cm$^3$) is significantly less dense than Pt (density of 21.45 g/cm$^3$). Thus, substitution with platinum may be particularly preferred. Alloy MP1 maintains a high density (12.8 g/cm$^3$) and a relative radiopacity of 9.8 barnes/cm$^3$. While this alloy showed good workability after casting, microstructural changes resulted in somewhat lower workability after heat treatment.

In order to further improve the workability of the MP1 alloy, additional quaternary (and in some cases pentenary) alloys were investigated by replacing the molybdenum in the MP1 alloy, as described above. Example 87 is a ternary alloy in which the molybdenum is replaced with additional cobalt. Examples 78-89 in Table 6 below show the resulting compositions. Refractory metal elements such as molybdenum and tungsten are typically used for strengthening, but can also reduce workability. The specific substitutions shown in Examples 78-89 of Table 6 are based on phase diagram analysis. Examples 81, 85, and 87 were actually formed by melting, and then worked to evaluate their workability characteristics. Of these three, Examples 85 and 87 showed the best cast workability in rolling, with Example 85 being slightly better.

TABLE 6

Variants of Mfg With Substitution of Molybdenum

| Alloy | Pt wt % at % | Co wt % at % | Cr wt % at % | Fe wt % at % | Ir wt % at % | Pd wt % at % | Re wt % at % | Rh wt % at % | Density (g/cm³) | RR (barnes/cm³) |
|---|---|---|---|---|---|---|---|---|---|---|
| Ex. 78 | 56.5 (28.7) | 23.3 (39.2) | 13.5 (25.8) | | | 6.7 (6.2) | | | 13.0 | 10.1 |
| Ex. 79 | 52 (24.9) | 23.3 (36.9) | 18 (32.3) | | | 6.7 (5.9) | | | 12.3 | 9.2 |
| Ex. 80 | 54 (26.5) | 23.3 (37.9) | 16 (29.5) | | | 6.7 (6.0) | | | 12.6 | 9.6 |
| Ex. 81 | 54.2 (27.3) | 23.3 (38.9) | 13.5 (25.5) | | | 9.0 (8.3) | | | 12.8 | 10.1 |
| Ex. 82 | 43.7 (20.6) | 23.3 (36.4) | 18 (31.9) | | | 10 (8.6) | 5 (2.5) | | 12.1 | 9.1 |
| Ex. 83 | 56.5 (29.5) | 23.3 (40.3) | 13.5 (26.5) | | | | 6.7 (3.7) | | 13.4 | 10.0 |
| Ex. 84 | 52.9 (26.2) | 23.1 (37.9) | 16 (29.8) | | 5 (4.5) | | 3 (1.6) | | 12.7 | 9.0 |
| Ex. 85 | 56.5 (27.2) | 23.3 (37.1) | 13.5 (24.4) | 6.7 (11.3) | | | | | 12.5 | 8.9 |
| Ex. 86 | 56.5 (28.7) | 23.3 (39.2) | 13.5 (25.7) | | | | | 6.7 (6.4) | 13.0 | 10.1 |
| Ex. 87 | 56.5 (27.4) | 30.0 (48.1) | 13.5 (24.5) | | | | | | 12.7 | 9.0 |
| Ex. 88 | 56.5 (29.6) | 23.3 (40.4) | 13.5 (26.5) | | 6.7 (3.6) | | | | 13.5 | 10.2 |
| Ex. 89 | 40 (19.0) | 23.3 (36.6) | 13.5 (24.0) | | | 13.2 (11.5) | | 10 (9.0) | 12.1 | 10.0 |

Generally, many of Examples 78-89 are nickel-free, molybdenum-free cobalt-based alloys comprising from about 18 weight percent to about 39 weight percent cobalt, from about 10 weight percent to about 25 weight percent chromium, from about 40 weight percent to about 65 weight percent platinum, and from about 5 weight percent to about 25 weight percent of one or more other platinum group metals, refractory metals, or combinations thereof. In another embodiment, and as will be apparent from Examples 78-89, the cobalt-based alloy may comprise from about 18 weight percent to about 30 weight percent cobalt, from about 10 weight percent to about 20 weight percent chromium, and from about 45 weight percent to about 60 weight percent platinum. In another embodiment, and as will be apparent from Examples 78-89, the cobalt-based alloy may comprise from about 18 weight percent to about 25 weight percent cobalt, from about 10 weight percent to about 15 weight percent chromium, and from about 50 weight percent to about 60 weight percent platinum. Example 85 substitutes with iron rather than a platinum group metal or refractory metal, while Example 87 substitutes the molybdenum with additional cobalt to result in a ternary alloy. In an embodiment, the alloy may be substantially free or completely free of other refractory metals, other than molybdenum (e.g., tungsten).

Examples 78-81, 83, and 86-87 are quaternary alloys comprising cobalt, chromium, platinum, and one other platinum group metal or refractory metal. Examples 82, 84, and 89 are pentenary alloy comprising cobalt, chromium, platinum, and one or more other platinum group metals, refractory metals, or combinations thereof (i.e., two additional elements are selected from platinum group metals, refractory metals, or combinations).

Example 85 can more generally be described as a molybdenum-free cobalt-based alloy comprising from about 18 weight percent to about 39 weight percent cobalt, from about 10 weight percent to about 25 weight percent chromium, from about 40 weight percent to about 65 weight percent platinum, and from about 5 weight percent to about 10 weight percent iron. In one embodiment, iron is present at less than 10 weight percent by weight, or less than 8 weight percent.

With respect to an embodiment including iron, (e.g., Example 85), it is noted that the Fe—Cr phase diagram does include an intermetallic a phase between about 43 and about 48 weight percent chromium (and 52-57 weight percent iron). Although this phase is only formed at elevated temperatures (e.g., from about 440° C. to about 830° C.), such a phase may possibly remain even after such an alloy is cooled to room temperatures. As such, in some embodiments, it may be desired to maintain the ratio of iron to chromium outside of the intermetallic a phase. This phase occurs just below a 1:1 weight ratio of Cr:Fe. In one embodiment, the weight fraction of chromium is greater than the weight fraction of iron so as to clearly avoid this phase. Because Chromium is typically present at a significantly higher level (e.g., 10% plus, 15% plus, etc.) than the iron, this will typically not be an issue. For example, Example 85 includes a Cr:Fe weight ratio of about 2:1. Even where the weight ratio of Cr to Fe is lower (e.g., 1:1, or even 0.8:1) such alloys may still be suitable if no intermetallic is present at the conditions of use (e.g., where the intermetallic phase does not persist at ambient temperature (e.g., near 20° C.)).

Example 87 can more generally be described as a molybdenum-free cobalt-based alloy comprising from about 18 weight percent to about 39 weight percent cobalt, from about 10 weight percent to about 25 weight percent chromium, from about 40 weight percent to about 65 weight percent platinum. The alloy is ternary, the molybdenum of MP1 having been replaced with additional cobalt.

Although the compositions shown in Table 6 are based on MP1 (which is based on MP-35N), it will be understood that alloy variants of L-605, Elgiloy, and Phynox can also be provided by substituting for nickel, for refractory elements (e.g., tungsten in L-605, molybdenum for Elgiloy and Phynox), as well as substituting for some cobalt, some chromium, and iron or other low fraction elements. When these alloys are reduced to quaternary or pentenary form with relative radiopacities greater than 5.5 barnes/cm$^3$, the possible elemental compositions may be similar to those shown above in Table 6, as well as various examples discussed previously. As such, these variants of L-605, Elgiloy, and Phynox are also within the scope of the present disclosure.

TABLE 7

ASTM F90 L-605 Alloy

| Element | Weight Percent | Atomic Percent | Volume Percent |
|---|---|---|---|
| Cobalt | 53.4 | 57.4 | 55.0 |
| Chromium | 20 | 24.4 | 25.4 |
| Tungsten | 15 | 5.2 | 7.1 |
| Nickel | 10 | 10.8 | 10.3 |
| Manganese | 1.5 | 1.7 | 1.9 |
| Carbon | 0.1 | 0.5 | 0.4 |

Table 7 again shows compositional alloy data for L-605, including slightly differing amounts for cobalt due to a slightly different amount of manganese, as well as the inclusion of a trace amount of carbon. Iron, phosphorus, silicon, and sulfur may also be present in trace amounts not shown in Table 7, which may decrease the amount of cobalt, which may comprise the balance of the alloy.

In further evaluating various of the earlier described cobalt-chromium alloys described above in conjunction with the previous Examples, it was found that additional austenitic stabilization may be needed. As described above, austenitic stabilization allows for the material to be hot and cold worked during processing from ingot to stent.

Cobalt is an allotropic elemental material, and at temperatures up to 422° C. has a hexagonal close-packed (ε-Co, HCP) crystalline structure, while above 422° C. it has a face center cubic (α-Co, FCC) crystalline structure. The ε-HCP microstructure is relatively brittle and prevents appreciable cold working in the material, while the α-FCC, or austenitic cobalt, is more ductile and allows for cold and hot working for processing purposes. As cobalt is alloyed with other elements, the temperature of the ε-Co to α-Co transformation may increase or decrease based on the microstructure, bonding valence, electronegativity, and atom size of the alloying element(s). The response of each element with cobalt is shown in their associated binary phase diagrams. If the transformation temperature decreases with the addition of the alloying element there is an enlarged a field and these elements are considered FCC stabilizers. FCC stabilizers include, but may not be limited to, Al, B, Cu, Ti, Zr, C, Sn, Nb, Mn, Fe, and Ni.

If the transformation temperature increases with the addition of the alloying element, then there is a restricted a field and these elements are considered HCP stabilizers. HCP stabilizers include, but may not be limited to, Si, Ge, Ar, Sb, Cr, Mo, W, Ta, Re, Ru, Os, Rh, Ir, and Pt. In some Co binary alloys, the transition temperature increases for ε-Co→α-Co, while the transformation temperature for α-Co→ε-Co decreases, which makes the transformation more sluggish, and these elements are considered to have a combined stabilization effect (i.e., they may stabilize both FCC and HCP phases), with the phase present at any given condition being stabilized to retard change to the other phase. Elements with a combined effect on the transformation temperature in cobalt include: Be, Pb, V, Pd, Ga, Au.

In the L-605 alloy (composition shown in Tables 1 and 7), nickel serves as an austenitic stabilizer of cobalt, which allows the alloy to be processed using both hot and cold working methods. As described herein, in an embodiment it is desirable for the nickel to be removed to minimize any potential allergy concerns. However, the other two main constituents (Cr and W) in L-605 may not facilitate FCC stabilization of the cobalt, and may instead increase the propensity for HCP structures to form upon working the material.

Furthermore, as described above, there is a desire to increase the radiopacity of the stent material with addition of platinum group metals, refractory metals, and/or precious metals, such as silver (Ag), gold (Au), hafnium (Hf), iridium (Ir), molybdenum (Mo), palladium (Pd), platinum (Pt), rhenium (Re), rhodium (Rh), tantalum (Ta), tungsten (W), and/or zirconium (Zr), which are more radiopaque than nickel. Radiopaque elements such as Au, Ir, Pd, Pt, Re, Ta, and W all significantly improve radiopacity of the material as their relative radiopacity is at least four times higher than nickel; however, none of these elements may be, strictly speaking, FCC stabilizers. Therefore, an increase in concentration of one or more FCC austenitic stabilizers may therefore be important for the workability of an alloy material based on L-605 aimed at increasing the radiopacity and limiting nickel content.

The following additional examples are based on modification of a base L-605 alloy. It will be apparent that additional analogous examples may be provided based on MP-35N, Elgiloy, or Phynox employing the substitution techniques described herein. In addition, while the following examples employ platinum and/or palladium, it will be understood that other platinum group metals, refractory metals, and/or precious metals may be included instead of or in addition to Pt and/or Pd to increase the radiopacity to a desired level.

Manganese (Mn) and iron (Fe) are both FCC stabilizers of cobalt based alloys and are present in L-605 alloy in low amounts, as shown in Tables 1 & 7. Since Mn is already present in the L-605 alloy, increasing the levels of this element is not expected to adversely react with the current chemistry. Increased amounts of Fe have the potential to increase the magnetic response of the material, which may not be desirable in an implantable medical device, although relatively low levels of iron as described herein may be suitable for use. Any of the above described platinum group elements, refractory metal elements, and/or precious metals (e.g., particularly Au, Pd, Pt, Ta, and/or W) could partially or completely replace the Ni content of L-605 to provide increased radiopacity. As platinum and palladium are in the same periodic table group as nickel they may be particularly good choices to replace the nickel in L-605 to increase radiopacity. At the same time, the concentration of Mn and/or Fe may be increased to provide sufficient austenitic FCC stabilization. Target ranges of Mn and/or Fe are dependent upon the desired level of relative radiopacity and governed by solidification dynamics between the elements; however, a broad class of Pt or Pd L-605 modified alloys are shown below in Table 8.

TABLE 8

Mn and or Fe FCC Stabilized Co—Cr Alloys

| Element | Atomic Percent |
|---|---|
| Cobalt | 57.4 (39.1-57.4) |
| Chromium | 24.4 (20.1-26.0) |
| Tungsten | 5.2 (4.9-5.2) |
| Nickel | 0 to 10.8 |
| Platinum | 1.0 to 10.8 |
| Palladium | 2.0 to 20.0 |
| Manganese | 1.7 to 20.0 |
| Iron | 0 to 10.8 |
| Carbon | 0.1 to 0.5 |

In addition to Mn and Fe as austenitic stabilizers, maintaining some Ni as a stabilizer is also an option explored in some of the examples below. Also, as described above, it is desirable that relatively brittle intermetallics that may form between two or more of the components be avoided.

In an embodiment, the manganese may be present from 1 percent to about 25 percent by weight, from about 1 percent to about 17 percent by weight, or from about 1 percent to about 10 percent by weight In another embodiment the combined weight percentages of the manganese and any nickel (i.e., Mn+Ni) may be present from 1 percent to about 25 percent by weight, from about 1 percent to about 17 percent by weight, or from about 1 percent to about 10 percent by weight.

In another embodiment the combined weight percentages of the manganese, iron, and any nickel (i.e., Mn+Fe+Ni) may be present from 1 percent to about 25 percent by weight, from about 1 percent to about 17 percent by weight, or from about 1 percent to about 10 percent by weight.

TABLE 9A

Specific Mn, Fe, and/or Ni FCC Stabilized Co-Cr Alloys

| Alloy | Co | Cr | Mn | Ni | Pd | Pt | Fe | W | C | RR (barnes/cm³) |
|---|---|---|---|---|---|---|---|---|---|---|
| Example 1 | 57.4 | 24.4 | 1.7 | — | — | 10.8 | — | 5.2 | 0.5 | 7.50 |
| Example 3 | 57.4 | 24.4 | 1.7 | — | 10.8 | — | — | 5.2 | 0.5 | 4.96 |
| Example 90 | 49.1 | 24.4 | 10.8 | — | 10 | — | — | 5.2 | 0.5 | 4.79 |
| Example 91 | 49.1 | 24.4 | 10.8 | — | — | 10 | — | 5.2 | 0.5 | 7.12 |
| Example 92 | 47.4 | 24.4 | 1.7 | — | 10 | — | 10.8 | 5.2 | 0.5 | 4.82 |
| Example 93 | 54.8 | 25.9 | 8.1 | — | 3.6 | 2 | — | 5.1 | 0.5 | 4.78 |
| Example 94 | 55.1 | 26 | 7.9 | — | 2.9 | 2.7 | — | 4.9 | 0.5 | 4.88 |
| Example 95 | 57.4 | 24.4 | 7.9 | — | — | 4.6 | — | 5.2 | 0.5 | 5.35 |
| Example 96 | 57.4 | 24.4 | 4.9 | — | — | 7.6 | — | 5.2 | 0.5 | 6.40 |
| Example 97 | 57.4 | 24.4 | 5.5 | — | 7.0 | — | — | 5.2 | 0.5 | 4.53 |
| Example 98 | 57.4 | 24.4 | 3.6 | — | — | 8.9 | — | 5.2 | 0.5 | 4.75 |
| Example 99 | 56.1 | 20.1 | 2.4 | — | 15.4 | 2 | 3.5 | — | 0.5 | 5.37 |
| Example 100 | 51.9 | 26 | 2.5 | — | 10.9 | 4.6 | 3.6 | — | 0.5 | 5.46 |
| Example 101 | 57.3 | 21.0 | 2.5 | — | 10.9 | 4.2 | 3.6 | — | 0.5 | 5.43 |
| Example 102 | 57.4 | 24.4 | 9.0 | — | — | 3.5 | — | 5.2 | 0.5 | 4.97 |
| Example 103 | 57.4 | 24.4 | 1.7 | 3.3 | — | 7.5 | — | 5.2 | 0.5 | 6.42 |
| Example 104 | 57.4 | 24.4 | 1.7 | 5.3 | — | 5.5 | — | 5.2 | 0.5 | 5.75 |
| Example 105 | 57.4 | 24.4 | 1.7 | 8.0 | — | 2.8 | — | 5.2 | 0.5 | 4.82 |
| Example 106 | 57.4 | 24.4 | 1.7 | 7.3 | — | 3.5 | — | 5.2 | 0.5 | 5.07 |
| Example 107 | 52.6 | 24.4 | 6.5 | — | 10.8 | — | — | 5.2 | 0.5 | 4.91 |
| Example 108 | 39.1 | 24.4 | 20.0 | — | 10.8 | — | — | 5.2 | 0.5 | 4.78 |
| Example 109 | 52.6 | 24.4 | 3.5 | 3.0 | 10.8 | — | — | 5.2 | 0.5 | 4.95 |
| Example 110 | 39.1 | 24.4 | 6.5 | 4.3 | 20.0 | — | — | 5.2 | 0.5 | 5.84 |
| Example 111 | 42.9 | 24.4 | 5.0 | 7.0 | 15.0 | — | — | 5.2 | 0.5 | 5.37 |
| Example 112 | 47.3 | 24.4 | 3.5 | 8.3 | 10.8 | — | — | 5.2 | 0.5 | 4.97 |
| Example 113 | 49.5 | 24.4 | 1.3 | 8.3 | 10.8 | — | — | 5.2 | 0.5 | 4.99 |

TABLE 9B

Specific Mn, Fe, and/or Ni FCC Stabilized Co-Cr Alloys

| Alloy | Co | Cr | Mn | Ni | Pd | Pt | Fe | W | C |
|---|---|---|---|---|---|---|---|---|---|
| Example 1 | 43.3 | 16.2 | 1.2 | — | — | 27.0 | — | 12.2 | 0.1 |
| Example 3 | 49.3 | 18.5 | 1.4 | — | 16.8 | — | — | 13.9 | 0.1 |
| Example 114 | 42.7 | 18.7 | 8.7 | — | 15.7 | — | — | 14.1 | 0.1 |
| Example 115 | 37.8 | 16.5 | 7.7 | — | — | 25.4 | — | 12.5 | 0.1 |
| Example 116 | 41.1 | 18.7 | 1.4 | — | 15.7 | — | 8.9 | 14.1 | 0.1 |
| Example 117 | 48.0 | 20.0 | 6.6 | — | 5.7 | 5.8 | — | 13.8 | 0.1 |
| Example 118 | 48.0 | 20.0 | 6.4 | — | 4.6 | 7.5 | — | 13.4 | 0.1 |
| Example 119 | 48.0 | 19.9 | 8.0 | — | 14.0 | — | — | 10.0 | 0.1 |
| Example 120 | 45.0 | 20.0 | 2.0 | — | 17.0 | 13.0 | 3.0 | — | 0.1 |
| Example 121 | 50.0 | 16.0 | 2.0 | — | 17.0 | 12.0 | 3.0 | — | 0.1 |
| Example 122 | 51.0 | 16.0 | 2.0 | — | 25.0 | — | 3.0 | — | 0.1 |
| Example 123 | 49.7 | 18.7 | 7.3 | — | — | 10.1 | — | 14.1 | 0.1 |
| Example 124 | 45.9 | 17.2 | 1.3 | 2.6 | — | 19.9 | — | 13.0 | 0.1 |
| Example 125 | 47.7 | 17.9 | 1.3 | 4.4 | — | 15.1 | — | 13.5 | 0.1 |
| Example 126 | 50.3 | 18.9 | 1.4 | 7.0 | — | 8.1 | — | 14.2 | 0.1 |
| Example 127 | 49.6 | 18.6 | 1.4 | 6.3 | — | 10.0 | — | 14.0 | 0.1 |
| Example 128 | 45.3 | 18.6 | 5.2 | — | 16.8 | — | — | 14.0 | 0.1 |
| Example 129 | 34.0 | 18.7 | 16.2 | — | 16.9 | — | — | 14.1 | 0.1 |
| Example 130 | 31.7 | 17.4 | 4.9 | 3.5 | 29.3 | — | — | 13.1 | 0.1 |
| Example 131 | 35.9 | 18.0 | 3.9 | 5.8 | 22.7 | — | — | 13.6 | 0.1 |
| Example 132 | 42.6 | 18.5 | 1.0 | 7.1 | 16.8 | — | — | 13.9 | 0.1 |

Generally, many of the Examples 90-132 are similar or identical to one another, as Table 9A reports atomic percentages, while Table 9B reports weight percentages. The Examples of Table 9A are cobalt-based alloys comprising from about 39.1 atomic percent to about 57.4 atomic percent cobalt, from about 20.1 to about 26 atomic percent chromium, from about 1.3 atomic percent manganese to about 20 atomic percent manganese, and from about 2.8 atomic percent to about 20 atomic percent platinum and/or palladium. Examples 90-102 and 107-108 of Table 9A are nickel-free. Examples 90-98 and 102-113 of Table 9A additionally include from about 4.9 to about 5.2 atomic percent tungsten. Examples 92 and 99-101 substitute at least a portion of the nickel of L-605 with iron, and include from about 3.5 atomic percent to about 10.8 atomic percent iron. All Examples of Table 9A are nickel free, or at least include a reduced nickel content as compared to L-605. Examples 103-106 and 109-113 include reduced nickel content, from about 3 atomic percent to about 8.3 atomic percent nickel.

The Examples of Table 9B are cobalt-based alloys comprising from about 31.7 weight percent to about 51 weight percent cobalt, from about 16 weight percent to about 20 weight percent chromium, from about 1 weight percent manganese to about 16.2 weight percent manganese, and from about 8.1 weight percent to about 30 weight percent platinum and/or palladium. Examples 114-123 and 128-129 of Table 9B are nickel-free. Examples 114-119 and 123-132 of Table 9B additionally include from about 10 to about 14.2 weight percent tungsten. Examples 116 and 120-122 substitute at least a portion of the nickel of L-605 with iron, and include from about 3 weight percent to about 8.9 weight percent iron. All Examples of Table 9B are nickel free, or at least include a reduced nickel content as compared to L-605. Examples 124-127 and 130-132 include reduced nickel content, from about 2.6 weight percent to about 7.1 weight percent nickel. Some nickel-containing examples that include a nickel content that is reduced as compared to that of L-605 (10 weight percent) may contain less than 5 percent by weight nickel, or less than 3.5 weight percent nickel. The manganese and/or iron content may be increased to provide a Mn+Fe+Ni content that is as described above (e.g., 1 to 25 weight percent, 1 to 17 weight percent, or 1 to 10 weight percent). Some flexibility may be taken with respect to the Examples. For example, similar examples may be formed that would include the amounts indicated, plus or minus 10%, plus or minus 5%, or plus or minus 3% from the stated atomic percentages, weight percentages, or volume percentages.

Table 10 below shows calculated combined Mn+Fe+Ni weight percentages for the Examples of Table 9B.

TABLE 10

| Alloy | Mn + Fe + Ni Wt % |
| --- | --- |
| Example 1 | 1.2 |
| Example 3 | 1.4 |
| Example 114 | 8.7 |
| Example 115 | 7.7 |
| Example 116 | 10.3 |
| Example 117 | 6.6 |
| Example 118 | 6.4 |
| Example 119 | 8.0 |
| Example 120 | 5.0 |
| Example 121 | 5.0 |
| Example 122 | 5.0 |
| Example 123 | 7.3 |
| Example 124 | 3.9 |
| Example 125 | 5.7 |
| Example 126 | 8.4 |
| Example 127 | 7.7 |
| Example 128 | 5.2 |
| Example 129 | 16.2 |
| Example 130 | 8.4 |
| Example 131 | 9.7 |
| Example 132 | 8.1 |

In an embodiment, the combined weight percentage of the manganese, any iron, and any nickel is from 1 to 17 weight percent, from 1 to 10 weight percent, at least 3 weight percent, at least 4 weight percent, or at least 5 weight percent (e.g., from 3 to 10 weight percent, 4 to 10 weight percent, or 5 to 10 weight percent). The same ranges may apply to Mn+Ni or Mn+Fe. The nickel content may be limited to below that of L-605 alloy (10 weight percent). For example, added nickel may be present at no more than 7.1 weight percent, 7 weight percent, 6.3 weight percent, 5.8 weight percent, 5 weight percent, 4.4 weight percent, 3.5 weight percent, or 2.6 weight percent.

For example, Example 126 includes 7 weight percent nickel and 1.4 weight percent manganese, no more than trace iron, with a combined Mn+Ni content of 8.1 weight percent. Example 127 includes 6.3 weight percent nickel and 1.4 weight percent manganese, no more than trace iron, with a combined Mn+Ni content of 7.7 weight percent. Example 131 includes 5.8 weight percent nickel and 3.9 weight percent manganese, no more than trace iron, with a combined Mn+Ni content of 9.7 weight percent. Example 132 includes 7.1 weight percent nickel and 1.0 weight percent manganese, no more than trace iron, with a combined Mn+Ni content of 8.1 weight percent. As such, examples including 5 weight percent or more nickel (e.g., 5 to 8 weight percent or 5.8 to 7.1 weight percent) may include Mn+Ni content of 7 to 10 weight percent (e.g., 7.7 to 9.7 weight percent). Within such examples including 5 weight percent or more nickel, manganese may be included in amounts of 1 to 10 or 1 to 5 weight percent.

Relative radiopacities of the Examples are shown in Table 9A. Of course, those examples which are identical (but reported in weight percent in Table 9B) would have identical relative radiopacity values. Relative radiopacity values for Examples 90-132 range from about 4.53 barnes/cm$^3$ to 7.5 barnes/cm$^3$. In an embodiment, the relative radiopacity may be greater than 4.5 barnes/cm$^3$ or greater than 4.6 barnes/cm$^3$ (e.g., 4.5 barnes/cm$^3$ to 7.5 barnes/cm$^3$, from 4.5 barnes/cm$^3$ to 6.5 barnes/cm$^3$ from 4.6 barnes/cm$^3$ to 7.5 barnes/cm$^3$, or from 4.6 barnes/cm$^3$ to 6.5 barnes/cm$^3$). In an embodiment, such relative radiopacity may be optimum for stent strut thickness of about 60 to about 85 microns (e.g., 62 microns, 81 microns).

In an embodiment, nickel and tungsten are absent. For example, Examples 120, 121, and 122 describe examples based on L-605 in which these components are substituted with platinum and/or palladium. Molybdenum may also be included in any of the formulations. For example, another embodiment may include substitution with palladium and molybdenum. For example, Example 122 may include 3 weight percent Mo. Another embodiment including molybdenum (and perhaps no manganese) may include 40 weight percent cobalt, 18 weight percent chromium, 29 weight percent palladium, 3 weight percent iron, and 10 weight percent nickel, as well as a trace amount (e.g., 0.1 weight percent) carbon. Such an embodiment may exhibit a relative radiopacity of 6.3 barnes/cm$^3$. Another embodiment may include 53.4 weight percent cobalt, 20 weight percent chromium, 1.5 weight percent manganese, 9.0 weight percent palladium, 1 weight percent platinum, and 15 weight percent tungsten. An embodiment may include no nickel, which may be substituted with palladium, with platinum and manganese, with palladium and manganese, or with palladium and iron. Substitution may be based on atomic, weight, or volume percentages of a given component. An embodiment may maintain the Co/Cr ratio of the starting alloy (e.g., L-605), and decrease the amounts of each (while maintaining the ratio), while increasing manganese content and/or increasing platinum and/or palladium content. An embodiment may maintain the Co/Cr ratio of the starting alloy, and add manganese with equal amounts (e.g., weight, volume, or atomic) of platinum and palladium, with tungsten. An embodiment may reduce the tungsten content (e.g., cut in half) and add molybdenum instead, while substituting nickel with platinum and/or palladium. An embodiment may substitute iron for nickel and add palladium and/or platinum for partial cobalt replacement. An embodiment may replace nickel with manganese and reduce cobalt by adding platinum or palladium. An embodiment may maintain the Co/Cr ratio of the starting alloy and add one or more of palladium, manganese, and/or molybdenum.

Although described principally for use in manufacturing stents, it will be understood that any of the disclosed alloys may also be used in the manufacture of guide wires, guide wire tip coils, balloon markers, or other structures associated with catheter use, and other implantable structures in which improved radiopacity would be desirable.

The present invention can be embodied in other specific forms without departing from its spirit or essential characteristics. Thus, the described implementations are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. A radiopaque stent, comprising:
 a cylindrical main body comprising a cobalt-based alloy comprising cobalt, chromium, an austenitic stabilizer for cobalt including a combination of manganese and nickel, and one or more platinum group metals or precious metals selected from the group of platinum, palladium, rhodium, iridium, osmium, ruthenium, silver and gold;
 wherein the cobalt-based alloy comprises from 31 weight percent to 51 weight percent cobalt, from 15 weight percent to 20 weight percent chromium, from 8 weight percent to 30 weight percent of the one or more platinum group metals or precious metals;
 wherein the cobalt-based alloy comprising up to 8 weight percent nickel, up to 20 weight percent manganese, a combined weight percentage of manganese and nickel being up to 25 weight percent, the cobalt-based alloy comprising no more than about 20 percent by weight iron,
 wherein an entirety of the stent is formed from the cobalt-based alloy.

2. The radiopaque stent of claim 1, wherein the cobalt-based alloy includes from 5.8 weight percent to 7.1 weight percent nickel and includes a combined weight percentage of manganese and nickel that is from 7.7 weight percent to 9.7 weight percent.

3. The radiopaque stent of claim 1, wherein the cobalt-based alloy has a radiopacity from 4.6 barnes/cm$^3$ to 6.5 barnes/cm$^3$.

4. The radiopaque stent of claim 1, wherein the cobalt-based alloy includes 5 weight percent to 8 weight percent nickel.

5. The radiopaque stent of claim 1, wherein the cobalt-based alloy includes from 1 to 5 weight percent manganese.

6. The radiopaque stent of claim 1, wherein the cobalt-based alloy includes a combined weight percentage of manganese and nickel from 7 weight percent to 10 weight percent.

7. The radiopaque stent of claim 1, wherein the cobalt-based alloy includes no more than about 4 percent by weight iron.

8. The radiopaque stent of claim 1, wherein the platinum group metal or precious metal comprises at least one of platinum or palladium.

9. The radiopaque stent of claim 1, wherein the platinum group metal or precious metal comprises both platinum and palladium.

10. The radiopaque stent of claim 1, wherein the alloy further comprises tungsten.

11. The radiopaque stent of claim 1, wherein the alloy further comprises up to 15 weight percent tungsten.

12. The radiopaque stent of claim 1, wherein an entirety of the stent is formed from the cobalt-based alloy.

13. The radiopaque stent of claim 12, wherein the cobalt-based alloy includes from 5.8 weight percent to 7.1 weight percent nickel and includes a combined weight percentage of manganese and nickel that is from 7.7 weight percent to 9.7 weight percent.

14. The radiopaque stent of claim 12, wherein the cobalt-based alloy has a radiopacity from 4.6 barnes/cm$^3$ to 6.5 barnes/cm$^3$.

15. The radiopaque stent of claim 12, wherein the platinum group metal or precious metal comprises at least one of platinum or palladium.

16. The radiopaque stent of claim 12, wherein the platinum group metal or precious metal comprises both platinum and palladium.

17. The radiopaque stent of claim 12, wherein the alloy further comprises tungsten.

18. The radiopaque stent of claim 12, wherein the alloy further comprises up to 15 weight percent tungsten.

19. A radiopaque stent, comprising:
 a cylindrical main body comprising a cobalt-based alloy comprising cobalt, chromium, an austenitic stabilizer for cobalt including a combination of manganese and nickel, and one or more platinum group metals or precious metals selected from the group consisting of platinum, palladium, rhodium, iridium, osmium, ruthenium, silver and gold;
 wherein the cobalt-based alloy comprises from 31 weight percent to 51 weight percent cobalt, from 15 weight percent to 20 weight percent chromium, from 8 weight percent to 30 weight percent of the one or more platinum group metals or precious metals;
 wherein the cobalt-based alloy comprises 5 weight percent to 8 weight percent nickel, from 1 weight percent to 5 weight percent manganese, a combined weight percentage of manganese and nickel being from 7 weight percent to 10 weight percent, the cobalt-based alloy comprising no more than about 4 percent by weight iron.

20. The radiopaque stent of claim 19, wherein:
 (i) the cobalt-based alloy includes from 5.8 weight percent to 7.1 weight percent nickel and includes a combined weight percentage of manganese and nickel that is from 7.7 weight percent to 9.7 weight percent; and/or
 (ii) wherein the cobalt-based alloy has a radiopacity from 4.6 barnes/cm$^3$ to 6.5 barnes/cm$^3$.

21. A radiopaque stent, comprising:
 a cylindrical main body comprising a cobalt-based alloy comprising cobalt, chromium, an austenitic stabilizer for cobalt including a combination of manganese and nickel, and one or more platinum group metals or precious metals selected from the group of platinum, palladium, rhodium, iridium, osmium, ruthenium, silver and gold;

wherein the cobalt-based alloy comprises from 31 weight percent to 51 weight percent cobalt, from 15 weight percent to 20 weight percent chromium, from 8 weight percent to 30 weight percent of the one or more platinum group metals or precious metals;

wherein the cobalt-based alloy includes up to 8 weight percent nickel, up to 20 weight percent manganese, a combined weight percentage of manganese and nickel being up to 25 weight percent, the cobalt-based alloy comprising no more than about 20 percent by weight iron, wherein the cobalt-based alloy has a radiopacity from 4.6 barnes/cm$^3$ to 6.5 barnes/cm$^3$.

* * * * *